US009005965B2

(12) United States Patent
Shushan et al.

(10) Patent No.: US 9,005,965 B2
(45) Date of Patent: Apr. 14, 2015

(54) STEM CELLS CULTURE SYSTEMS

(75) Inventors: Etti Ben Shushan, Jerusalem (IL);
Shelly Tannenbaum, Efrat (IL); Pavel Itsykson, Ramat Gan (IL); Eyal Banin, Jerusalem (IL); Benjamin Reubinoff, Doar Na Haela (IL)

(73) Assignee: Hadasit Medical Research Services & Development Limited, Jerusalem (IL)

( * ) Notice: Subject to any disclaimer, the term of this patent is extended or adjusted under 35 U.S.C. 154(b) by 0 days.

(21) Appl. No.: 13/005,978

(22) Filed: Jan. 13, 2011

(65) Prior Publication Data

US 2011/0177594 A1 Jul. 21, 2011

Related U.S. Application Data

(62) Division of application No. 11/794,262, filed as application No. PCT/IL2005/001397 on Dec. 29, 2005, now abandoned.

(60) Provisional application No. 60/639,809, filed on Dec. 29, 2004.

(51) Int. Cl.
| *C12N 5/00* | (2006.01) |
| *C12N 5/071* | (2010.01) |
| *C12N 5/02* | (2006.01) |
| *C12N 5/0735* | (2010.01) |
| *C12N 5/079* | (2010.01) |

(52) U.S. Cl.
CPC ............ *C12N 5/0606* (2013.01); *C12N 5/0621* (2013.01); *C12N 2500/32* (2013.01); *C12N 2500/38* (2013.01); *C12N 2500/44* (2013.01); *C12N 2500/99* (2013.01); *C12N 2501/115* (2013.01); *C12N 2501/155* (2013.01); *C12N 2501/16* (2013.01); *C12N 2506/02* (2013.01); *C12N 2533/52* (2013.01); *C12N 2502/13* (2013.01)

(58) Field of Classification Search
CPC ........... C12N 2500/32; C12N 2502/13; C12N 2500/38; C12N 2501/155; C12N 5/0606; C12N 2533/52; C12N 2501/115; C12N 2506/02; C12N 2500/44; C12N 2500/99; C12N 2501/16
USPC .......................................... 435/373, 366, 325
See application file for complete search history.

(56) References Cited

U.S. PATENT DOCUMENTS

| 5,843,780 | A | 12/1998 | Thomson |
| 5,942,435 | A | 8/1999 | Wheeler |
| 6,180,404 | B1 | 1/2001 | Brewer et al. |
| 6,380,218 | B1 | 4/2002 | Marfat et al. |
| 2003/0143736 | A1 | 7/2003 | Bongso et al. |
| 2003/0161818 | A1* | 8/2003 | Weiss et al. ............... 424/93.21 |
| 2004/0136967 | A1 | 7/2004 | Weiss et al. |
| 2005/0037492 | A1 | 2/2005 | Xu et al. |
| 2005/0196864 | A1 | 9/2005 | Goldman et al. |
| 2006/0073591 | A1 | 4/2006 | Abitorabi et al. |
| 2006/0078543 | A1 | 4/2006 | Reubinoff et al. |
| 2006/0211109 | A1 | 9/2006 | Totey et al. |
| 2011/0027333 | A1 | 2/2011 | Idelson et al. |

FOREIGN PATENT DOCUMENTS

| GB | 2 327 675 A | 2/1999 |
| GB | 2 409 208 A | 6/2005 |
| WO | 98/30679 A1 | 7/1998 |
| WO | 01/55114 A1 | 8/2001 |
| WO | 02/060875 A1 | 8/2002 |
| WO | 03/068233 A1 | 8/2003 |
| WO | WO 03078611 A1 * | 9/2003 |
| WO | 03/104444 A1 | 12/2003 |
| WO | 2004/031343 A2 | 4/2004 |
| WO | 2004/044158 A2 | 5/2004 |
| WO | 2005/014549 A1 | 2/2005 |
| WO | 2005/086845 A2 | 9/2005 |
| WO | 2006/070370 A2 | 7/2006 |
| WO | 2007/002086 A2 | 1/2007 |

OTHER PUBLICATIONS

Troyer et al. Stem Cells, 26: 591-599, 2008.*
Richards et al. Stem Cells, 21: 546-556, Sep. 2003.*
Amit et al. Human Embryonic Stem Cells: Laboratory Manual, pp. 1-42, 2002.*
Zhang et al. Sheng Wu Yi Xue Gong Cheng Xue Za Zhi, 20(2): 251-4, Jun. 2003, Abstract only.*
Draper et al. Stem Cells & Development, 13: 325-336, Sep. 2004.*
NIH, Stem cells: Scientific Progress and Future Research Directions, Chapter 1, pp. 1-4, 2001.*
Lim et al. Proteomics, 2:1187-1203, 2002.*
Sato et al. (2004) Nat. Med. 10:55-63.*
Jing et al. Haemalogica, 95: 542-550, 2010.*
The Sigma-Aldrich catalog (http://www.sigmaaldrich.com/catalog/, accessed online on Jun. 4, 2010, "neural stem cells" and "Stemline Neural Stem cell Expansion Medium".*
Reubinoff, et al., "Embryonic stem cell lines from human blastocysts: somatic differentiation in vitro", Nature Biotechnology, (2000), vol. 18, pp. 399-404.
Amit, et al., "Clonally Derived Human Embryonic Stem Cell Lines Maintain Pluripotency and Proliferative Potential for Prolonged Periods of Culture", Developmental Biology, (2000), vol. 227, pp. 271-278.
Xu, et al., "Feeder-free growth of undifferentiated human embryonic stem cells", Nature Biotechnology, (2001), vol. 19, pp. 971-974.
Cowan, et al., "Derivation of Embryonic Stem-Cell Lines from Human Blastocysts", The New England Journal of Medicine, (2004), vol. 350, No. 13, pp. 1353-1356.

(Continued)

*Primary Examiner* — Thaian N Ton
(74) *Attorney, Agent, or Firm* — Vorys, Sater, Seymour and Pease LLP; Susanne M. Hopkins; Ari G. Zytcer

(57) ABSTRACT

Provided are systems and methods for providing human cell cultures. Further provided are cultures of feeder cells for use in stem cell technology, as well as cultures, culture systems and methods for maintenance and propagating of stem cells in an undifferentiated state as well as for the development of somatic cells cultures from stem cells, the somatic cell cultures being free of extraembryonic cells.

9 Claims, 41 Drawing Sheets

(56) References Cited

OTHER PUBLICATIONS

Pera, et al., "Regulation of human embryonic stem cell differentiation by BMP-2 and its antagonist noggin", Journal of Cell Science, (2004), vol. 117, pp. 1269-1280.
Xu, et al., "Basic FGF and suppression of BMP signaling sustain undifferentiated proliferation of human ES cells", Nature Methods, (2005), vol. 2, No. 3, pp. 185-190.
Itsykson, et al., "Derivation of neural precursors from human embryonic stem cells in the presence of noggin", Mol. Cell. Neurosci., (2005), vol. 30, pp. 24-36.
Yan, et al., "Directed Differentiation of Dopaminergic Neuronal Subtypes from Human Embryonic Stem Cells", Stem Cells, (2005), vol. 23, pp. 781-790.
Ludwig, et al., "Derivation of human embryonic stem cells in defined conditions", Nature Biotechnology, (2006), vol. 24, No. 2, pp. 185-187.
Kallos, et al., "Large-scale expansion of mammalian neural stem cells: A review", Med. Biol. Eng. Comput., (2003), vol. 41, pp. 271-282.
Gerecht-Nir, et al., "Bioreactor Cultivation Enhances the Efficiency of Human Embryoid Body (hEB) Formation and Differentiation", Biotechnology and Bioengineering, (2004), vol. 86, No. 5, pp. 493-502.
Goldsborough, et al., "Serum-free culture of murine embryonic stem (ES) cells", Focus, (1998), vol. 20, No. 1, pp. 8-12.
Reubinoff, et al., "Identification and Maintenance of Neural Precursors from Human Embryonic Stem Cells", Handbook of Stem Cells, (2004), vol. 1, Chapter 49, pp. 511-520.
Klimanskaya, et al., "Human embryonic stem cell lines derived from single blastomeres", Nature, (2006), vol. 444, pp. 481-485, Addendum.
D'Amour, et al., "Production of pancreatic hormone-expressing endocrine cells from human embryonic stem cells", Nature Biotechnology, (2006), vol. 24, No. 11, pp. 1392-1401.
Yao, et al., "Long-term self-renewal and directed differentiation of human embryonic stem cells in chemically defined conditions", PNAS, (2006), vol. 103, No. 18, pp. 6907-6912.
Turetsky, et al., "Laser-assisted derivation of human embryonic stem cell lines from IVF embryos after preimplantation genetic diagnosis", Human Reproduction, (2008), vol. 23, No. 1, pp. 46-53.
Thomson, et al., "Private Embryonic Stem Cells", Current Topics in Developmental Biology, (1998), vol. 38, Chapter 4, pp. 133-165.
Thomson, et al., "Isolation of a primate embryonic stem cell line", Proc. Natl. Acad. Sci. USA, (1995), vol. 92, pp. 7844-7848.
Bongso, et al., "Improved quality of human embryos when co-cultured with human ampullary cells", Human Reproduction, (1989), vol. 4, No. 6, pp. 706-713.
Gardner, et al., "Culture and transfer of human blastocysts increases implantation rates and reduces the need for multiple embryo transfers", Fertility and Sterility, (1998), vol. 69, No. 1, pp. 84-88.
Thomson, et al., "Embryonic Stem Cell Lines Derived from Human Blastocysts", Science, (1998), vol. 282, pp. 1145-1147.
Carpenter, et al., "Characterization and Differentiation of Human Embryonic Stem Cells", Cloning and Stem Cells, (2003), vol. 5, No. 1, pp. 79-88.
Brewer, "Serum-free B27/Neurobasal medium supports differential growth of neurons from the striatum, substantia nigra, septum, cerebral cortex, cerebellum, and dentate gyrus", Journal of Neuroscience Research, (1995), vol. 42, pp. 674-683.
Gearhart, "New Potential for Human Embryonic Stem Cells", Science, (1998), vol. 282, No. 5391, pp. 1061-1062.
Rossant, et al., "In search of the tabula rasa of human cells", Nature Biotechnology, (1999), vol. 17, pp. 23-24.
Martin, et al., "Human embryonic stem cells express an immunogenic nonhuman sialic acid", Nature Medicine, (2005), vol. 11, No. 2, pp. 228-232.
Richards, et al., "Human feeders support prolonged undifferentiated growth of human inner cell masses and embryonic stem cells", Nature Biotechnology, (2002), vol. 20, pp. 933-936.
Vaca, et al., "Nicotinamide Induces Both Proliferation and Differentiation of Embryonic Stem Cells Into Insulin-Producing Cells", Transplantation Proceedings, (2003), vol. 35, pp. 2021-2023.
Haruta, et al., "In vitro and in vivo characterization of pigment epithelial cells differentiated from primate embryonic stem cells", Invest Ophthalmol Vis Sci, (2004), vol. 45, pp. 1020-1025.
Ohno-Matsui, et al., "In vitro and in vivo characterization of iris pigment epithelial cells cultured on amniotic membranes", Molecular Vision, (2006), vol. 12, pp. 1022-1032.
Conti, et al., "Niche-independent symmetrical self-renewal of a mammalian tissue stem cell", PLoS Biology, (2005), vol. 3, Issue 9, pp. 1594-1606.
Coucouvanis, et al., "Signals for death and survival: a two-step mechanism for cavitation in the vertebrate embryo", Cell, (1995), vol. 83, pp. 279-287.
Doetschman, et al., "The in vitro development of blastocyst-derived embryonic stem cell lines: formation of visceral yolk sac, blood islands and myocardium", J. Embryol. exp. Morph., vol. 87, pp. 27-45, (1985).
Roach, et al., "Hepatocytic transcription factor expression in human embryonal carcinoma and yolk sac carcinoma cell lines: expression of HNF-3α in models of early endodermal cell differentiation", Experimental Cell Research, (1994), vol. 215, pp. 189-198.
Kemler, et al., "Reactivity of monoclonal antibodies against intermediate filament proteins during embryonic development", J. Embryol. exp. Morph., (1981), vol. 64, pp. 45-60.
Smith, et al., "Risk Factors for Age-related Macular degeneration: Pooled findings from three continents", Ophthalmology, (2001), vol. 108, pp. 697-704.
Nakayama, et al., "A novel chordin-like protein inhibitor for bone morphogenetic proteins expressed preferentially in mesenchymal cell lineages", Developmental Biology, (2001), vol. 232, pp. 372-387.
Abreu, et al., "Chordin-like CR domains and the regulation of evolutionarily conserved extracellular signaling systems", Gene, (2002), vol. 287, pp. 39-47.
Amit, et al., "Human Feeder Layers for Human Embryonic Stem Cells", Biology of Reproduction, (2003), vol. 68, pp. 2150-2156.
Bodnar, et al., "Propagation and Maintenance of Undifferentiated Human Embryonic Stem Cells", Stem Cells and Development, (2004), vol. 13, pp. 243-253.
Köhler, et al., "Defining Optimum Conditions for the Ex Vivo Expansion of Human Umbilical Cord Blood Cells. Influences of Progenitor Enrichment, Interference with Feeder Layers, Early-Acting Cytokines and Agitation of Culture Vessels", Stem Cells, (1999), vol. 17, pp. 19-24.
Amit, et al., "Feeder Layer- and Serum-Free Culture of Human Embryonic Stem Cells", Biology of Reproduction, (2004), vol. 70, pp. 837-845.
Cameron, et al., "Improved Development of Human Embryonic Stem Cell-Derived Embryoid Bodies by Stirred Vessel Cultivation", Biotechnology and Bioengineering, (2006), vol. 94, No. 5, pp. 938-948.
Cormier, et al., "Expansion of Undifferentiated Murine Embryonic Stem Cells as Aggregates in Suspension Culture Bioreactors", Tissue Engineering, (2006), vol. 12, No. 11, pp. 3233-3245.
Ye, et al., "Establishment of an adherent cell feeder layer from human umbilical cord blood for support of long-term hematopoietic progenitor cell growth", Proc. Natl. Acad. Sci. USA, vol. 91, pp. 12140-12144, (1994).
Dang, et al., "Efficiency of Embryoid Body Formation and Hematopoietic Development from Embryonic Stem Cells in Different Culture Systems", Biotechnology and Bioengineering, (2002), vol. 78, No. 4, pp. 442-453.
Fok, et al., "Shear-Controlled Single-Step Mouse Embryonic Stem Cell Expansion and Embryoid Body-Based Differentiation", Stem Cells, (2005), vol. 23, pp. 1333-1342.
Gerami-Naini, et al., "Trophoblast Differentiation in Embryoid Bodies Derived from Human Embryonic Stem Cells", Endocrinology, (2004), vol. 145, No. 4, pp. 1517-1524.
Nieden, et al., "Embryonic stem cells remain highly pluripotent following long term expansion as aggregates in suspension bioreactors", Journal of Biotechnology, (2007), vol. 129, pp. 421-432.

(56) References Cited

OTHER PUBLICATIONS

Steiner, et al., "Derivation, propagation and controlled differentiation of human embryonic stem cells in suspension", Nature Biotechnology, (2010), vol. 28, No. 4, pp. 361-366.
Ulloa-Montoya, et al., "Culture Systems for Pluripotent Stem Cells", Journal of Bioscience and Bioengineering, (2005), vol. 100, No. 1, pp. 12-27.
Vallier, et al., "Activin/Nodal and FGF pathways cooperate to maintain pluripotency of human embryonic stem cells", Journal of Cell Science, (2005), vol. 118, No. 19, pp. 4495-4509.
Van Dijk, et al., "Kinetics and regulation of site-specific endonucleolytic cleavage of human IGF-II mRNAs", Nucleic Acids Research, vol. 29, No. 17, pp. 3477-3486, (2001).
Brewer, et al., "Optimized Survival of Hippocampal Neurons in B27-Supplemented Neurobasal, a New Serum-free Medium Combination", Journal of Neuroscience Research, vol. 35, pp. 567-576, (1993).
Thoennes, et al., "Differential transcriptional activation of peroxisome proliferator-activated receptor gamma by omega-3 and omega-6 fatty acids in MCF-7 cells", Molecular and Cellular Endocrinology, vol. 160, pp. 67-73, (2000).
Aoki, et al., "Embroyonic stem cells that differentiate into RPE cell precursors in vitro develop int RPE cell monolayers in vivo", Experimental Eye Research, vol. 82, pp. 265-274, (2006).
Chang, et al., "Blastocyst formation, karyotype, and mitochondrial DNA of interspecies embryos derived from nuclear transfer of human cord fibroblasts into enucleated bovine oocytes", Fertility and Sterility, vol. 80, No. 6, pp. 1380-1387, (2003).
Fryer, et al., "Human Endothelium in Cell Culture", J. Atheroscler. Res., vol. 6, pp. 151-163, (1966).
Houtenbos, et al., "Serum-free generation of antigen presenting cells from acute myeloid leukaemic blasts for active specific immunisation", Cancer Immunol. Immunother, vol. 52, pp. 455-462, (2003).
Idelson, et al., "Directed Differentiation of Human Embryonic Stem Cells into Functional Retinal Pigment Epithelium Cells", Cell Stem Cell, vol. 5, pp. 396-408, (2009).
Kawasaki, et al., "Generation of dopaminergic neurons and pigmented epithelia from primate ES cells by stromal cell-derived inducing activity", PNAS, vol. 99, No. 3, pp. 1580-1585, (2002).
Lam, et al., "Preclinical ex vivo expansion of cord blood hematopoietic stem and progenitor cells: duration of culture; The media, serum supplements, and growth factors used; and engraftment in NOD/SCID mice", Transfusion, vol. 41, pp. 1567-1576, (2001).
Laslett, et al., "Characterization and Culture of Human Embryonic Stem Cells", TCM, vol. 13, No. 7, pp. 295-301, (2003).
Moog, et al., "Platelet glycoprotein V binds to collagen and participates in platelet adhesion and aggregation", Blood, vol. 98, pp. 1038-1046, (2001).
Nakamura, et al., "Morphologic evaluation of the antitumor activity of photodynamic therapy (PDT) using mono-L-aspartyl chlorin e6 (NPe6) against uterine cervical carcinoma cell lines", Int J Gynecol Cancer, vol. 12, pp. 177-186, (2002).
Rao, et al., "Culture development for human embryonic stem cell propagation: molecular aspects and challenges", Current Opinion in Biotechnology, vol. 16, pp. 568-576, (2005).
Reubinoff, et al., "Neural progenitors from human embryonic stem cells", Nature Biotechnology, vol. 19, pp. 1134-1140, (2001).
Shen, et al., "Protective Effect of Nicotinamide on Neuronal Cells under Oxygen and Glucose Deprivation and Hypoxia/Reoxygenation", J Biomed Sci, vol. 11, pp. 472-481, (2004).
Suemori, et al., "Establishment of Embryonic Stem Cell Lines From Cynomolgus Monkey Blastocysts Produced by IVF or ICSI", Developmental Dynamics, vol. 222, pp. 273-279, (2001).
Humphrey, et al., "Maintenance of Pluripotency in Human Embryonic Stem Cells Is STAT3 Independent", Stem Cells, vol. 22, pp. 522-530, (2004).
Valdimarsdottir, et al., "Functions of the TGFβ superfamily in human embryonic stem cells", APMIS, vol. 113, pp. 773-789, (2005).

\* cited by examiner

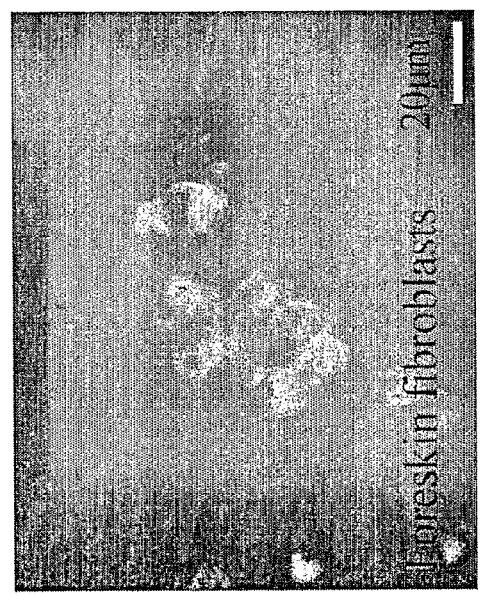
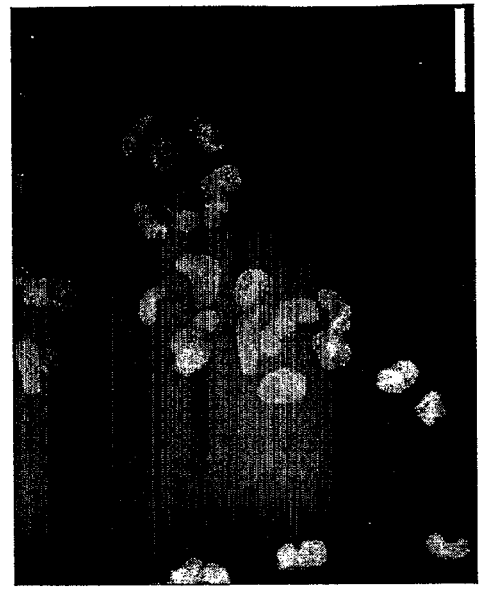

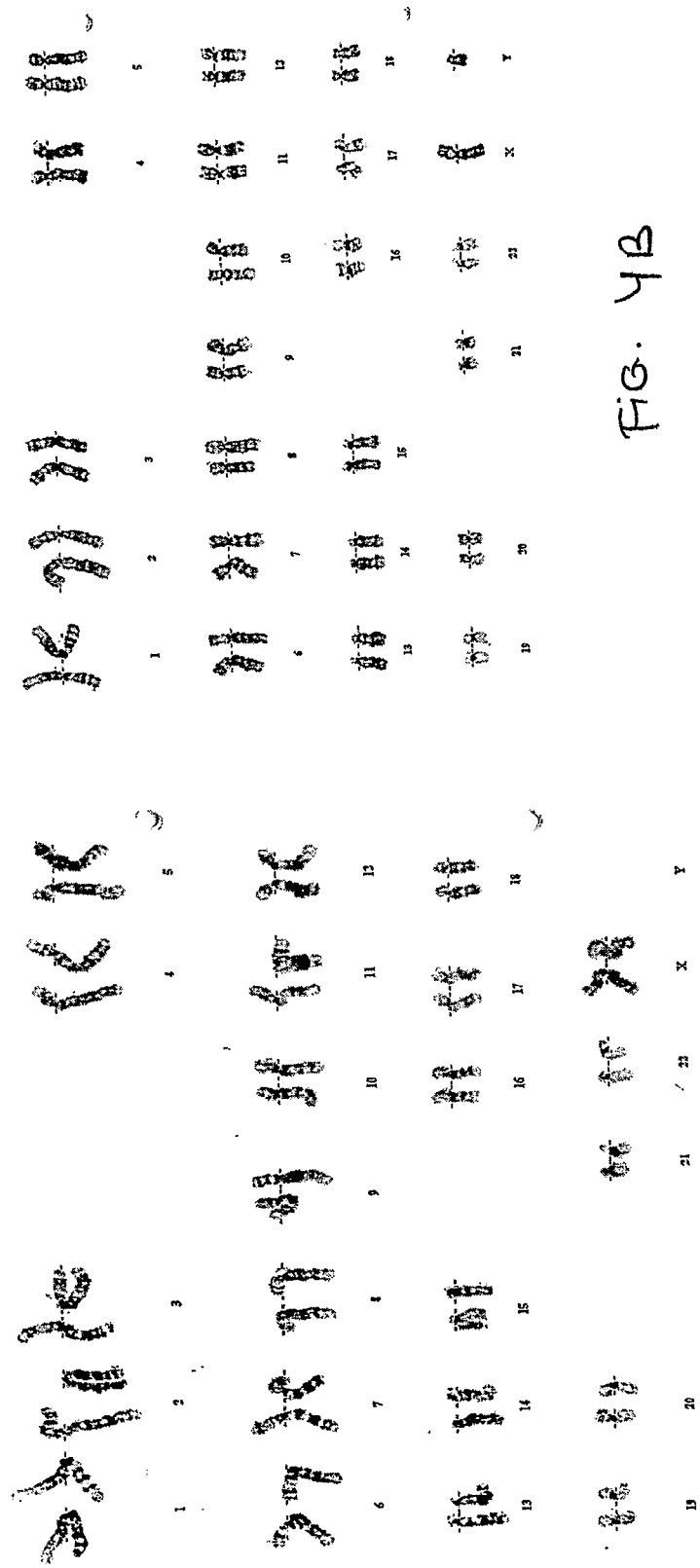

hES ON HEF1 hES ON FORESKIN (ORLA2)

PHASE hES ON CORD 1 3W

Fig. 7B hESC on cord1 — fluorescent
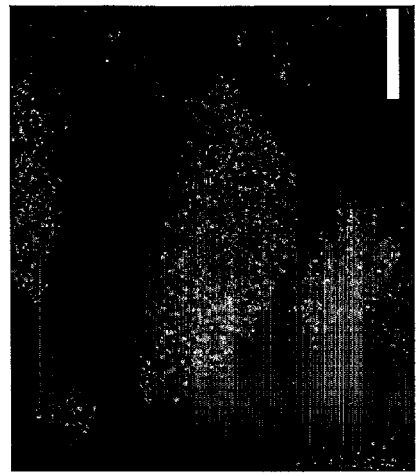
Fig. 7C hESC on HEF 2 — fluorescent
Fig. 7A hESC on foreskin (orla2) — dark field 3 week EB's in DMEM+15%-20% FCS

HEF

HEF

Neurospheres

HEF 3 week EB's in DMEM+15%-20% FCS

Foreskin

Foreskin

Neurospheres

Foreskin

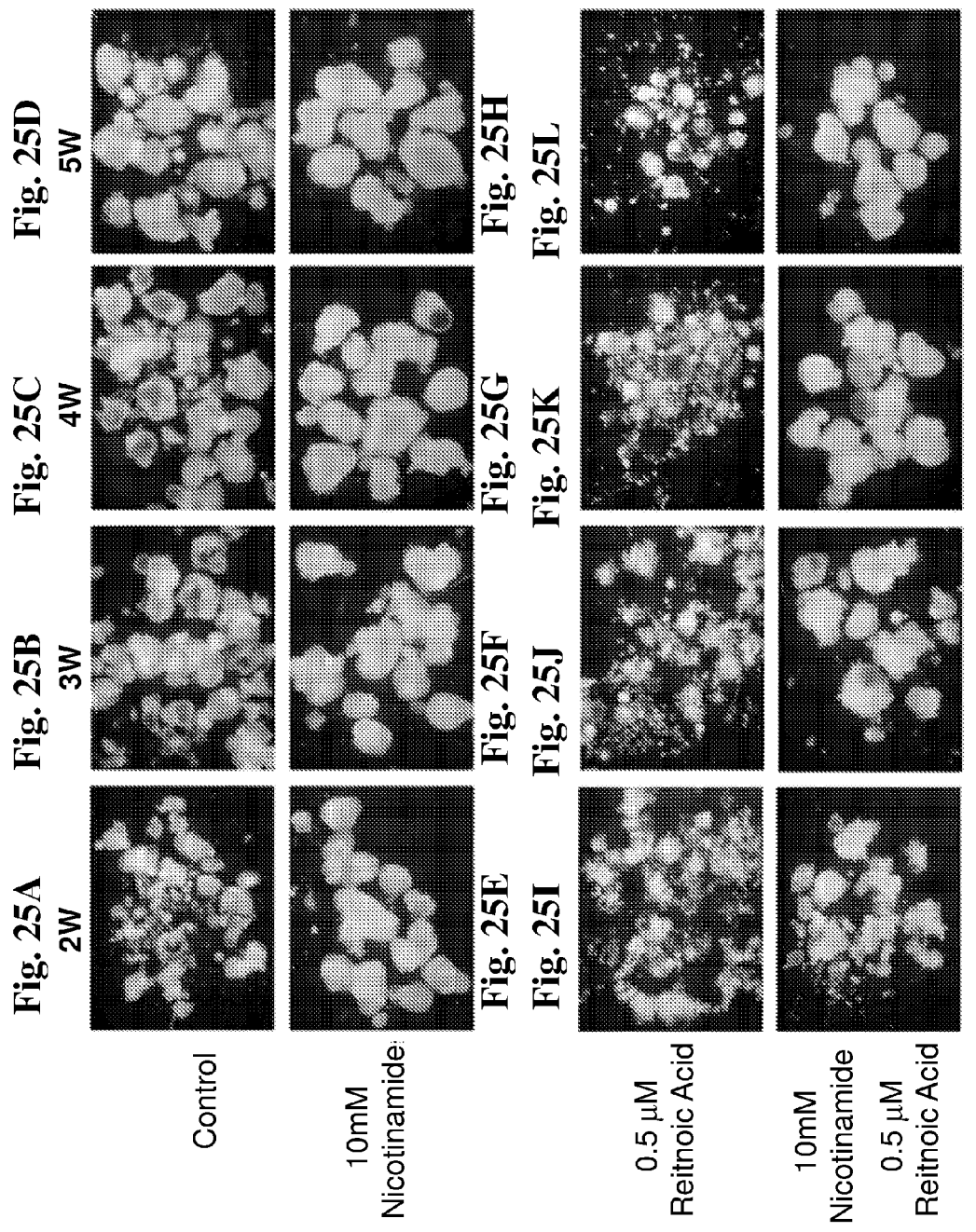

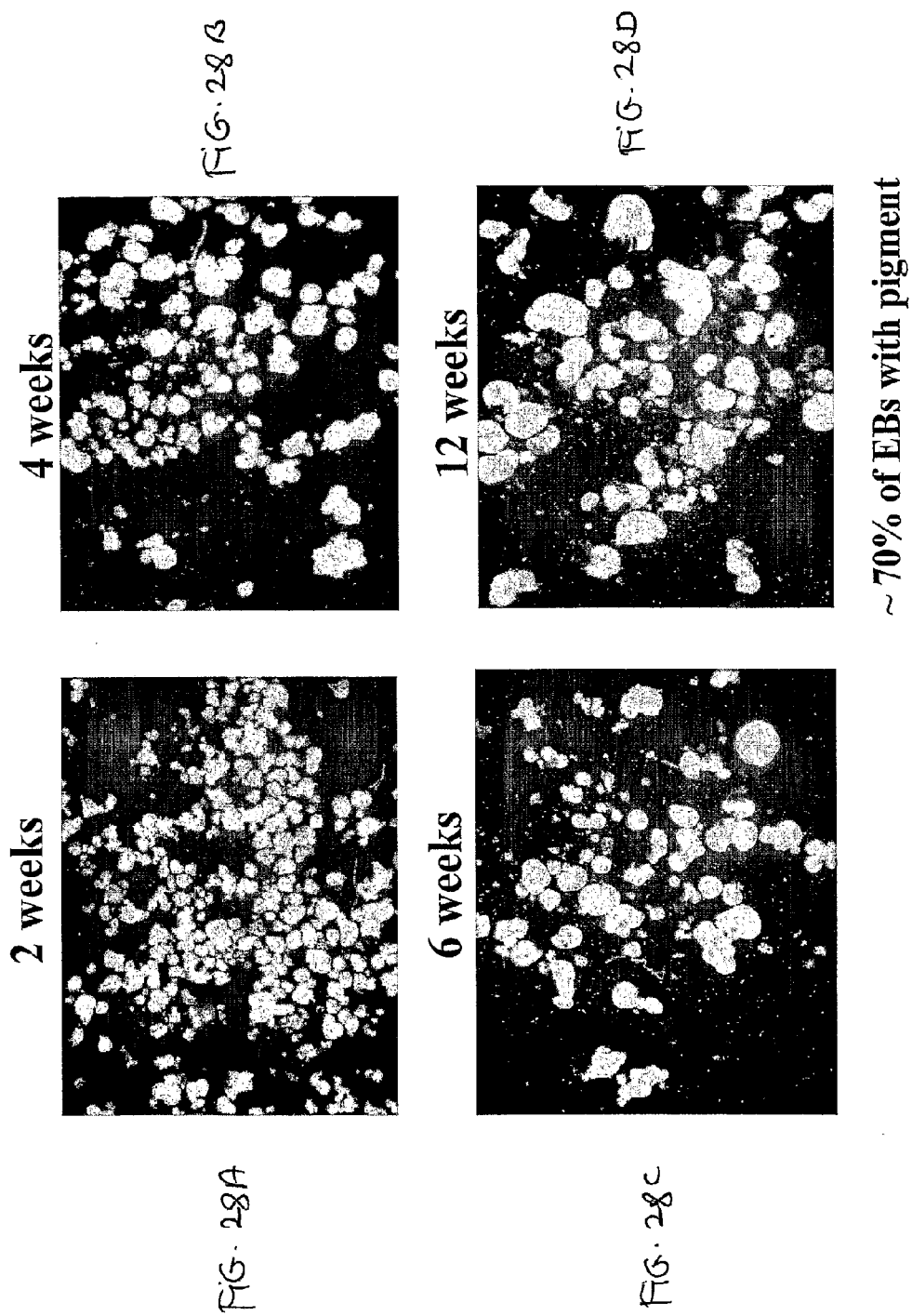
Figure 28. The time progression of melanin appearance. FIG. 28A 2 weeks; FIG. 28B 4 weeks; FIG. 28C 6 weeks; FIG. 28D 12 weeks, ~70% of EBs with pigment.

SEQUENCE LISTING

<160> NUMBER OF SEQ ID NOS: 4

<210> SEQ ID NO 1
<211> LENGTH: 20
<212> TYPE: DNA
<213> ORGANISM: Human

<400> SEQUENCE: 1
tgcaaggtgt gtccaggtaa                                                      20

<210> SEQ ID NO 2
<211> LENGTH: 20
<212> TYPE: DNA
<213> ORGANISM: Human

<400> SEQUENCE: 2
ccagcttgaa gtgaggaagc                                                      20

<210> SEQ ID NO 3
<211> LENGTH: 21
<212> TYPE: DNA
<213> ORGANISM: Human

<400> SEQUENCE: 3
ccatgtacat gagcactgtt g                                                    21

<210> SEQ ID NO 4
<211> LENGTH: 21
<212> TYPE: DNA
<213> ORGANISM: Human

<400> SEQUENCE: 4
ctccaataac tcctggtatc c                                                    21

STEM CELLS CULTURE SYSTEMS

This application is a Divisional Application filed under 35 U.S.C. 120 of U.S. patent application Ser. No. 11/794,262, filed on May 29, 2008, which was an application filed under 35 U.S.C. 371 as a national stage of PCT/IL2005/001397, filed on Dec. 29, 2005, which was an application claiming the benefit under 35 U.S.C. 119(e) of U.S. Provisional Application No. 60/639,809, filed on Dec. 29, 2004, the content of each of which is hereby incorporated by reference in its entirety.

FIELD OF THE INVENTION

The invention relates to stem cells (SC) in particularly to methods and systems for handling human embryonic stem cells (hESC).

LIST OF PRIOR ART

The following is a list of prior art, which is considered to be pertinent for describing the state of the art in the field of the invention.
(1) Thomson, J. A. et al. Embryonic stem cell lines derived from human blastocysts. Science 282, 1145-1147 (1998).
(2) Reubinoff, B. E., Pera, M. F., Fong, C. Y., Trounson, A. & Bongso, A. Embryonic stem cell lines from human blastocysts: somatic differentiation in vitro. Nat Biotechnol 18, 399-404 (2000)
(3) Amit, M. et al. Clonally derived human embryonic stem cell lines maintain pluripotency and proliferative potential for prolonged periods of culture. Dev Biol 227, 271-278 (2000).
(4) Xu, C. et al. Feeder-free growth of undifferentiated human embryonic stem cells. Nat Biotechnol 19, 971-974 (2001).
(5) Amit, M. et al. Human feeder layers for human embryonic stem cells. Biol Reprod 68, 2150-2156 (2003).
(6) Richards, M., Fong, C. Y., Chan, W. K., Wong, P. C. & Bongso, A. Human feeders support prolonged undifferentiated growth of human inner cell masses and embryonic stem cells. Nat Biotechnol 20, 933-936 (2002).
(7) Cowan, C. A. et al. Derivation of embryonic stem-cell lines from human blastocysts. N Engl J Med 350, 1353-1356 (2004).
(8) Amit, M., Shariki, C., Margulets, V. & Itskovitz-Eldor, J. Feeder layer- and Serum-Free Culture of Human Embryonic Stem Cells. Biol Reprod 70(3):837-45 (2004).
(9) Pera, M. F. et al. Regulation of human embryonic stem cell differentiation by BMP-2 and its antagonist noggin. J Cell Sci 117, 1269-1280 (2004).
(10) GB2409208.
(11) WO 04/031343
(12) Xu, R. H., et al. Basic FGF and suppression of BMP signaling sustain undifferentiated proliferation of human ES cells. Nat Methods. 3, 164-5 (2005)
(13) Vallier L, et al. Activin/Nodal and FGF pathways cooperate to maintain pluripotency of human embryonic stem cells. J Cell Sci. 118, 4495-509 (2005)

BACKGROUND OF THE INVENTION

Stem cells are immature, unspecialized cells that renew themselves for long periods through cell division. Under certain conditions, they can differentiate into mature, functional cells. Human embryonic stem cells (hESC) are derived from early surplus human blastocysts [1,2]. Human ES cells are unique stem cells since they can self-renew infinitely in culture, and since they have a remarkable potential to develop into extraembryonic lineages as well as all somatic cells and tissues of the human body [1,2].

Given the unique properties of hESC, they are expected to have far-reaching applications in the areas of basic scientific research, pharmacology, and regenerative medicine. Human ES cell lines can provide a powerful in vitro model for the study of the molecular and cellular biology of early human development, for functional genomics, drug screening, and discovery. They may serve for toxicology and teratogenicity high throughput screening. Since hESC can self-renew indefinitely and can differentiate into any cell type, they can serve as a renewable, unlimited donor source of functionally mature differentiated cells or tissues for transplantation therapy. In addition, transplanted genetically-modified hESC can serve as vectors to carry and express genes in target organs in the course of gene therapy.

While the promise of hESC for basic scientific research pharmacology and regenerative medicine is remarkable, the exploitation of hESC for most applications depends upon further development. Improved control of the growth of undifferentiated hESC, the development of bulk feeder-free cultures of undifferentiated cells, the development of animal-free culture systems, and the development of methods and tools which direct the differentiation and generate pure cultures of mature functional cells of a specific type are required.

At present, few culture systems are most commonly used to propagate undifferentiated hESC [1-4]. In the initial culture system that was developed, undifferentiated hESC are cultured in serum-containing medium as colonies, upon a layer of fibroblast feeder cells (of mouse [1,2] or human origin [5,11]). It is possible to remove all animal products from this culture system and replace them with those from a human source [6]. It was found that in this system the cells are propagated as clumps on a low scale which does not allow cloning.

An alternative culture system that was developed and used extensively is a serum-free system that includes the knockout (KO) medium supplemented with knockout serum replacement (KOSR) and FGF2. This system allows cloning of undifferentiated hESC, although at a low efficiency [3]. Undifferentiated cells are cultured as flat colonies and may be propagated as small clusters or single cells (by using trypsin [7]).

Another alternative culture system for use in the proliferation of undifferentiated growth of hESC comprises a culture matrix comprising extracellular matrix (ECM) prepared from feeder cells and a conditioned medium being preconditioned by feeder cells. The suggested leading cells in the feeder cells include primary mouse embryonic fibroblasts (PMEF) a mouse embryonic fibroblast cell line (MEF) murine foetal fibroblasts (MFF) human embryonic fibroblasts (HEF) human foetal muscle (HFM) human foetal skin cells (HFS) human adult skin cells, human foreskin fibroblasts (HFF) [10] human adult Fallopian tubal epithelial cells (HAFT) or human marrow stromal cells (HMSC).

Undifferentiated propagation may be accomplished with the KO serum-free culture system without the use of feeders by plating and growing colonies on extracellular matrices (ECM) within a feeder-conditioned KO medium supplemented with KOSR and FGF2 [4]. Furthermore, it has been suggested that feeder conditioning may be replaced by substituting the medium with high concentrations of FGF2 and noggin [12]. Alternatively, feeder conditioning was replaced by transforming growth factor β1 and human LIF (in addition to FGF2) and growing the cells on human fibronectin [8]. In a recent publication, undifferentiated propagation of hESC colonies, in the absence of feeders' was reported with a chemically defined medium without serum replacer, supplemented with activin or nodal plus FGF2[13].

A key limitation of hESC culture systems is that they do not allow the propagation of pure populations of undifferentiated stem cells and their use always involves some level of background differentiation. The stem cells most commonly follow a default pathway of differentiation into an epithelial cell type that grows either as a monolayer of flat squamous cells or form cystic structures. Most probably, this form of differentiation represents differentiation of hESC into extraembryonic endoderm[9].

Spontaneous differentiation of hESC into presumably extraembryonic lineages also interferes with the derivation of somatic differentiated cells. Under various differentiation-inducing conditions, such as in embryoid bodies (EB) suspension cultures, differentiation into cystic extraembryonic structures may be common or may predominate and limit differentiation into somatic lineages. Control and elimination of the differentiation into extraembryonic lineages therefore, may be invaluable in the derivation of somatic lineages, in addition to its importance in maintaining the stem cells in an undifferentiated state. It has been recently demonstrated that under differentiation-inducing culture conditions, the bone morphogenetic protein (BMP) antagonist noggin can prevent extraembryonic differentiation of hESC and promote their differentiation into the neural lineage[9].

SUMMARY OF THE INVENTION

In accordance with a first aspect, the present invention provides a cell culture comprising cells obtained from human umbilical cord tissue, the human umbilical cord derived cells being capable of maintaining stem cells (SC) in an undifferentiated state when co-cultured therewith. The human umbilical cord derived cells are preferably used as feeder cells in SC cultures.

The invention also provides a first culture system for maintenance of SC in an undifferentiated state, the culture system comprising feeder cells expanded from human umbilical cord cells, human embryonic fibroblast cells (HEF) and a combination of same. According to one preferred embodiment, the culture system comprises the human umbilical cord derived feeder cells of the invention.

Within this aspect of the invention there is also provided an undifferentiated pluripotent human embryonic SC culture obtained by incubating a cluster of cells from inside a blastocyst with the first culture system of the invention.

The invention also provides a method for maintaining SC in an undifferentiated state, the method comprising incubating said cells with a culture system comprising feeder cells expanded from human umbilical cord cells, human embryonic fibroblast cells (HEF) or a combination of same.

The use of feeder cells expanded from human umbilical cord derived cells, human embryonic fibroblast cells (HEF) and a combination of same for the preparation of a culture system for maintenance of SC in an undifferentiated state also forms part of the invention.

In accordance with a second aspect, the invention provides a further, second, culture system for inhibiting or preventing differentiation of SC to extraembryonic cells, the culture system comprising nicotinamide (NA) or a derivative of NA having an inhibitory effect on differentiation of stem cells to extraembryonic cells similar to that of NA.

A human embryonic SC culture essentially free of extraembryonic cells is also provided in the context of this aspect of the invention, the SC culture being obtained by incubating a cluster of cells from inside a blastocyst with a culture system comprising said NA or derivative thereof.

In accordance with this second aspect, there is also provided a method for inhibiting or preventing differentiation of stem cells to extraembryonic cells, the method comprises incubating said stem cells in a culture system comprising NA or a derivative of NA having an inhibitory effect on differentiation of stem cells to extraembryonic cells similar to that of NA.

Further in accordance with this aspect of the invention there is provided the use of NA or a NA derivative having an inhibitory effect on differentiation of to extraembryonic cells similar to that of NA for the preparation of a culture system for inhibiting or preventing differentiation of SC to extraembryonic cells.

In yet a third aspect of the invention there is provided a further, third, culture system, a humanized culture system for maintenance of SC in an undifferentiated state, the culture system comprising an animal free basic stem cell culture medium and humanized serum replacement substitute.

In accordance with this aspect there is also provided an undifferentiated human embryonic SC culture obtained by incubating a cluster of cells from inside a blastocyst with the humanized culture system comprising the animal free stem cell basic culture medium and a humanized serum replacement substitute.

In accordance with this aspect of the invention, there is also provided a method of maintaining stem cells in an undifferentiated state, the method comprises incubating said cells with a culture system comprising animal free stem cell basic culture medium and humanized serum replacement substitute.

In accordance with a fourth aspect of the invention there is provided a culture system for maintenance SC in an undifferentiated state, the culture system comprising Neurobasal™ medium.

Within this aspect there is also provided a culture of SC in an undifferentiated state, the SC culture being obtained by culturing a cluster of cells from inside a blastocyst with a culture system comprising Neurobasal™ medium.

In accordance with this aspect of the invention there is also provided a method for maintaining a culture of SC in an undifferentiated state, the method comprising incubating said cells with a culture system comprising Neurobasal™ medium as well as the use of Neurobasal™ medium for the preparation of a culture system for maintaining a suspension of stem cells in an undifferentiated state.

The SC may be maintained in the Neurobasal™-based culture system in the form of a suspension as well as in a monolayer (flat colonies). Preferably, the Neurobasal™ medium is supplemented with N2 supplement or an N2 like supplement as defined below.

Finally, there is provided in accordance with the invention a method of maintaining SC in an undifferentiated state comprising culturing SC with feeder cells expanded from human umbilical cord cells.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 2A-2F—are immunofluorscent images of umbilical cord foreskin, and human embryonic fibroblasts stained by anti-vimentin antibody (FIGS. 2A, 2C and 2E, respectively) and the corresponding DAPI nuclear counter staining (FIGS. 2B, 2D and 2F) showing that the human feeders express vimentin.

FIGS. 4A-4B—are representative analysis of one metaphase plate of human embryonic fibroblasts (FIG. 4A) and foreskin (FIG. 4B) showing that the human feeders have a normal karyotype.

FIG. 7A-7C—are immunofluorescent images of hES colonies expressing AP, when cultured on foreskin derived feeder cells (FIG. 7A), on umbilical cord derived feeder cells (FIG. 7B) and on human embryonic fibroblast cells (FIG. 7C).

FIGS. 25A-25P—are dark field micrographs of EBs that were cultured for 2-5 weeks in chemically-defined medium (NBN2) in the presence or absence of NA and retinoic acid as indicated. EBs with typical cystic structures (cystic EBs) developed in the absence of NA (FIGS. 25A-25D, i.e. upper panel). In the presence of NA, cystic formation was not observed, the EBs were comprised of tightly packed cells and were significantly larger (FIGS. 25E-25H, i.e. second panel). In the presence of RA, the EBs were smaller and included multiple cysts (FIGS. 25I-25L, i.e. third panel). NA blocked the effects of RA (FIGS. 25M-25P, i.e. lower panel).

FIG. 28A-28D—are dark field micrographs of EBs differentiating in the presence of NA showing that the percentage of EBs that included clusters of differentiated cells expressing melanin increased with time (FIGS. 28A, 28B, 28C and 28D representing results after 2, 4, 6 and 12, respectively).

DETAILED DESCRIPTION OF EXEMPLARY EMBODIMENTS

Figure 1B:
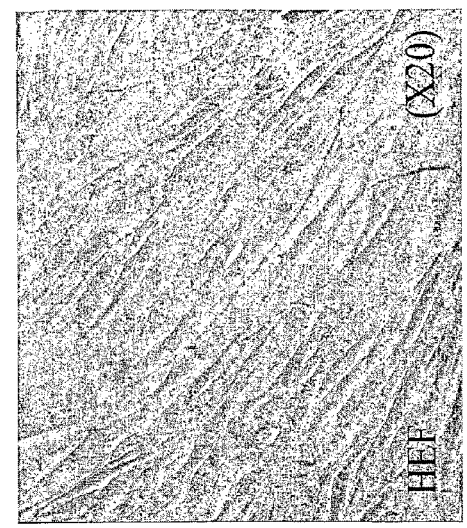
FIGS. 1A-1D—are phase contrast images of cord fibroblasts primary culture (FIG. 1A), human embryonic fibroblasts (FIG. 1B), fibroblasts derived from umbilical cord (FIG. 1C) and from foreskin (FIG. 1D).
Figure 1D:
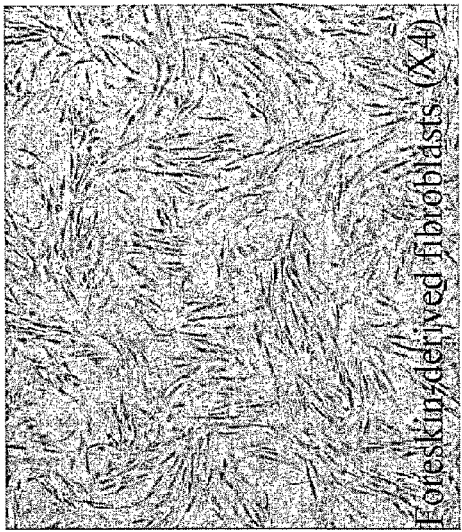

The invention is described in the following detailed description with reference to cell cultures and culture systems for handling stem cells, preferably human embryonic stem cells. It should be noted that in addition to the cell cultures and culture systems discussed in detailed hereinbelow, also encompassed within the present invention are uses of specific components described with reference to the culture system in the preparation of such culture systems as well as to methods of use of the culture system in handling stem cells cultures and methods of preparing culture cells.

As used in the specification and claims, the forms "a", "an" and "the" include singular as well as plural references unless the context clearly dictates otherwise. For example, the term "a culture system" includes one or more culture systems.

As used herein, the term "or" means one or a combination of two or more of the listed choices Further, as used herein, the term "comprising" is intended to mean that the methods or composition includes the recited elements, but not excluding others. Similarly, "consisting essentially of" is used to define methods and systems that include the recited elements but exclude other elements that may have an essential significance on the functionality of the culture systems of the inventions. For example, a culture system consisting essentially of a basic medium, medium supplements and feeder cells will not include or include only insignificant amounts (amounts that will have an insignificant effect on the propagation and differentiation of cells in the culture system) of other substances that have an effect on cells in a culture. Also, a composition consisting essentially of the elements as defined herein would not exclude trace contaminants from the isolation and purification method. "Consisting of" shall mean excluding more than trace elements of other elements. Embodiments defined by each of these transition terms are within the scope of this invention.

Further, all numerical values, e.g., concentration or dose or ranges thereof, are approximations which are varied (+) or (−) by up to 20%, at times by up to 10% of from the stated values. It is to be understood, even if not always explicitly stated that all numerical designations are preceded by the term "about". It also is to be understood, although not always explicitly stated, that the reagents described herein are merely exemplary and that equivalents of such are known in the art.

In its broadest sense, the present invention concerns culture cells, systems and methods for use of same in culturing of stem cells. As used herein, the term "stem cells" refers to cells which are capable of differentiating into other cell types having a particular, specialized function (i.e., "fully differentiated" cells) or self renewing and remaining in an undifferentiated pluripotential state as detailed below.

As used herein, the term "cell" refers to a single cell as well as to a population of (i.e. more than one) cells. The population may be a pure population comprising one cell type. Alternatively, the population may comprise more than one cell type. Furthermore, as used herein, the term "cell culture" refers to any in vitro culture of cells. Included within this term are continuous cell lines (e.g. with an immortal phenotype), primary cell cultures, finite cell lines (e.g., non-transformed cells), and any other cell population maintained in vitro.

As used herein, the term "primary cell" is a cell which is directly obtained from a tissue or organ of an animal, including a human, in the absence of culture. Typically, though not necessarily, a primary cell is capable of undergoing ten or fewer passages in vitro before senescence and/or cessation of proliferation. In contrast, a "cultured cell" is a cell which has been maintained and/or propagated in vitro for ten or more passages Non-limiting examples of stem cells are hematopoietic stem cells obtained from bone marrow tissue of an individual at any age or from cord blood of a newborn individual, embryonic stem (ES) cells obtained from the embryonic tissue formed after gestation (e.g., blastocyst), or embryonic germ (EG) cells obtained from the genital tissue of a fetus any time during gestation, preferably before 10 weeks of gestation. Preferred stem cells according to the present invention are human stem cells, more preferably, hESC.

Stem cells can be obtained using well-known cell-culture methods. For example, hESC can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 1-2 weeks. For further details on methods of preparation human ES cells see Thomson et al., [U.S. Pat. No. 5,843,780; Science 282:1145, 1998; Curr. Top. Dev. Biol. 38:133, 1998; Proc. Natl. Acad. Sci. USA 92: 7844, 1995]; as well as Bongso et al., [Hum Reprod 4: 706, 1989]; and Gardner et al., [Fertil. Steril. 69:84, 1998].

Commercially available stem cells can be also be used in accordance with the invention. Human ES cells can be purchased from the NIH human embryonic stem cells registry. Non-limiting examples of commercially available embryonic stem cell lines are BG01, BG02, BG03, BG04, CY12, CY30, CY92, CY10, TE03 and TE32.

Potential applications of hESC are far ranging and include drug discovery and testing, generation of cells, tissues and organs for use in transplantation, production of biomolecules, testing the toxicity and/or teratogenicity of compounds and facilitating the study of developmental and other biological processes. For example, diseases presently expected to be treatable by therapeutic transplantation of hESC or hESC derived cells include Parkinson's disease, cardiac infarcts, juvenile-onset diabetes mellitus, and leukemia [Gearhart J. Science 282: 1061-1062, 1998; Rossant and Nagy, Nature Biotech. 17: 23-24, 1999].

There are, however, significant hurdles to the practical exploitation of hESC. To maintain hESC in an undifferentiated pluripotential state, the cells are usually cultured on feeder cells. The feeder cells can secrete factors needed for stem cell self-renewal and proliferation, while at the same time, inhibit their differentiation.

Commonly used feeder cells includes a primary mouse embryonic fibroblast (PMEF), a mouse embryonic fibroblast (MEF), a murine fetal fibroblast (MFF), a human embryonic fibroblast (HEF), a human fetal muscle cell (HFM), a human fetal skin cell (HFS), a human adult skin cell, a human foreskin fibroblast (HFF), a human adult fallopian tubal epithelial cell (HAFT) and a human marrow stromal cells (hMSCs).

As used herein, the term "undifferentiated pluripotential hES cells" or "hESC" refers to human precursor cells that have the ability to form any adult cell. Such cells are true cell lines in that they (i) are capable of indefinite proliferation in vitro in an undifferentiated state; and (ii) are capable of differentiation to derivatives of all three embryonic germ layers (endoderm, mesoderm, and ectoderm) even after prolonged culture. Human ES cells are derived from fertilized embryos that are less than one week old.

Pluripotent SC present at their surface or express biological markers which are used to identify pluripotent SC as well as to verify that the cells in the culture are maintained in an undifferentiated state [Thomson J A et al. Embryonic Stem Cell Lines Derived from Human Blastocysts Science 282 (5391):1145-1147 (1998)]. A non-limiting list of such cell markers comprise stage-specific embryonic antigen such as SSEA-3, SSEA-4; antibodies to specific extracellular matrix molecule which are synthesized by undifferentiated pluripotent SC, such as TRA-1-60, TRA-1-81 and GCTM-2; elevated expression of alkaline phosphatase which is associated with undifferentiated pluripotent SC; transcription factors unique to pluripotent SC and which are essential for establishment and maintenance of undifferentiated SC, such as, OCT-4 and Genesis [Carpenter, m. k., Rosler, E., Rao M. S., Characterization and Differentiation of Human Embryonic Stem Cells. Cloning and Stem Cells 5, 79-88, 2003].

While widely used, human SC cultures based on murine derived feeder cells, are less desired. Non-species specific feeder cell technology reduces the value of stem cell cultures due to the foreign nature of the source of the feeder cell. For example, such non-species specific feeder cells contain both foreign cells and foreign growth factors. Further, it is believed that the use of non-species specific feeder cells in combination with different but desirable cultured cells cannot provide the optimum growth conditions as species specific derived feeder cells or conditioned media. The issue of cross-species contamination is particularly relevant to agricultural animals, endangered species, laboratory animals, non-human primate cells, and hESC. It has been shown that hESC are contaminated by foreign molecules when cultured with mouse-derived feeders (Martin, M. J., et al., Human embryonic stem cells express an immunogenic nonhuman sialic acid. Nat Med. 2005; 11: 228-32). Contamination of hESC by mouse derived molecules/pathogens may interfere with their exploitation as a model for basic research and raises concerns as to their use in transplantation therapy. Still further, non-human feeder cell technology reduces the value of human derived SC cultures, as, for example, such non-human feeder cells contain both non-human cells and non-human growth factors. Also, it is believe that the use of non-human feeder cells in combination with human cultured cells cannot provide the optimum growth conditions as human derived feeder cells.

Thus, the present invention provides, in accordance with a first of its aspects, a cell culture derived from human umbilical cord tissue, preferably excluding hematopoietic tissue, and being capable of maintaining SC in an undifferentiated state when co-cultured therewith. These feeder cells are obtained from culturing, preferably in an animal free culture system, of cells taken from umbilical cord tissue under conditions which allow the cells to propagate/expand and isolating the thereby propagated cells. The cells in the culture are essentially fibroblast cells and are preferably used as feeders in stem cell culture systems.

The cell cultures (either the feeder cells or the SC cultures) in accordance with the invention may be a fresh cell culture, cryopreserved culture as well as cryopreserved and thawed cells.

As used herein, the term "derived" which may be used interchangeably with the term "obtained" when used in the context of cell formation denotes the development of a new cell line from another cell line. For example, human embryonic cord derived cells denote, in accordance with one embodiment of the invention, fibroblast cells originating from embryonic cord tissue, which under suitable condition propagate into a fibroblast cell line.

Further, as used herein, the term "feeder cells" which is known interchangeably with "feeders" denotes any type of cells which may be used as a substratum for other cells attachment and growth in a culture system. Feeder cells are typically used to allow growth and survival of single undifferentiated stem cells. The Feeder cells provide conditions that maintain cell proliferation, inhibit cell differentiation and preserve pluripotency. Specifically, the feeder cells are cells that secrete factors needed for stem cell proliferation, while inhibit their differentiation. Methods of preparing feeder cells are well known in the art (see, for example, U.S. patent Pub. No. 20030143736). Generally, the feeder cells may be fibroblasts or other types of cells, and the cells are inactivated by large-dose radiation before use, such as γ-ray, or by drugs, such as mitomycin C. After the inactivation process, the surviving cells lost the capability to proliferate, but retained their physiological functions, such as metabolism and synthesis of growth factors.

As indicated above, the feeder cells are derived (expanded) from umbilical cord tissue. Umbilical cord tissue may be obtained in the course of vaginal delivery. However, a major advantage of using umbilical cord tissue is that it may be obtained during elective cesarean section in a sterile environment of an operating theater. Moreover, the umbilical cord is obtained from the sterile environment of the amniotic sac and has not been exposed to any external contagious agents prior to donation. The sterile nature of umbilical cord donation allows the derivation of feeders from the umbilical cord tissue without the use of antibiotics or anti-fungal drugs. Avoiding the use of anti-bacterial and anti-fungal drugs is an advantage since these drugs may interfere with the growth of cells in culture, alter the results of basic science studies and most importantly may induce allergic reactions in recipients of cells that were cultured in the presence of these drugs. Derivation of feeders from other human primary tissues such as foreskin or aborted fetuses are done under significant less sterile conditions. The foreskin is exposed to bacteria that colonize the genital area and it may be disinfected but not sterilized. Aborted fetuses are also exposed to potential contamination by vaginal and genital flora during dilatation and curettage.

An additional advantage of umbilical cord as opposed to foreskin or human fetal tissues is that a significant volume of blood may be sampled from the umbilical cord, tested for contagious agents and archived. This is not possible with foreskin tissues donated by newborn babies or with aborted fetuses. Lastly, umbilical cord is routinely discarded and its donation is not associated with emotional or moral constrains, while donation of fetal tissues raises ethical concerns and is not morally accepted by many.

In this connection there is thus also provided a method for preparing umbilical cord derived feeder cells, the method comprising isolating umbilical cord cells from umbilical cord tissue and culturing said umbilical cord cells in a culture medium including serum, thereby preparing said human umbilical cord feeder cells. The umbilical cord cells may be isolated from the umbilical cord tissue by mincing the tissue and affixing the umbilical cord to a wall, such as a wall of a flask, and allowing the cells to incubate undisturbed for a number of weeks until fibroblast cells begin to migrate out of the minced umbilical cord tissue.

The umbilical cord tissue may be obtained from healthy pregnant women undergoing elective Cesarean sections at term.

In accordance with the invention there is also provided a culture system for maintaining stem cells (SC) in an undifferentiated state, the culture system comprising feeder cells selected from cells obtained from human umbilical cord tissue (excluding cells obtained from umbilical cord blood), human embryonic fibroblast cells (HEF) or a combination of same. The culture system according to this aspect of the invention is term herein the "human derived feeder cell aspect of the invention".

As used herein with respect to all aspects of the invention, the terms "maintenance" means continued survival of a cell or population of cells, at times, with an increase in numbers of cells. "Proliferation", "propagation", "expansion" and "growth", which are used interchangeably, refer to such an increase in cell number. According to one embodiment, when referring to maintenance of hESC on feeder cells, this term refers to a continuous survival of the cells for at least 10 weeks.

The culture systems in accordance with the invention are preferably for enabling maintenance of a population of stem cells when cultured on feeder cells, and at time, propagation of same, for a prolonged period of time, the period of time being at least 10 weeks.

When the feeder cells are derived from human umbilical cord tissue, the feeder cells are essentially fibroblast cells. The term "essentially fibroblast cells" denotes that the feeder cells comprise in its majority fibroblasts, i.e. at least 70 of the cells in the feeder cell population are fibroblast, preferably 85%, a most preferably all the cells, i.e. essentially 100% of the feeder cells are fibroblasts.

In accordance with one embodiment, the feeder cells are provided in a form of a monolayer coated culture dish to which a nutrient medium is added along with the culture cells. As used herein, the terms "monolayer", "monolayer culture" and "monolayer cell culture" refer to cells that have adhered to a substrate and grow as a layer that is one cell in thickness. Monolayer cells may be grown in any format, including but not limited to flasks, tubes, coverslips (e.g., shell vials), roller bottles, etc. Monolayer cells may also be grown attached to microcarriers, including but not limited to beads. At times, the term monolayer also includes growth of cells as flat colonies.

The term "culture system" denotes a combination of elements, such as an extracellular matrix (ECM) and a culture (nutrient) medium which together provide suitable conditions that support SC growth. The conditions are such that SC can proceed through the cell cycle, grow and divide. Preferably, the conditions are such which enable growth of human stem cells, preferably, hESC. Further, the culture system provides conditions that permit the embryonic stem cells to stably proliferate in the culture system for at least 10 weeks. The nutrient medium may contain any of the following appropriate combinations: a basic medium (a cell culture medium usually comprising a defined base solution, which includes salts, sugars and amino acids) as well as serum or serum replacement, and other exogenously added factors. It is not intended that the term "culture medium" or "nutrient medium" be limited to any particular culture medium. For example, it is intended that the definition encompass outgrowth as well as maintenance media. In accordance with the human derived feeder cell aspect of the invention, the culture system also comprises the feeder cells. However, the feeder cells may be substituted with components derived from feeder cells or other known and acceptable substitutes thereof, e.g. when referring to other culture systems disclosed herein.

In accordance with one embodiment, the culture system is employed for maintaining hESC in an undifferentiated pluripotential state, as evidenced in the following non-limiting examples by the expression of proteins such as SSEA-4, TRA-1-60, OCT-4, APase, but not SSEA-1. Methods of preparing culture systems for culturing hESC are well known in the art [see, for example, Reubinoff Be. et. al., *Nat. Biotechnol.* 18:399-404, 2002; Richards, M. et al., *Nat. Biotechnol.* 20:933-936, 2002].

A hESC medium may typically contain 80% Dulbecco's Modified Eagles Medium (DMEM), 20% defined Fetal Calf Serum, 1% L-Glutamine, 0.5% penicillin/streptomycin, 1% non-essential amino acids, 1% Insulin-Transferrin-Selenium G supplement and 1 mM β-mercaptoethanol.

In an animal free culture system, which provides a pathogen-free environment for the growth of ES cells, the cultures rely on human feeder layers supplemented with human serum or serum replacement suitable for the growth of human stem cells. The feeder cells may be any suitable cells from human source as known in the art or the isolated umbilical cord derived feeder cells of the invention; the stem cells medium DMEM (used as the basic media) may be replaced with KO DMEM (Gibco, or equivalent), X-Vivo 10 (Biowhittaker, Maryland, or equivalent) or Cellgro Stem Cell Growth Medium (CellGenix, Freiburg, Germany, or equivalent); the FCS may be replaced with humanized serum replacement substitute, such as TCH (Protide Pharmaceuticals, St. Paul, Minn., or equivalent) or Nutridoma-CS (Roche, Germany, or equivalent). Since the animal free system provides a pathogen free environment, reducing agents such as β-mercaptoethanol and antibacterial agents such as penicillin/streptomycin) may be eliminated.

In the context of the human derived feeder cell culture system aspect of the invention there is also provided a method for maintaining stem cells in an undifferentiated state, the method comprises incubating (co-culturing) said cells with a culture system comprising feeder cells selected from human umbilical cord tissue derived cells, human embryonic fibroblast cells (HEF) or a combination of same.

According to one embodiment, the stem cells are incubated in a culture system where the feeder cells are preferably provided as a layer of cells, preferably a mono-layer, formed on a base of culture dish. The culture system is then provided with a growth environment, typically, an environment in which cells of interest will proliferate in vitro. Temperatures of 37° C. and 5% $CO_2$ in air are generally adopted.

In cultures of undifferentiated hESCs there is always some level of background extraembryonic differentiation. Further, in currently-used systems for the cultivation of undifferentiated hESCs, or for induction of their differentiation towards somatic lineages, three is tendency of hESCs to differentiate towards extraembryonic lineages. In addition, upon induction of differentiation, the default pathway of differentiation towards extraembryonic lineages may predominate, and limit differentiation into desired somatic lineages.

Thus, the invention also provides a culture system for inhibiting or preventing differentiation of stem cells towards extraembryonic lineages (to extraembryonic cells). The culture system in accordance with this aspect of the invention comprise NA (NA) or a derivative of NA having an inhibitory effect on differentiation of stem cells towards extraembryonic lineages (to extraembryonic cells) similar to that of NA. This aspect of the invention is referred to herein as the "nicotinamide aspect of the invention".

NA is a form of Vitamin B3 that may preserve and improve beta cell function. NA is essential for growth and conversion of foods to energy and it has been used in diabetes treatment and prevention. It has now been found that NA is capable of inhibiting, preferably, preventing differentiation of embryonic stem cells towards extraembryonic lineages (to extraembryonic cells).

The term "derivative of nicotinamide" as used herein denotes a compound which is a chemical modification of the natural NA.

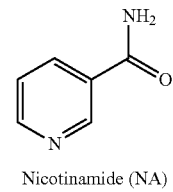

Nicotinamide (NA)

The chemical modification may include substitution on the pyridine ring of the basic NA structure (via the carbon or nitrogen member of the ring), via the nitrogen or the oxygen atoms of the amide moiety, as well as deletion or replacement of a group, e.g. to form a thiobenzamide analog of NA, all of which being as appreciated by those versed in organic chemistry. The derivative in the context of the invention also includes the nucleoside derivative of NA (e.g. nicotinamide adenine). A variety of NA derivatives are described, some also in connection with an inhibitory activity of the PDE4 enzyme [WO03068233; WO02060875; GB2327675A], or as VEGF-receptor tyrosine kinase inhibitors [WO01/55114]. For example, the process of preparing 4-aryl-nicotinamide derivatives are described in WO05014549A. The NA derivatives in the context of the invention are compound determined to have an inhibitory effect, preferably preventative effect, on differentiation of stem cells to extraembryonic lineages (extraembryonic cells), similar to that of NA.

The effect of NA may be the result of inhibition of poly (ADP-ribose) polymerase (PARP). Therefore the effect of NA may be also achieved by treating the cells with other PARP inhibitors such as 3-aminobenzmide, PJ-34 or 1, 5-dihydroxyisoquinoline. These other PARP inhibitors are also included in the context of the term "modification of NA". Yet further, the effect of NA may also be attributed to the inhibition of SIRT protein deacetylase. Therefore its effect may be also obtained by other SIRT inhibitors such as splitomicin and sirtinol, which are thus, also included in the context of the term "modification of NA".

In accordance with the NA aspect of the invention, the stem cells may be as described above, i.e. they may be stem cells from any source, but are preferably human stem cells, further preferably, human embryonic stem cells.

As used herein "inhibition of extraembryonic differentiation" used synonymy with the term "prevention of extraembryonic differentiation" denotes the maintenance as well as the expansion of embryonic stem cell in a cell culture and that the resulting cell culture is essentially free of extraembryonic cells or membranes. The term "essentially free" is used to exclude extraembryonic cells that may have an essential significance on the functionality of the stem or somatic cells in the culture or that the amount of the extraembryonic cells in the cell culture is insignificant (an amount that will have an insignificant effect on the propagation and differentiation of cells in the culture system).

It is well appreciated that if extraembryonic differentiation is essentially eliminated, a key challenge is to further direct differentiation into a specific somatic lineage and into a specific type of cell. It has now been found that supplementation of a culture medium with NA can prevent the default differentiation of hESCs towards extraembryonic lineages. It may also direct the differentiation towards specific somatic lineage such as but not limited to neural differentiation. The examples provided herein show differentiation to neural precursor cells.

Proliferation and differentiation of embryonic stem cells into insulin-producing cells in the presence of NA was suggested by Vaca P. et al, [Transplant Proc. 35(5):2021-3 2003] Specifically, it was shown that while proliferation within EBs with or without supplementation of the medium with NA is similar (FIG. 1A in Vaca P. et al.), insulin content is increased in cells that differentiate in the presence of NA. Nevertheless it is unclear whether the increased insulin content was not related to increased uptake of insulin from the medium.

It has now been found that NA effectively induced differentiation of stem cells into somatic cells. Specifically, albeit, not exclusively, NA was shown to induce differentiation to neural cells, and within the neural lineage, NA treatment was found to promote differentiation towards retinal pigmented epithelial (RPE) cells. The use of RPE cells in transplantation has already been described [Haruta, M. et al., In vitro and in vivo characterization of pigment epithelial cells differentiated from primate embryonic stem cells. *Invest Ophthalmol Vis Sci*, 45:1020-1025 (2004)]. Thus, it is to be understood that the RPE cells obtained in accordance with the present invention have various therapeutic applications. One such application includes transplantation of such cells in the eye to replenish malfunctioning or degenerated RPE cells in retinal degenerations. Genetically modified RPE cells may serve as a vector to carry and express genes in the retina after transplantation. Other applications may be the use of hESC-derived RPE cells as an in vitro model for the development of new drugs to promote RPE survival and function. hESC-derived RPE cells may serve for high throughput screening for compounds that are toxic, trophic, induce differentiation proliferation and survival of RPE cells. They may be used to uncover mechanisms, new genes, soluble or membrane-bound factors that are important for the development, differentiation, maintenance, survival and function of photoreceptor cells.

The culture system in the NA aspect of the invention comprises standard elements of culture media, as defined above combined with NA. The concentration of NA in the medium may vary, however, will preferably be in a concentration range between about 1 mM to about 20 mM, more preferably at a concentration of about 10 mM.

In the context of this aspect of the invention there is also provided a method for inhibiting or preventing differentiation of stem cells towards extraembryonic lineages (to extraembryonic cells), the method comprises incubating said stem cells in a culture system comprising NA or a derivative of NA as defined above.

It should be noted that in the context of the present invention the NA based culture systems was also effective for increasing the survival of SC in the culture system. According to one embodiment, cells survived in the culture for at least 12 weeks.

It should also be noted that the NA based culture system of the invention was effective to induces an increase in number of cells within embryoid bodies (EB) cultured therein.

For induction of somatic differentiation, the stem cells in accordance with the NA aspect of the invention are preferably grown as free floating clusters in a suspension. As used herein, the terms "suspension" and "suspension culture" refer to cells that survive and proliferate without being attached to a substrate.

A further aspect of the invention concerns the use of serum (e.g., fetal bovine serum (FBS)), in SC cultures. It has already been established that serum is a major source of undefined differentiation factors and thus tends to promote ES cell differentiation. Other problems are also associated with serum. Lot-to-lot variation is often observed and some lots of serum have been found to be toxic to cells [Robertson, E. J., ed., Teratocarcinomas and Embryonic Stem Cells: A Practical Approach, IRL Press, Oxford, UK (1987)]. Moreover, serum may be contaminated with infectious agents such as mycoplasma, bacteriophage, and viruses. Finally, because serum is an undefined and variable component of any medium, the use of serum prevents the true definition and elucidation of the nutritional and hormonal requirements of the cultured cells.

It has now been found that the use of two well known and commercially available humanized serum replacement (SR) substitutes, which have not been used hitherto in human embryonic stem cell technology, i.e. TCH™ (Protide Pharmaceuticals, St. Paul, Minn., or equivalent) and Nutridoma-CS (Roche, Germany, or equivalent) used as serum replacement substitute, did not impair the undifferentiated propagation of the stem cells in the culture system.

Thus, according to a further aspect, the invention also provide a humanized culture system for maintenance of stem cells (SC) in an undifferentiated state, the humanized culture system comprising animal free stem cell basic medium and a humanized serum replacement substitute. This aspect of the invention is referred to as the "humanized serum free culture system of the invention".

In accordance with one embodiment, the humanized culture system comprises a serum free basic medium as known to those versed in the art of stem cells (i.e. a medium which is free of animal origin and is suitable for growth of stem cells), selected from Cellgro Stem Cell Growth Medium, KO DMEM, Neurobasal™, or X-Vivo 10.

In accordance with another embodiment, the humanized culture system comprises a serum replacement substituent selected from TCH™, Nutridoma-CS or combination of same.

In accordance with yet another embodiment, when said serum free basic medium is Neurobasal™, the culture system further comprises N2 supplement [GIBCO® Cell Culture] or a modified N2 supplement, the modification rendering the medium supplement suitable for use with stem cells. It is noted that the standard and commercially available N2 supplement comprises insulin, transferrin, progesterone, putrascine, selenite. The specific composition of N2 supplement as published by StemCell Technologies Inc (Product Information Sheet, revised on December 2002) includes 2.5 mg/mL rh insulin, 10 mg/mL human transferring (which may be iron-poor or iron-saturated), 0.52 µg/mL sodium selenite, 1.61 mg/mL putrascine, 0.63 µg/mL progesterone, all in phosphate buffered saline. Nonetheless, modifications of the standard N2 supplement for stem cells maintenance are readily envisaged by those versed in the art. For example, medium for the propagation of ESC-derived neural stem cells is supplemented with modified N2 [Conti, L, et al., Niche-independent symmetrical self-renewal of a mammalian tissue stem cell. PLoS Biol. 9:e283 (2005)].

TCH™ is a completely biochemically defined serum replacement developed primarily for human cells and production of cell-secreted proteins. TCH™ may be purchased from Protide Pharmaceuticals (MN, USA) as well as from BM Biomedicals (CA, USA).

Nutridoma-CS is also a completely biochemically defined serum free medium supplement composed of albumin, insulin, transferrin, cytokines a cholesterol source and other defined organic and inorganic compounds.

The use of humanized SR as suggested herein in combination with serum free basic mediums thus enables the providence of an animal free and humanized culture system for maintenance as well as expansion of undifferentiated SC, preferably human SC, more preferably, hESC. The culture system may comprise, in addition to the humanized SR, human derived feeder cells such as that disclosed above (as well as those known in the art), The amount of the humanized SR may vary and will depend on other elements forming part of the culture system. Those versed in the art will know how to manipulate the concentrations of SR in the culture system to facilitate maintenance of the stem cells cultured therewith. According to one embodiment, 2% TCH may be used. However, higher or lower concentrations of TCH may be used.

According to the humanized SR aspect of the invention there is also provided the use of humanized serum replacement substitute selected from TCH™, Nutridoma-CS or combination of same for the preparation of a culture system for maintaining stem cells, preferably human embryonic stem cells, in an undifferentiated state. According to one embodiment, the cells are co-cultured with feeder cells, preferably human derived feeder cells.

Figure 21:
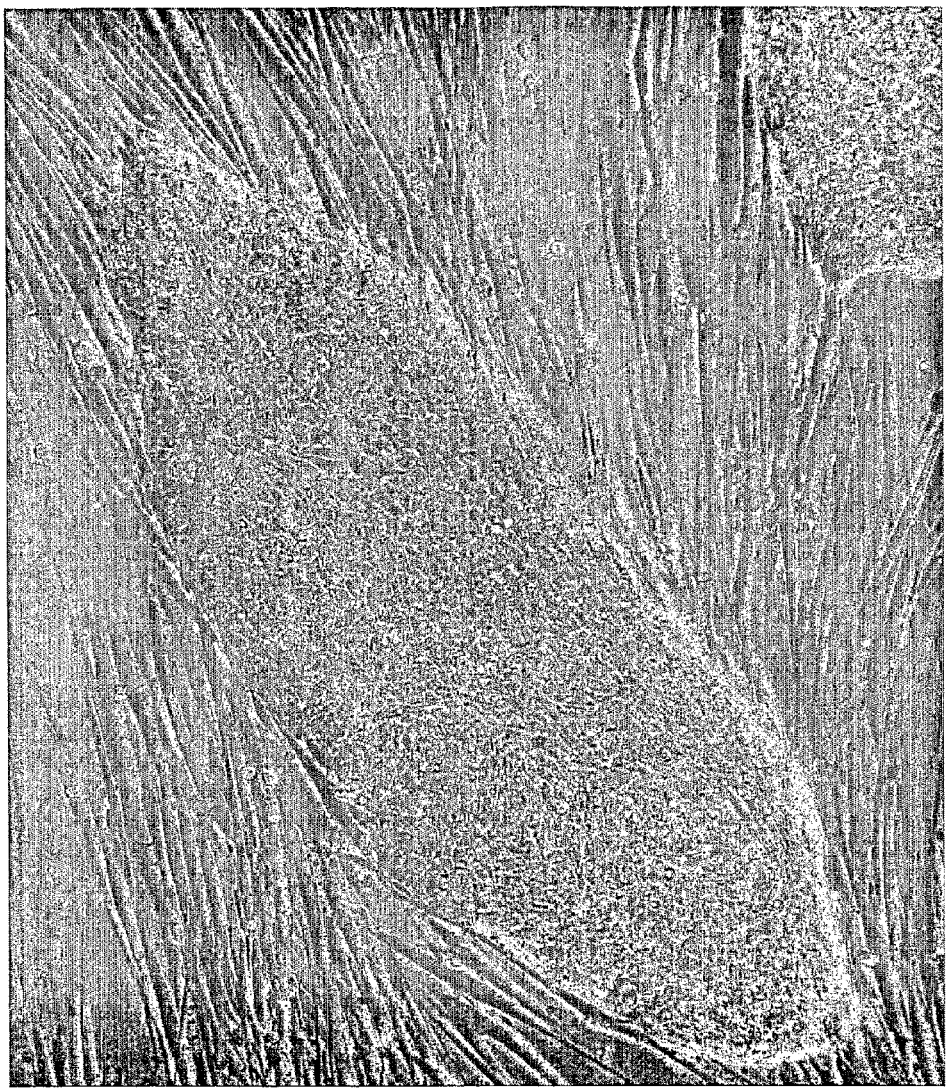
FIG. 21—is a phase contrast micrograph of hESC colonies cultured within NBN2 showing that hESCS retain the morphology of undifferentiated cells when colonies are cultivated on human feeders in NBN2.

Finally, the invention provides a further culture system for maintaining a stem cells, preferably human, more preferably, hESC, in an undifferentiated state, the culture system comprising Neurobasal™ medium. According to one embodiment, the Neurobasal™ is supplemented with N2 supplement or a modification of N2 supplement (as defined above) for a humanized flat culture system of hESC on feeders (see for example FIG. 21) as well as for maintenance of stem cells in suspensions (see for example FIG. 22). Neurobasal™ is known in the art of cell cultures [Brewer G J. Serum-free B27/Neurobasal medium supports differential growth of neurons from the striatum, substantia nigra, septum, cerebral cortex, J Neurosci Res. 42(5):674-83, (1995)] and is commercially available [Gibco, Invitrogen cell culture, USA]. This aspect is referred to herein as the "Neurobasal™ based culture aspect of the invention".

As indicated above, and in accordance with one embodiment of this aspect of the invention the culture system is supplemented with N2 supplement, a chemically-defined additive for Neurobasal™ Media.

Additional culture elements may be added, such as an extra cellular matrix (ECM) which is a complex structural (network like) entity surrounding and supporting cells, composed of different combinations of the following three major classes of bio-molecules:

Structural proteins: collagen and elastin.
Specialized proteins: e.g. fibrillin, fibronectin, and laminin.
Proteoglycans: conjugates of a protein core and glycosaminoglycans (GAGs).

Figure 23A:
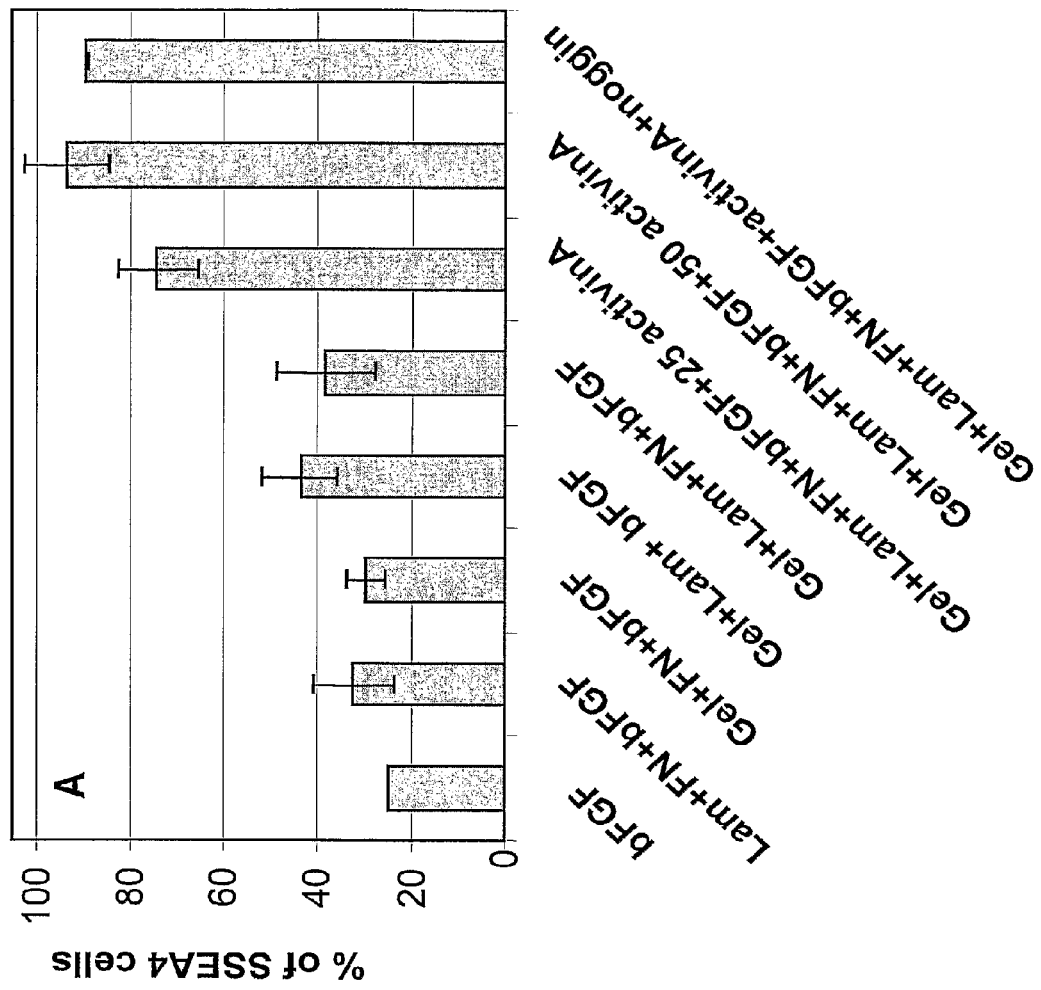
FIG. 23A-23B—are bar graphs showing the percentage of SSEA-4+cells (FIG. 23A) and total number of cell/well (FIG. 23B) as analyzed after 3 weeks suspension culture of equal initial numbers of hESC in NBN2 medium+FGF2 supplemented with various combinations of ECM components and factors.
Figure 23B:
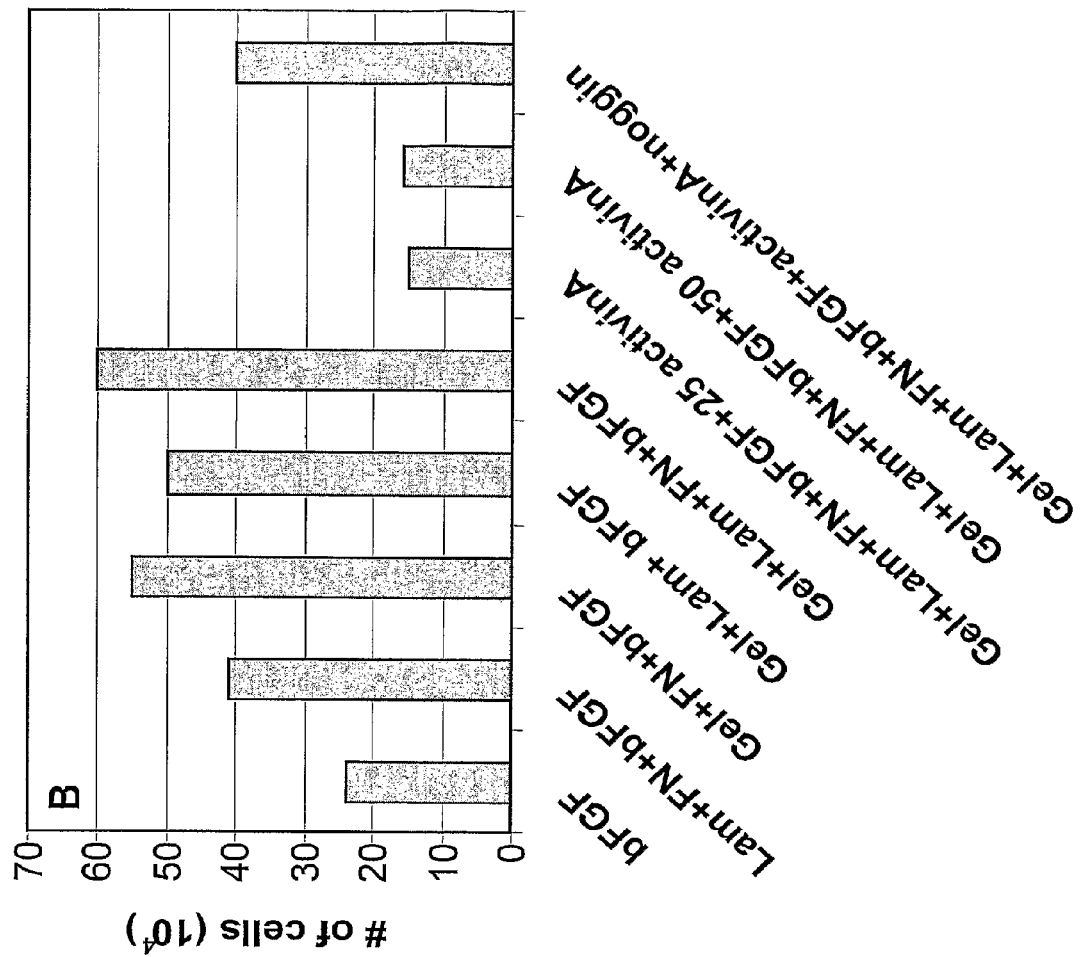

Further additional elements may include growth factors, for example, without being limited thereto, FGF (e.g. FGF2) as well as others known in the art (see also FIGS. 23A and 23B).

Yet, additional elements which may be added include noggin and activin A, as familiar to those versed in the art of stem cells.

As appreciated by those versed in the art and also indicated herein, there are some advantages in growing cells in suspensions. For example, to exploit the potential of hESC for high throughput screening, drug discovery, basic research, regenerative medicine, and other potential applications, large numbers of cells are required. The number of hESC that may be obtained with monolayer cultures is limited. Culture of hESC in suspension rather than in a monolayer is required to develop bulk cultures of hESC. Suspension cultures of hESC may allow extensive expansion of the cells with a bioreactor system. It may allow initiation of differentiation processes in suspension of a large number of cells, and the development of novel methodologies to direct differentiation of hESC within suspension cultures.

In the context of this aspect of the invention there is also provided a method for maintaining SC, preferably human, more preferably, hESC, in an undifferentiated state, the method comprising incubating the SC with a culture system comprising Neurobasal™ in a growth environment, in which cells of interest will proliferate in vitro, as detailed herein.

The invention will now be described by way of non-limiting examples. It is to be understood that the invention is not limited in its application to the details set forth in the following description or exemplified by the examples. The invention is capable of other embodiments or of being practiced or carried out in other various ways. Also, it is to be understood that the phraseology and terminology employed herein is for the purpose of description and should not be regarded as limiting.

Some Exemplary Embodiments
Materials and Methods
Non-Clinical Grade Culture System of Human Feeders and hESC
Human Feeders Human foreskin or embryonic feeder cells were cultured in DMEM (Gibco, Gaithersburg, Md.) supplemented with 10% Fetal Calf Serum (Biological Industries, Beit Haemek, Israel). They were passaged by Trypsin (Gibco, Gaithersburg, Md.) digestion and plated on 0.1% Gelatin (Sigma, St. Louis, Mo.)-precoated tissue culture dishes.
HES Cell Culture Human ESC (HES1 and HES2 cell lines) were cultured on the human feeder layers in KO medium (KOM) consisting of 85% KO-DMEM, 15% KOSR, 1 mM glutamine, 0.1 mM β-mercaptoethanol, 1% nonessential amino acids, 50 units/ml penicillin, 50 μg/ml streptomycin, (Gibco, Gaithersburg, Md.) and 4 ng/ml bFGF (R&D Systems, Inc., Minneapolis, Minn.). hES cells were weekly passaged by dissociation into nearly single cell suspension with Ca/Mg$^{++}$-free PBS supplemented with 0.05% EDTA (Biological Industries, Beit Haemek, Israel) and plated onto fresh feeder layer.
EBs Formation and Characterization Human ES cells were removed from the feeders by treatment with dispase (10 mg/ml; Gibco), and/or type IV collagenase (1 mg/ml; Gibco). The clusters of undifferentiated cells that were obtained were further triturated into smaller clumps within PBS. These clumps were cultured for various periods in suspension within bacteriological dishes precoated with 0.1% low melting temperature agarose in DMEM (Gibco), supplemented with 10-20% FCS (Biological Industries, Beit Haemek), 1 mM L-glutamine, 0.1 mM β-mercaptoethanol, 1% non-essential amino acid stock, 50 units/ml penicillin, 50 µg/ml streptomycin (all from Gibco Invitrogen Corporation products, USA) in the presence or absence of nicotinamide 10 mM (Sigma). In some experiments DMEM and FCS were replaced by 86% KO-DMEM and 14% KOSR or by Neurobasal medium supplemented by N2 (Gibco).

Immunohistological Studies of EBs

EBs that were developed 4 weeks in suspension culture in the presence and absence of nicotinamide (NA), were fixed in 4% paraformaldehyde at room temperature overnight. The EBs were then concentrated at the bottom of a centrifuge tube and embedded in agar. The agar blocks were dehydrated, and embedded in paraffin. 5-micron sections were immunostained with anti-human cytokeratin-8 and anti-α-fetoprotein (both at 1:50, monoclonal mouse IgG, DAKO). Primary antibody localization was performed using Picture™ plus kit (Zymed).

Indirect Immunofluorescent Staining of Differentiated Cells within EBs or Neural Spheres Differentiation into neural spheres was conducted according to the published protocol (Itsykson, P., et al. Derivation of neural precursors from human embryonic stem cells in the presence of noggin. *Mol Cell Neurpsci* 30, 24-36 (2005). Spheres were dissociated mechanically by trituration. Pigmented clusters of cells within EBs, differentiating 8-10 weeks were mechanically dissected by glass micropipettes or scalpel blades.

EBs were dissociated into smaller clusters mechanically with/without the aid of trypsin (0.025%, 3 mM EDTA in PBS) digestion. The small clusters of cells were plated on poly-D-lysine (30-70 kDa, 10 µg/ml; Sigma, St. Louis, Mo.) and laminin-coated (4 µg/ml; Sigma) glass coverslips and cultured for additional 3-5 weeks in the culture medium used for suspension culture of EBs or neural spheres. Differentiated cells within the outgrowth were fixed with 4% paraformaldehyde for 20 minutes at room temperature. Cell membranes were permeabilized with 0.2% Triton X100 (Sigma) in PBS for 5 minutes for immunostaining with ant-intracellular markers antibodies. The cells were incubated with the following primary antibodies: anti β-tubulin III (mouse monoclonal IgG2b, 1:2000, Sigma), anti human alphafetoprotein (mouse monoclonal IgG2a, 1:200, Sigma), anti human muscle actin (mouse monoclonal IgG1, 1:10, Dako) and anti human desmin (mouse monoclonal IgG1,κ, 1:10, Dako), anti-Pax6 (Developmental Studies Hybridoma Bank; mouse monoclonal IgG$_1$, 1:100), anti-MITF (Lab Vision Corporation, Fremont, Calif.; mouse IgG$_1$, 1:50), anti-RPE65 (Novus Biologicals, Littleton, Colo.; mouse IgG$_1$, 1:300), anti-Bestrophin (Novus Biologicals, Littleton, Colo.; mouse IgG$_1$, 1:150), anti-ZO-1 (Zymed Laboratories Inc., South San Francisco, Calif.; rabbit polyclonal, 1:10) and anti-CRALBP (kindly provided by John C. Saari, University of Washington, Seattle; rabbit polyclonal, 1:100).

Primary antibody localization was performed by using fluorescein isothiocyanate (FITC)-conjugated goat anti-mouse immunoglobulins (Dako, 1:20-50), goat anti-mouse IgG conjugated to Cy$^{TH}$3 (1:500) and swine anti-rabbit Ig conjugated to fluorescein isothiocyanate (FITC) (Dako, A/S Denmark; 1:50).

Analysis of EBs by RT PCR

For RT PCR analysis, total RNA was collected from EBs that were developed 4 weeks in suspension culture in the presence and absence of nicotinamide (NA). Total RNA was isolated using TRI REAGENT (Sigma) and converted into complementary cDNA with M-MLV reverse transcriptase (Promega). PCR was carried out using standard protocols with Taq DNA Polymerase (Promega). Amplification conditions were as follows: denaturation at 94° C. for 60 seconds, annealing at 55-60° C. for 60 seconds, and extension at 72° C. for 60 seconds. The number of cycles was 35 Primer sequences and lengths of amplified products were:
Chordine-Like (NCBI Gene Bank: BC002909)

| | |
|---|---|
| 5'TGCAAGGTGTGTCCAGGTAA; | (SEQ ID NO: 1) |
| 3'CCAGCTTGAAGTGAGGAAGC; | (SEQ ID NO: 2) |

The length of amplification product was 268 bp.
α-fetoprotein (NCBI Gene Bank NM001134)

| | |
|---|---|
| 5'CCATGTACATGAGCACTGTTG; | (SEQ ID NO: 3) |
| 3'CTCCAATAACTCCTGGTATCC. | (SEQ ID NO: 4) |

The length of amplification product was 338 bp.

Intravitreal and Sub-Retinal Transplantation of hESC-Derived RPE Cells

Clusters of pigmented cells were mechanically isolated by scalpel blades from EBs that were differentiating in the presence of NA for 6-8 weeks. The clumps were dissociated into smaller clusters of cells by digestion with Papain (Papain Dissociation System; Worthington Biochemical Corporation, Lakewood, N.J.) at 37° C. for 30 minutes followed by trituration. Adult (body weight 230-250 g) outbred RCS and albino rats were used for intraocular transplantation. All animal experiments were conducted according to the ARVO Statement for the Use of Animals in Ophthalmic and Vision Research, and approved by the institutional committee for animal research. The animals were anaesthetized with Ketamine HCl (Ketalar, Parke Davis, UK, 100 mg/kg), injected intra-peritonealy in combination with the relaxing agent Xylazine (2.0 mg/kg). Local anaesthetic drops (Benoxinate HCl 0.4%, Fischer Pharmaceuticals, Israel) were administered. The pupils were dilated with Tropicamide 0.5% (Mydramide, Fisher Pharmaceuticals, Israel) and Phenylephrine HCl 2.5% (Fisher Pharmaceuticals, Israel). Under visualization of a dissecting microscope (Stemi SV 11, Zeiss, Germany), about 100,000 cells in 4 µL medium were injected into the vitreous or to the subretinal space by a Hamilton syringe and a 33 gauge needle via a transscleral, transchoroidal approach. Fellow, non-injected eyes served as one type of control. As an additional control, adult eyes were injected with saline (Sodium Chloride Injection BP, 0.9%, B. Braun Melsungen AG, Melsungen, Germany). During and after injection, no choroidal bleeding was observed. Animals were kept warm throughout and after the procedure using a heating lamp. Following transplantation, all animals received the immunosuppressive agent cyclosporine A (Sandimmune, Novartis Pharma AG, Basle, Switzerland, 50 mg/ml) in their drinking water at a concentration of 210 mg/l. At 4 weeks post-injection, animals were sacrificed and eyes enucleated for histological and immunohistochemical examination. Following transcardial perfusion with 4% paraformaldehyde in 0.1 M phosphate buffer, eyes were embedded in paraffin and sectioned at 4 µm serial sections. Each fifth slide was stained with hematoxylin and eosin for histomorphologic evaluation. For indirect immunofluorescent studies, specimens were deparafinized in xylene and dehydrated in graded alcohols, rinsed with phosphate-buffered saline (PBS, pH 7.4), and incubated with 10 mM citrate buffer (pH 6.0) at 110° C. for 4 minutes. After washing with PBS, specimens were blocked for 1 hour at room temperature with PBS solution containing 1% bovine serum albumin, 0.1% triton-x100, and 3% normal goat serum. Subsequently, sections were incubated for 24 hours at 4° C. in a humidified chamber with anti-green fluorescent protein (anti-GFP; Santa Cruz Biotechnology; rabbit polyclonal, 1:100). After washing in PBS, specimens were incubated for 1 hour at room temperature with Cy™2 conjugated goat anti-rabbit IgG (1:200). Nuclei were counterstained with 4, 6-diamidino-2-phenylindole (DAPI)-containing mounting medium (Vector Laboratories, Inc., Burlingame, Calif.). To determine the specificity of the antigen-antibody reaction, corresponding negative controls with an irrelevant isotype-matched antibody were performed. A Zeiss Axiovert 200 microscope equipped with Sensi Cam 12 Bit imaging (Zeiss, Kelheim, Germany) was used for fluorescent and light microscopy imaging.

Clinical Grade Feeder and hESC Culture System

Development of Human Feeders

Human feeders were obtained via Informed Consent from aborted fetuses (10-12 weeks of gestation), umbilical cords, and newborn foreskin.

The legs and hands of aborted human fetuses were washed twice and transferred to a drop of 200 µl of medium comprised of HyQ DMEM (Hyclone, Utah) containing 10% human serum (Cambrex, Maryland,) and were minced with two scalpel blades into small pieces of tissue. The minced embryonic tissues were incubated 10 minutes in 10 ml TrypLE Select (Gibco, Gaithersburg, Md.) solution at 37° C. with intermittent shaking. The supernatant was then collected and inactivated by diluting the solution with 35 ml of the medium for fibroblast culture (feeders medium) that was comprised of HyQ DME (Hyclone, Utah) supplemented with 10%-20% human serum (Cambrex, Maryland), and 2 mM glutamine (Hyclone, Utah). This procedure was performed twice. The cells were spun down and 4-5×10$^6$ cells were plated in T-25 tissue culture dishes for further propagation in feeders medium as above. When confluent, they were passaged using TrypLE Select solution (Gibco, Gaithersburg, Md.).

Term umbilical cord tissue was minced as above, and the small pieces of tissue were plated in the fibroblast culture medium, as described above. To promote the adherence of the tissue pieces to the culture dish, flasks were incubated upright overnight. Cells emanating from the tissue pieces were propagated as above.

Foreskin tissue was obtained from 7 day to 6 months circumscribed newborns and babies. Circumcision was performed in the operating room, and the medium described above was used for the development and culture of the foreskin feeders. The circular foreskin was cut and spread on the tissue culture dish. The epidermis was scraped with scalpel blade followed by washing with the culture medium. This was repeated 5 times and small foreskin tissue pieces were plated in the culture medium within a flask. The flask was incubated upright to enhance the adherence of tissue pieces to the dish and promote outgrowth of fibroblasts.

All fibroblasts were cryopreserved in human serum (Cambrex, Maryland, Maryland) supplemented with 10% Cryosure-DMSO (Wak-Chemie, Germany) Slow-cooling and rapid-thawing standard methods were used.

For indirect immunofluorescent staining the fibroblasts were plated and cultured on cover slides. They were fixed with 4% paraformaldehyde for 20 minutes at room temperature, and then permeabilized with 0.2% Triton X100 (Sigma) in PBS for 5 minutes. The cells were incubated with anti human vimentin (mouse monoclonal IgG2a, κ Dako, 1:10). Primary antibody localization was performed by using fluorescein isothiocyanate (FITC)-conjugated goat anti-mouse immunoglobulins (Dako, 1:50).

FACS analysis of marker expression by the feeders was performed by using a FACS Calibur system (Becton-Dickinson, San Jose, Calif.). Propidium Iodide was added (final concentration of 4 µg/ml) for better gating of viable cells. The feeders were disaggregated using TrypLE Select solution (Gibco, Gaithersburg, Md.). The cells were then washed with FACS media consisting of PBS supplemented with 1% BSA and 0.05% sodium azide. The single cell suspension was stained with Anti-human fibroblasts antibodies (mouse monoclonal IgG2a, Acris, 1:100) and Anti human CD44 FITC-conjugated antibody (mouse monoclonal IgG2b, IQ Products, The Netherlands, 1:10). Control feeders were stained with an isotype control antibody. Primary anti-human fibroblasts antibodies were detected with a FITC-labeled goat anti-mouse Ig (1:100, Dako).

Clinical Grade hESC Culture System

Human embryonic fibroblasts derived from umbilical cord as described herein or foreskin fibroblasts were used as feeders. The feeders were plated in tissue culture dishes precoated with 1 µg/cm$^2$ human Fibronectin (BD Biosciences, Bedford, Mass.) or 100 µg/ml recombinant Gelatin (FibroGen, SF). Mitotic inactivation was carried out by incubating the feeders 2.5 hours with Mitomycin-C (Kyowa, Tokyo). KO DMEM (Gibco), X-Vivo 10 (Biowhittaker, Maryland), or Cellgro Stem Cell Growth Medium (CellGenix Freiburg, Germany) were used as the basic media. They were supplemented with TCH (1-2%; Protide Pharmaceuticals, St. Paul, Minn.) or Nutridoma-CS (2%; Roche, Germany) as serum substitutes. The media were supplemented with 2 mM glutamine (Hyclone, Utah) and non-essential amino acids (NEAA, 1%; Hyclone Utah). HESC were split weekly with Ca/Mg$^{++}$-free PBS supplemented with 0.05% EDTA.

For cryo-preservation, hESC were disaggregated with Ca/Mg$^{++}$-free PBS supplemented with 0.05% EDTA, spun down, and re-suspended in Cellgro medium, supplemented with 2% TCH, and 10% Cryosure-DMSO (Wak-Chemie, Germany). Conventional slow-rate cooling and rapid-thawing methods were used.

FACS analysis of marker expression was performed on hESC after disaggregation using Ca/Mg$^{++}$-free PBS supplemented with 0.05% EDTA. The cells were then washed with FACS media consisting of PBS supplemented with 1% BSA and 0.05% sodium azide. The single cell suspension was stained with anti-SSEA4 (1:100, mouse monoclonal IgG3, Developmental Studies Hybridoma Bank (DHSB), Iowa City, Iowa), and anti-Tra-1-60 (1:20, monoclonal mouse IgM, gift from Prof. P. Andrews), anti-Tra-1-81 (1:100, monoclonal mouse IgM, Chemicon International), anti-human Oct 4 (mouse monoclonal IgG2b, 1:50, Santa Cruz), and anti-SSEA1 (1:100, Chemicon). Control hESC were stained with the respective isotype control antibodies. Primary antibodies were detected with a FITC-labeled goat anti-mouse Ig (1:100, Dako).

Suspension Culture of hESC

In the course of the routine passaging procedure, HESC colonies were dissociated with 0.05% of EDTA for 7-10 min at 37°, or mechanically with the aid of collagenase IV (1 mg/ml, 120 min at 37°). Cell dissociation was promoted by gentle blowing of the medium with a 1 ml pipette tip towards the hESC colonies. The cells/cell-clusters were re-suspended in NBN2 medium (Neurobasal, N2 supplement 1:100, glutamine 2 mM, 50 units/ml penicillin, 50 µg/ml streptomycin) supplemented with bFGF 20 ng/ml, noggin 250 ng/ml, activin 25-50 ng/ml, fibronectin and laminin 5 ng/ml each, gelatin 0.001%. The suspension may be strained though 30-50 micron mesh to remove big clumps and transferred into tissue culture dishes (Costar®, Corning Inc., Corning, N.Y., USA) at a density of ~0.7-1.2×10$^6$ cells/ml. Dead cells and their fragments were gradually removed during media refreshment and small transparent cell aggregates emerged from the 3$^{rd}$-5$^{th}$ days of suspension culture. The cells proliferated as free-floating tiny clusters of 20-50 cells. Aggregation and overgrowth of clusters was prevented by their daily trituration with a 1000 µl pipettor tip. Alternatively, every 7 days clusters were dissociated with Ca/Mg-free PBS supplemented with 3 mM EDTA and 0.06% trypsin and the single cells were resuspended in fresh medium.

Characterization of hESC Grown in Suspension

For characterization of the cells within the small floating aggregates, they were dissociated with EDTA solution (as above), followed by gentle trituration, and were plated in NBN2 on glass coverslips, pretreated with poly-D-lysine (30-70 kDa, 10 µg/ml; Sigma, St. Louis, Mo.) and laminin (4 µg/ml; Sigma). After one hour's incubation at 37°, the cells were incubated 1 min in propidium iodide solution (PI, 1 µg/ml in PBS, Sigma) in order to distinguish dead cells from vital ones. The cells were then washed with PBS and fixed with 4% PFA for 20 min. For immunostaining with antibodies against surface markers, the fixed cells were incubated for 30 min at room temperature (RT) with the following primary antibodies: anti-SSEA4 (1:200 of the concentrated monoclonal mouse IgM, Developmental Studies Hybridoma Bank (DHSB), Iowa City, Iowa), anti-Tra-1-60 (1:20), anti-Tra-1-81 (1:10) (monoclonal mouse IgM, gift from Prof. P. Andrews), anti-GCTM2 (supernatant, monoclonal mouse IgM, gift from Prof. M. Pera). For nuclear marker characterization, cells were pre-treated with 0.2% Triton X-100 (Sigma) and then stained with anti-Oct-4 (1:100, mouse monoclonal IgG, Santa Cruz Biotechnology, Inc., Santa Cruz, Calif.). Primary antibody localization was performed using fluorescein isothiocyanate (FITC)-conjugated with either goat anti-mouse immunoglobulins (Dako, 1:20) or goat anti-mouse IgM (1:200, Jackson Immunoresearch Laboratories, Inc., West Grove, Pa.). For the characterization of the effects of various growth factors and ECM components on the suspension culture system, hESC with an extra short arm (p) of chromosome 1 were used. FACS analysis was performed as above.

Results

Derivation and Propagation of hESC in Animal-Free Clinical Grade Culture Systems.

The development of animal-free culture systems for the propagation of undifferentiated hESC is an essential step towards the exploitation of hESC in transplantation therapy. To this end, culture systems for the derivation of human feeder cell and hESC lines from which therapeutic products can be derived have now been developed. These systems are compliant with both FDA and European regulations for Biological Products, using good manufacturing practices (GMPs) in their manufacture, good tissue practices (GTPs) in their production, and good laboratory practices (GLPs) in their testing. In these culture systems, animal-derived reagents are not used, and all reagents are purchased from sources that are GMP-compliant.

Human Feeder Cells (Feeders)

Various human feeders may be utilized, in these systems, for the derivation and propagation of undifferentiated hESC, such as human embryonic fibroblast (HEF) feeders, umbilical cord derived fibroblast feeders and foreskin-derived fibroblasts.

In the examples provided herein the feeder cells were developed and cultured using a clinical grade animal free culture system comprising the following reagents:

DMEM (HyQ DME (Hyclone, Utah or equivalent));
Human serum (Cambrex, Maryland, or equivalent), replacing fetal calf serum (FCS), which is most commonly used;
Human fibronectin or recombinant gelatin (FibroGen, SF, or equivalent), replacing the commonly used porcine gelatin for tissue culture dish coating;
TrypleSelect (Gibco, Gaithersburg, Md., or equivalent), a recombinant enzyme, replacing animal-derived trypsin for splitting of fibroblasts;
Cryosure-DMSO (Wak-Chemie, Germany), or equivalent, a GMP-qualified product for fibroblast cryopreservation;
Mitomycin-C (USP or equivalent) from a GMP-qualified source for fibroblasts mitotic inactivation.

By using the above reagents, new human fibroblast cell lines were derived from foreskin, aborted fetuses and umbilical cords (FIG. 1A-1D).

Overall, 8 new foreskin-derived, 10 umbilical cord-derived and 5 aborted fetuses-derived fibroblast cell lines were developed, of which 6, 8, and 3 were developed within a GMP facility, respectively.

Figure 1A:
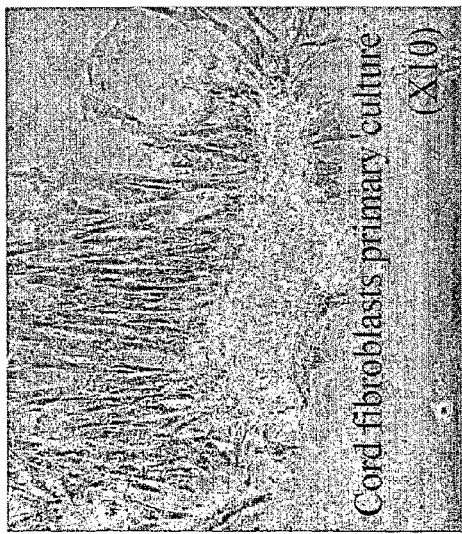
Figure 1C:
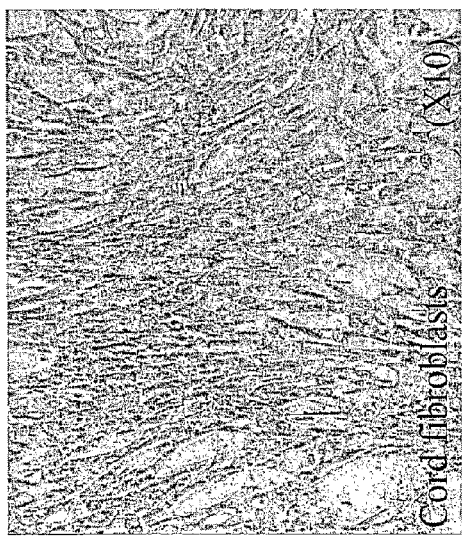
Figure 2D:
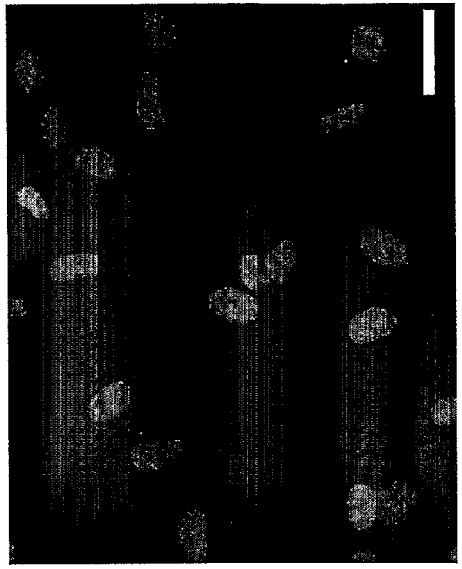
Figure 2F:
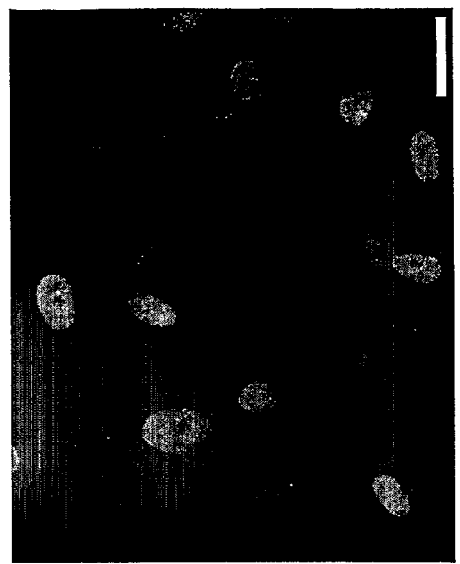
Figure 2C:
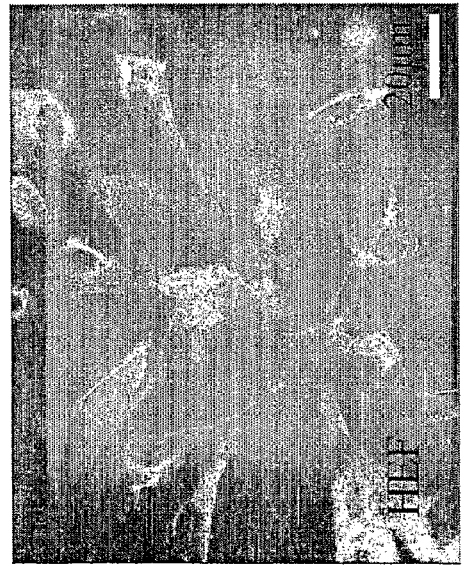
Figure 2E:
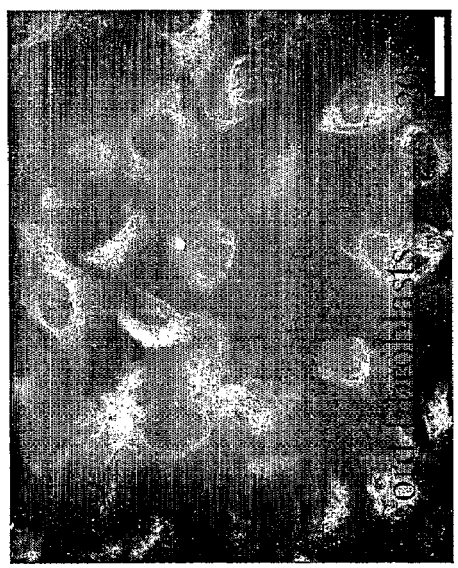
Figure 3:
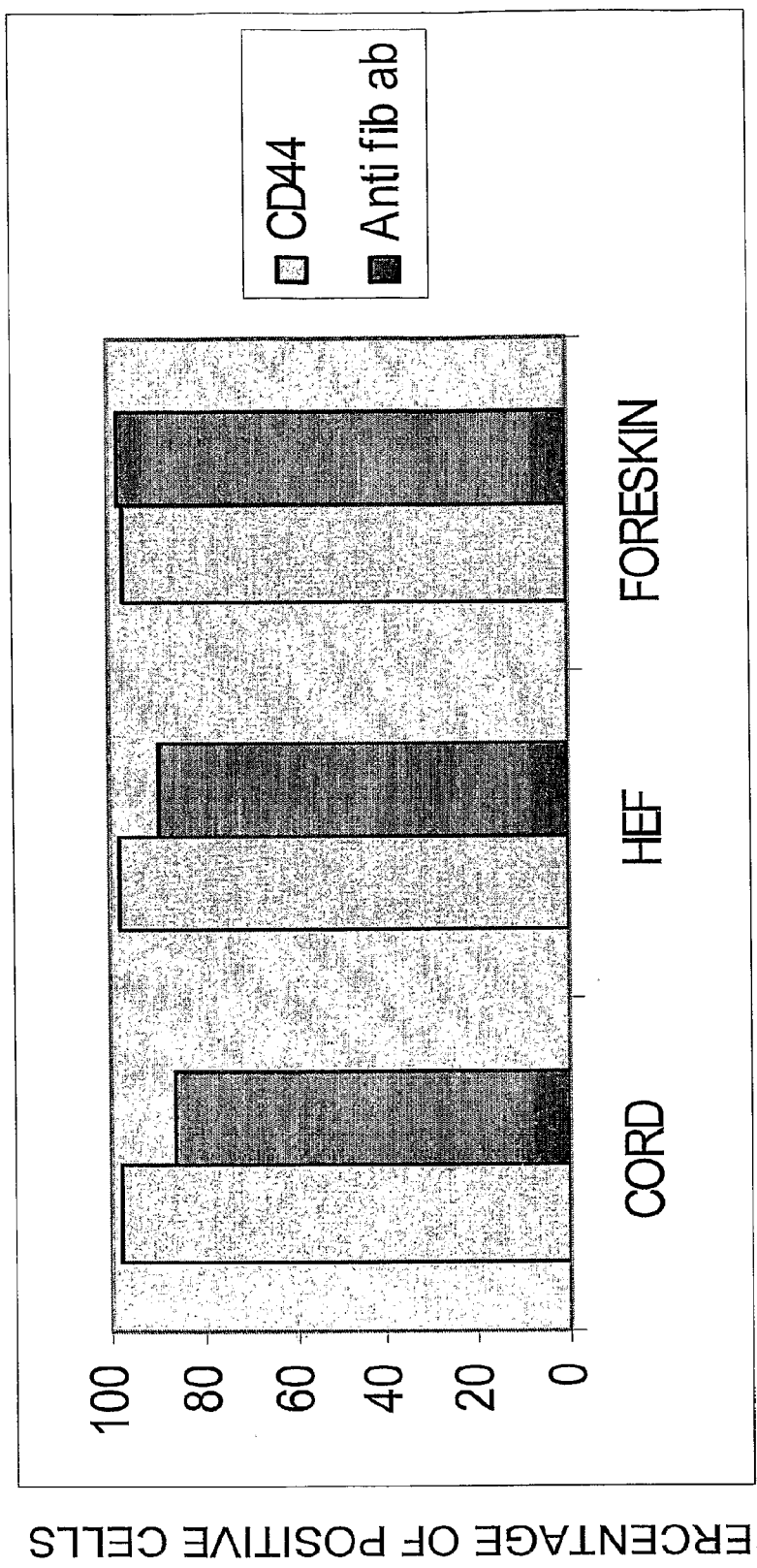
FIG. 3—is a bar graph showing FACS analysis of the percentage of feeders expressing CD44 and that are immunoreactive with anti-fibroblast antibody indicating that a high percentage of the feeders that are derived from the three sources express CD44 and are immunoreactive with anti-fibroblast antibody.

Two fibroblasts cell lines derived from each of the three groups (overall 6 cell lines), were characterized between passages 5-8. The cells had a typical fibroblast morphology (FIGS. 1A and 1C). Immunostaining demonstrated that over 70% of the cells in each of the cell lines were immunoreactive with markers of fibroblasts including but not limited to anti-vimentin (FIGS. 2A-2F), anti-CD 44 and anti-human fibroblasts antibody (FIG. 3). The karyotype of the feeders was normal (FIG. 4A). Fibroblasts doubling rate was between 20-50 hours (Table 1). The DNA had a definitive human STR profile (not shown).

TABLE 1

Number of umbilical cord derived fibroblast cells

| Feeder Line | Time = 0 | Time = 24 hr. | Time = 48 hr. | Time = 75 hr. | Doubling Time |
|---|---|---|---|---|---|
| Cord 1 P$_6$* | 118148 | 252777 | 330833 | 400000 | 42.3 hrs |
| Cord 2 P$_6$ | 35185 | 52962 | 83555 | 91851 | 49.9 hrs |
| Foreskin 2 P$_5$ | 31705 | 130000 | 260000 | 273000 | 23.2 hrs |
| Foreskin 4 P$_5$ | 36666 | 115000 | 232592 | 396111 | 21.2 hrs |
| HEF1 P$_6$ | 54259 | 114259 | 176876 | 357916 | 27.3 hrs |
| HEF2 P$_6$ | 61093 | 115370 | 199092 | 309166 | 31.8 hrs |

*P$_i$ denotes the number of passages

In order to evaluate the potential of these fibroblast cell lines to support the undifferentiated propagation of pluripotent hESCs, hESCs were cultured on the feeder layers for a period of ten weeks and their phenotype as well as developmental potential were characterized. The phenotype of the hESCs was characterized at two time periods. The first time point, between passages 1-5 and the second time point, between passages 6-10.

Figure 5B:
FIG. 5A-5C—are phase contrast images of colonies of undifferentiated hESC that are cultured on three types of human feeders, on umbilical cord derived feeders (FIG. 5A), human embryonic fibroblasts (FIG. 5B) and on foreskin derived feeders (FIG. 5C)
Figure 5C:
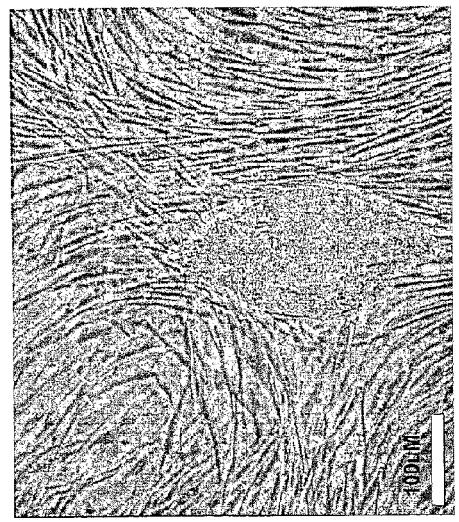
Figure 5A:
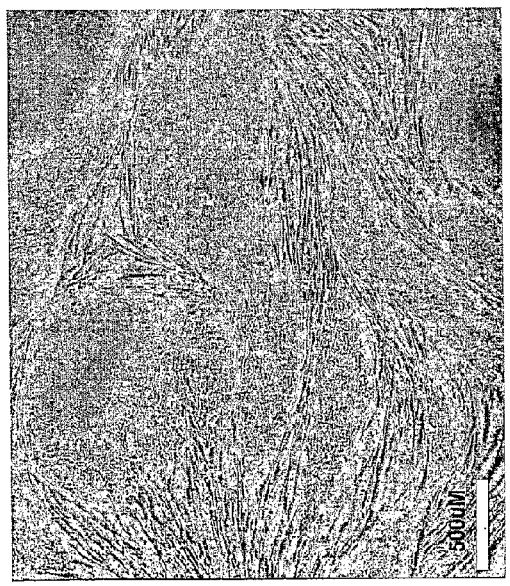
Figure 6A:
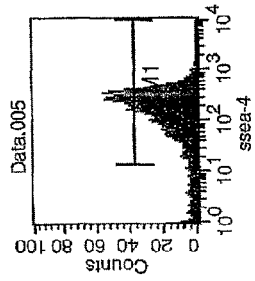
FIG. 6A-6L are representative FACS histograms of marker expression by hESC cultured on the three feeder fibroblast types, including expression of SSEA4, TRA1-60, TRA1-81 and SSEA1 by hESC on cord derived feeders (FIGS. 6A-6D, respectively), by hESC on human embryonic fibroblasts (FIG. 6E-6H, respectively) or by hESC on foreskin (FIG. 6I-6L, respectively).
Figure 6B:
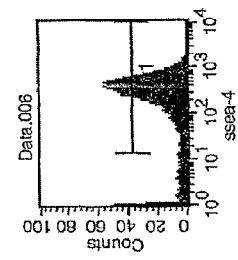
Figure 6C:
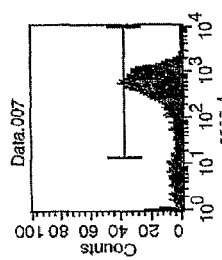
Figure 6D:
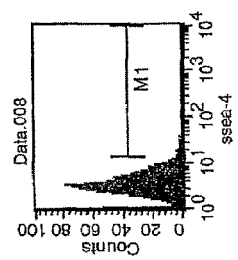
Figure 6E:
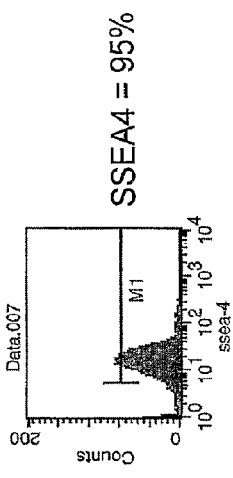
Figure 6F:
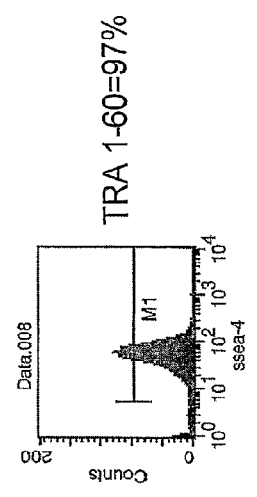
Figure 6G:
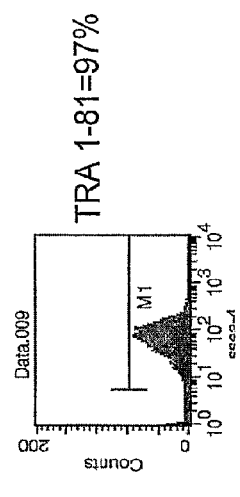
Figure 6H:
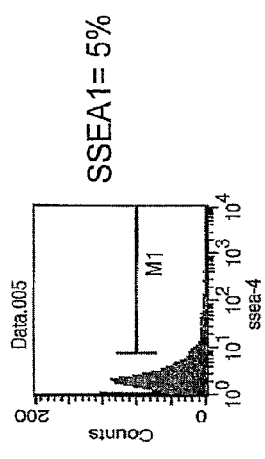
Figure 6I:
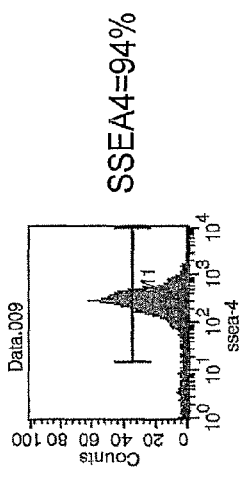
Figure 6J:
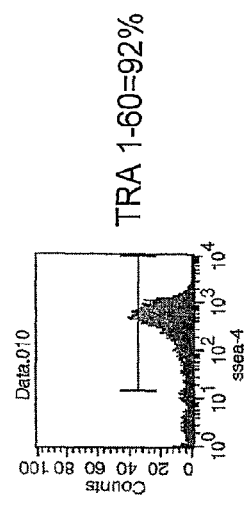
Figure 6K:
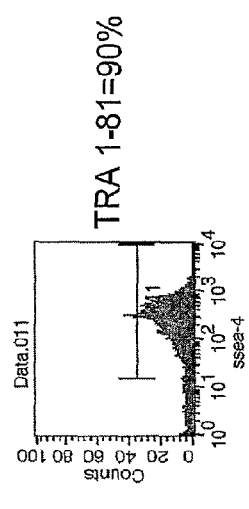
Figure 6L:
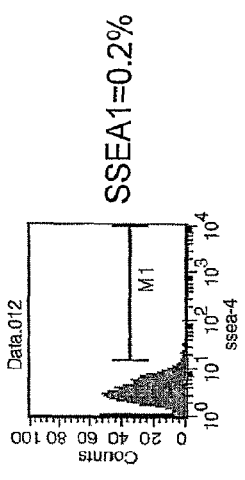
Figure 8C:
FIG. 8A-8F—are immunofluorescent images (FIGS. 8A, 8B and 8C) and the corresponding DAPI nuclear counter staining (FIGS. 8D, 8E and 8F) of hESC colonies expressing Oct4 when cultured on human embryonic fibroblast cells (FIGS. 8A and 8D, cultured for 6 weeks), on foreskin derived feeders (FIGS. 8B and 8E, cultured for 1 week) and on umbilical cord derived feeder cells (FIGS. 8C and 8F, cultured for 10 weeks).
Figure 8B:
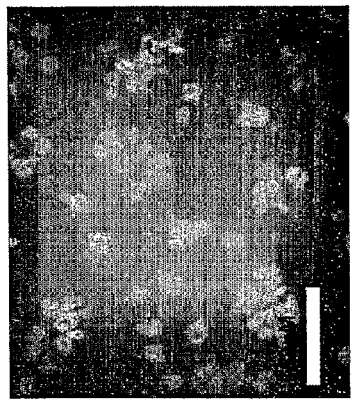
Figure 8A:
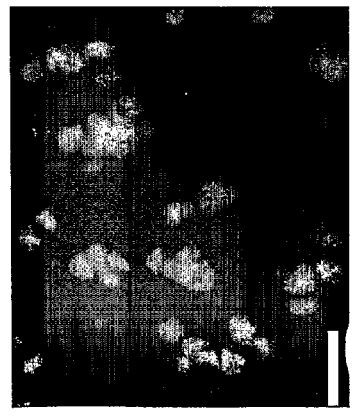
Figure 8F:
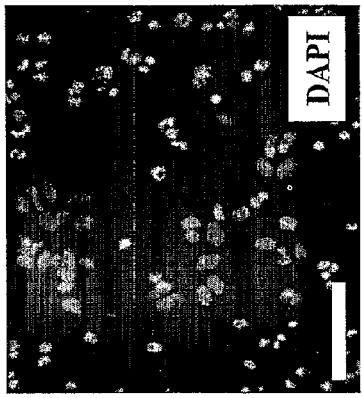
Figure 8E:
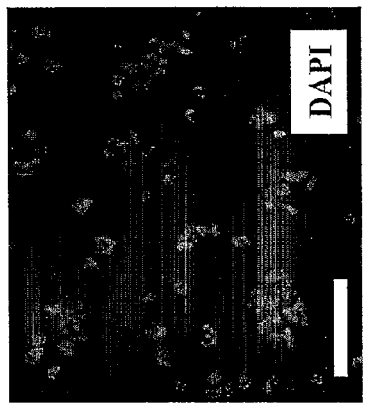
Figure 8D:
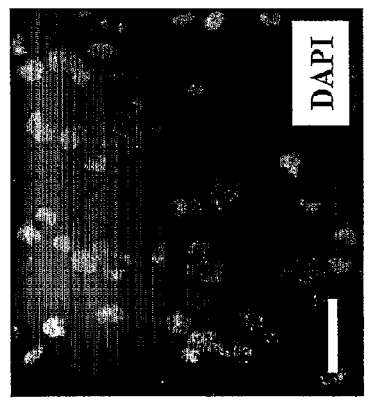
Figure 9:
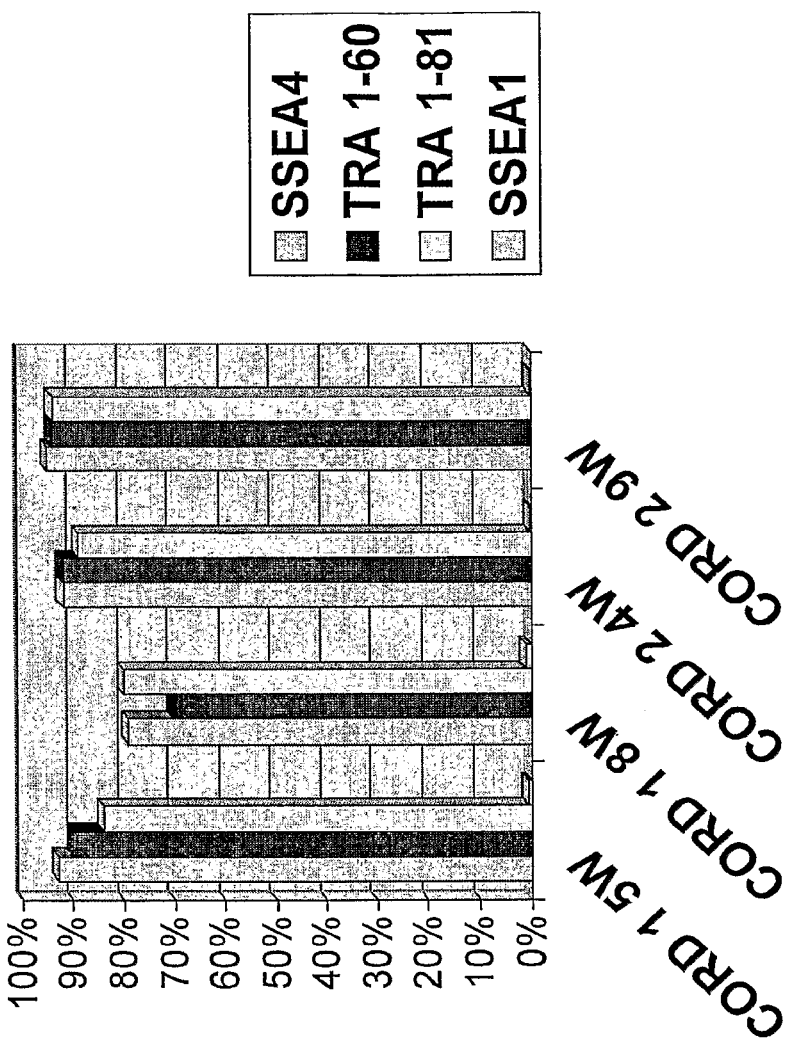
FIG. 9—is a bar graph representing FACS analysis of the percentage of hESC cultured on two independent cord derived feeder cell lines (CORD1 and CORD2), and expressing the indicated markers of undifferentiated pluripotent stem cells at early (1-5) and late (6-10) passage levels, showing that the percentage of hESC expressing these markers is stable during propagation, as determined after 5, 8, 4 and 9 weeks of culture (5W, 8W, 4W and 9W).
Figure 10:
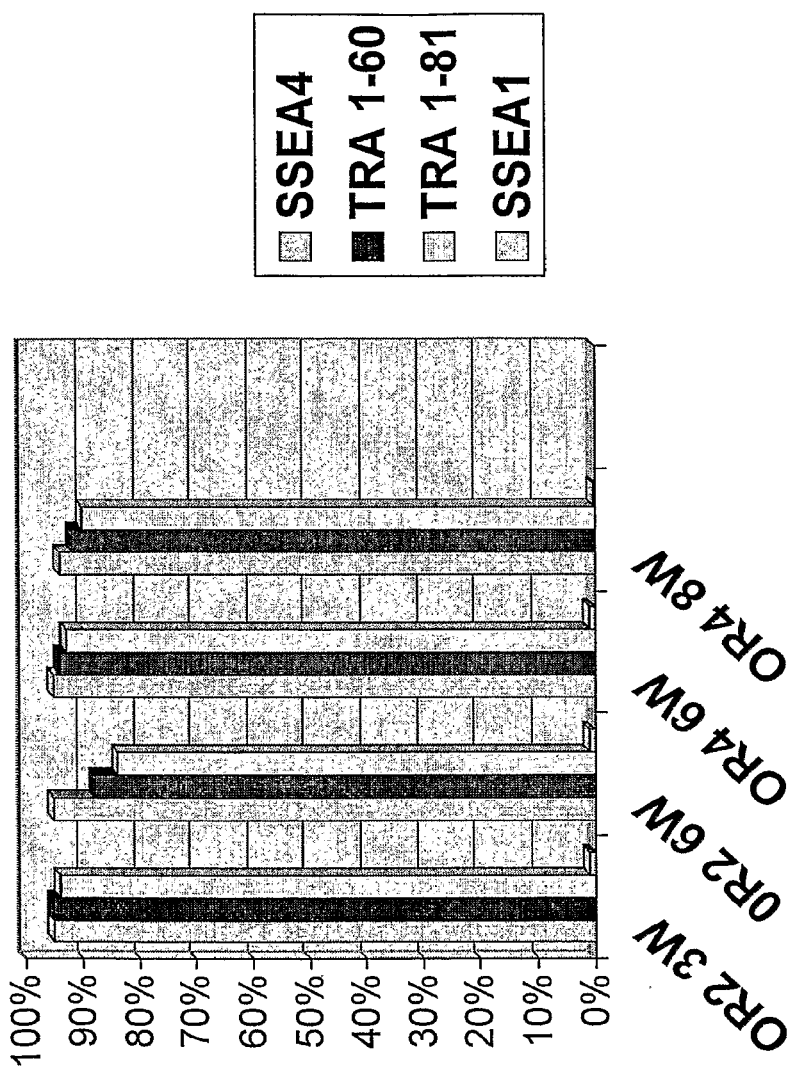
FIG. 10—is a bar graph representing FACS analysis of the percentage of hESC cultured on two independent foreskin-derived feeder cell lines (OR2 and OR4), and expressing the indicated markers of undifferentiated pluripotent stem cells at early (1-5) and late (6-10) passage levels, showing that the percentage of hESC expressing these markers is stable during propagation as determined after 3, 6, and 8 weeks of culture (3 W, 6 W and 8 W).
Figure 11:
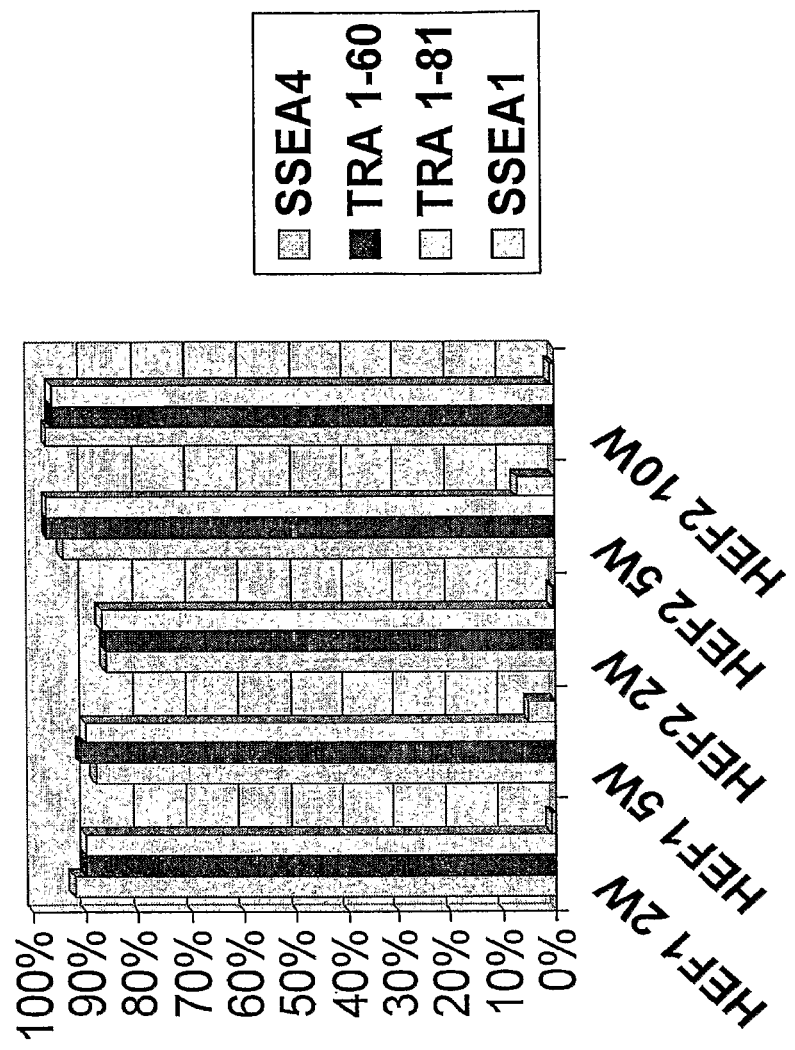
FIG. 11—is a bar graph representing FACS analysis of the percentage of hESC cultured on two independent human embryonic fibroblast feeder cell lines (HEF1 and HEF2), and expressing the indicated markers of undifferentiated pluripotent stem cells at early (1-5) and late (6-10) passage levels, showing that the percentage of hESC expressing these markers is stable during propagation, as determined after 2, 5 and 10 weeks (2W, 5W and 10W).
Figure 12:
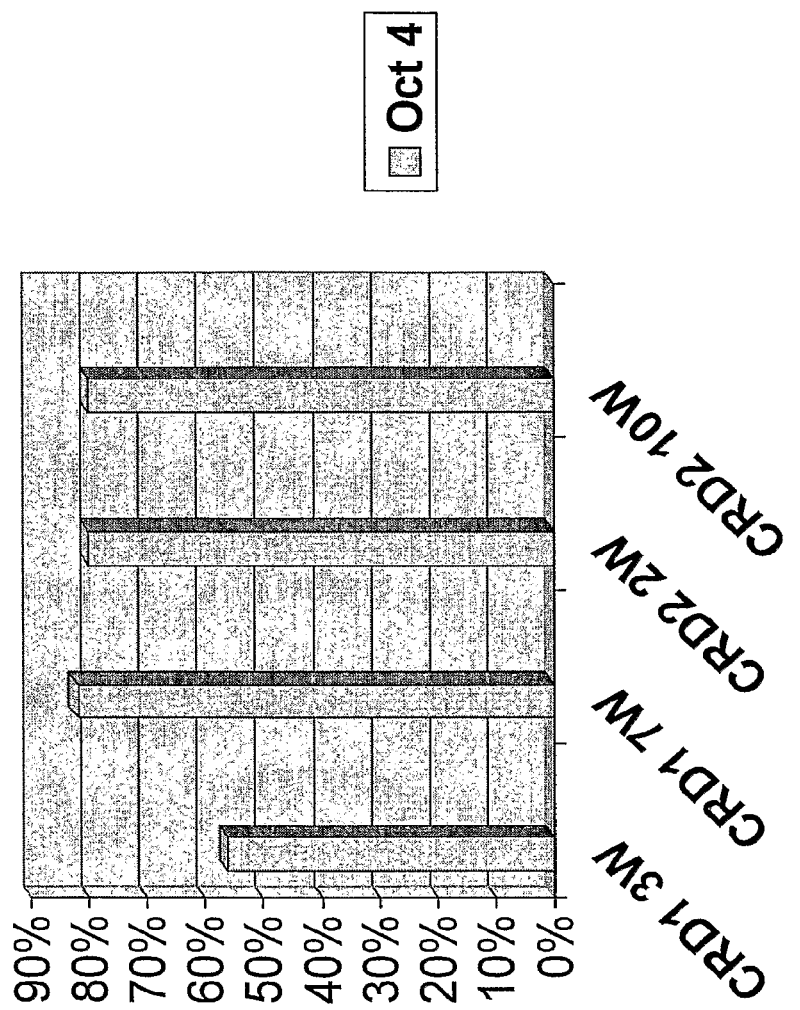
FIG. 12—is a bar graph representing analysis of the percentage of hESC cultured on two independent cord derived feeder cell lines (CORD1 and CORD2), and expressing Oct 4 at early (1-5) and late (6-10) passage levels and which was found to be stable during propagation as determined after 2, 3, 7 and 10 weeks (2W, 3W, 7W and 10W).
Figure 13:
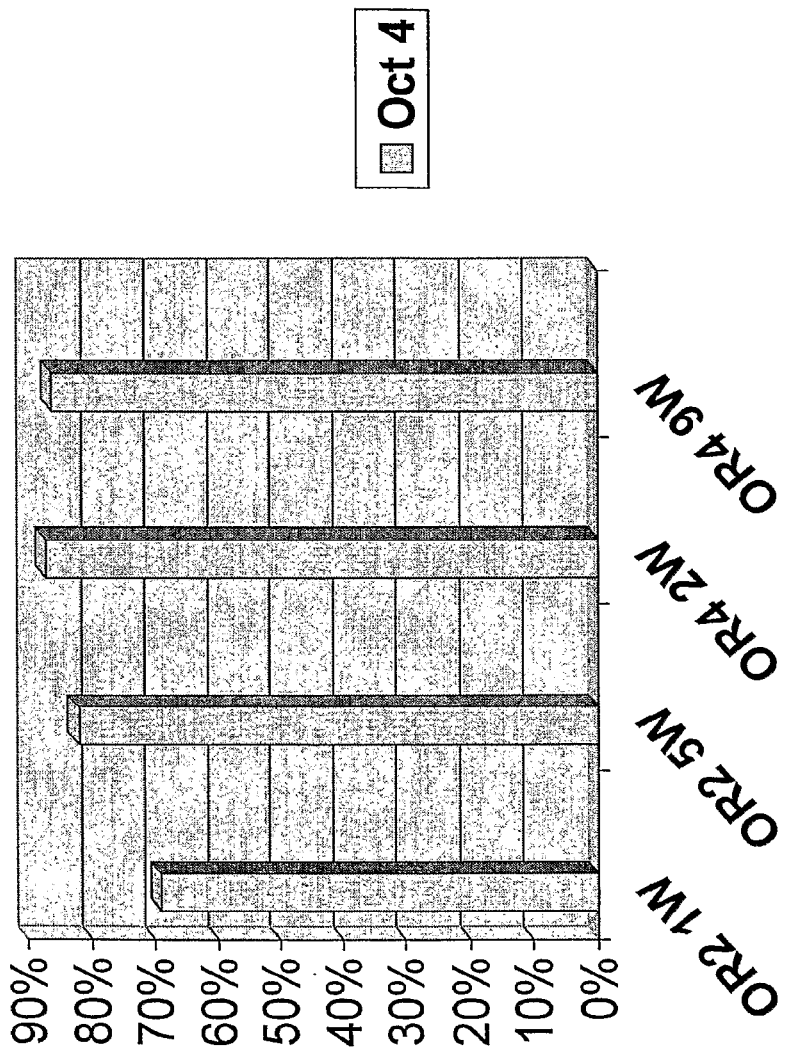
FIG. 13—is a bar graph representing analysis of the percentage of hESC cultured on two independent foreskin-derived feeder cell lines (OR2 and OR4), and expressing Oct 4 at early (1-5) and late (6-10) passage levels and which was found to be stable during propagation as determined after 1, 2, 5 and 9 weeks (1W, 2W, 5W and 9W).
Figure 14:
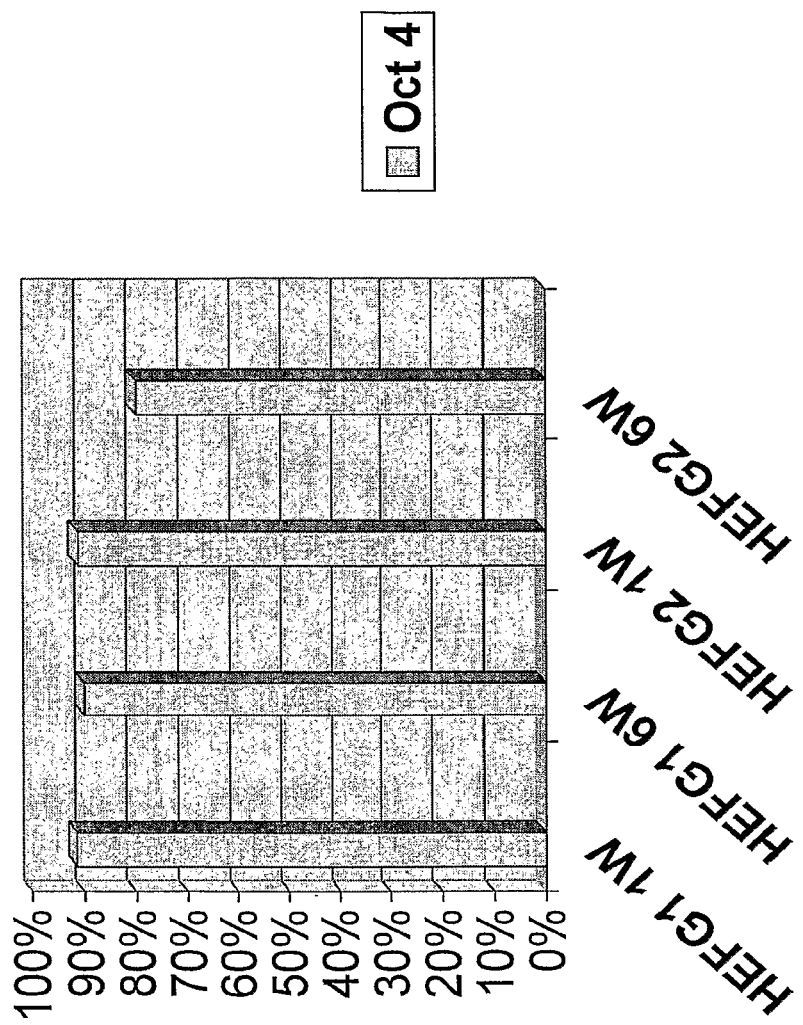
FIG. 14—is a bar graph representing analysis of the percentage of hESC cultured on two independent human embryonic fibroblast cell lines (HEFG1 and HEFG2), and expressing Oct 4 at early (1-5) and late (6-10) passage levels and which was found to be stable during propagation as determined after 1 and 6 weeks (1W and 6W).
Figure 15C:
FIGS. 15A-15I are immunofluorescent images of EBs-derived differentiated cells expressing β-tubulin (FIGS. 15A, 15D and 15G), AFP (FIGS. 15B, 15E and 15H), desmin (FIGS. 15C and 15I), or muscle-actin (m-actin, FIG. 15F) when cultured on cord-derived feeders (FIGS. 15A-15C); on human embryonic fibroblasts (FIGS. 15D-15F); and on foreskin derived feeders (FIGS. 15G-15I).
Figure 15B:
Figure 15A:
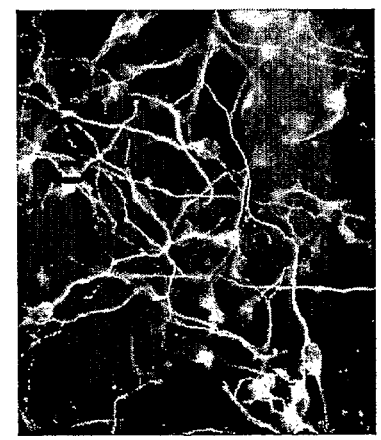
Figure 15F:
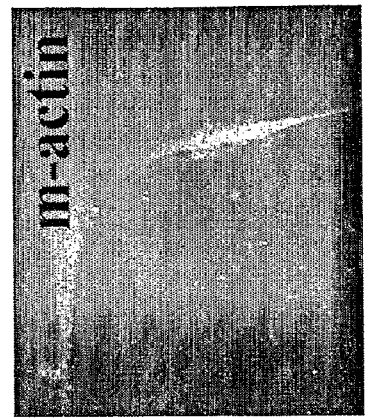
Figure 15E:
Figure 15D:
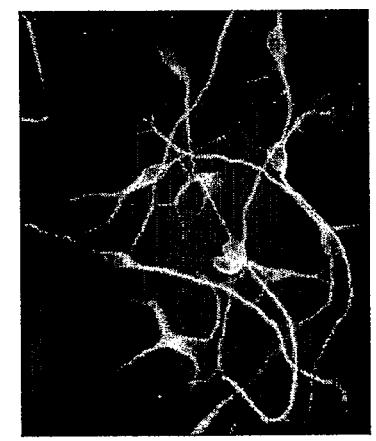
Figure 15I:
Figure 15H:
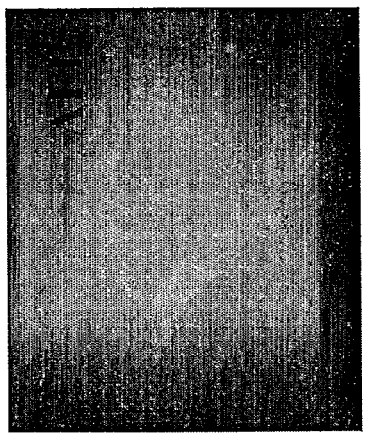
Figure 15G:

Human embryonic stem cells that were propagated on the three types of feeders (after freezing and thawing of the feeders) maintained their typical morphology (FIG. 5A-5C) and expressed the following cell surface markers of undifferentiated hESCs: SSEA-4, TRA-1-60, TRA-1-81 (FIG. 6A-6L) alkaline phosphatase (AP; FIG. 7A-7C), and Oct-4 (FIG. 8A-8F). Above 70% of the hESCs expressed markers of pluripotent cells when analyzed at the early and late passage periods (FIGS. 9-11, hESCs on cord, foreskin and HEF fibroblasts respectively; FIGS. 12-14 for Oct4, respectively). The percentage of hESC expressing SSEA1, a marker of differentiated cells, was less than 15% (FIGS. 9-11). These data indicated that all types of fibroblasts could support undifferentiated proliferation of the hESCs.

Doubling time of hES cultured on the feeders was 21-30 hours, with one exception of 36 hours (Table 2).

TABLE 2

No. of hESC cultured on three different types of feeders.

| Feeder Line | Time = 48 hr | Time = 120 hr | Time = 144 hr | Time = 168 hr | Doubling Time |
|---|---|---|---|---|---|
| hESC on Cord 1 | 26666 | 85185 | 172222 | 271851 | 35.8 hrs |
| hESC on Cord 2 | 28148 | 15666 | 397778 | 703166 | 20.3 hrs |
| hESC on Foreskin 2 | 25555 | 192251 | 275925 | 52000 | 28 hrs |
| hESC on Foreskin 4 | 26667 | 58518 | 493611 | 790000 | 19.4 hrs |
| hESC on HEF1 | 72129 | 448055 | 1147778 | — | 25.4 hrs |
| hESC on HEF2 | 84445 | 593612 | 1098889 | — | 27 hrs |

In these experiments, the hESC were cultured in KO DMEM supplemented with 20% KO SR.

In vitro differentiation of hESC cultured on the various feeder layers was induced by the derivation of EBs and neurospheres. The EBs and neurospheres were dissociated, plated, and stained for markers of the three germ layers (Alfafetoprotein for endoderm, β Tubulin III for ectoderm, and muscle-desmin or muscle actin for mesoderm). Human embryonic stem cells that were propagated to for 10 passages on each of the three types of feeders could differentiate in vitro into progeny representing the three germ layers (FIG. 15A-15I). These data show that the developmental potential of the hESC, when propagated on the three types of feeders, could be maintained for extended periods of time in culture.

Figure 16:
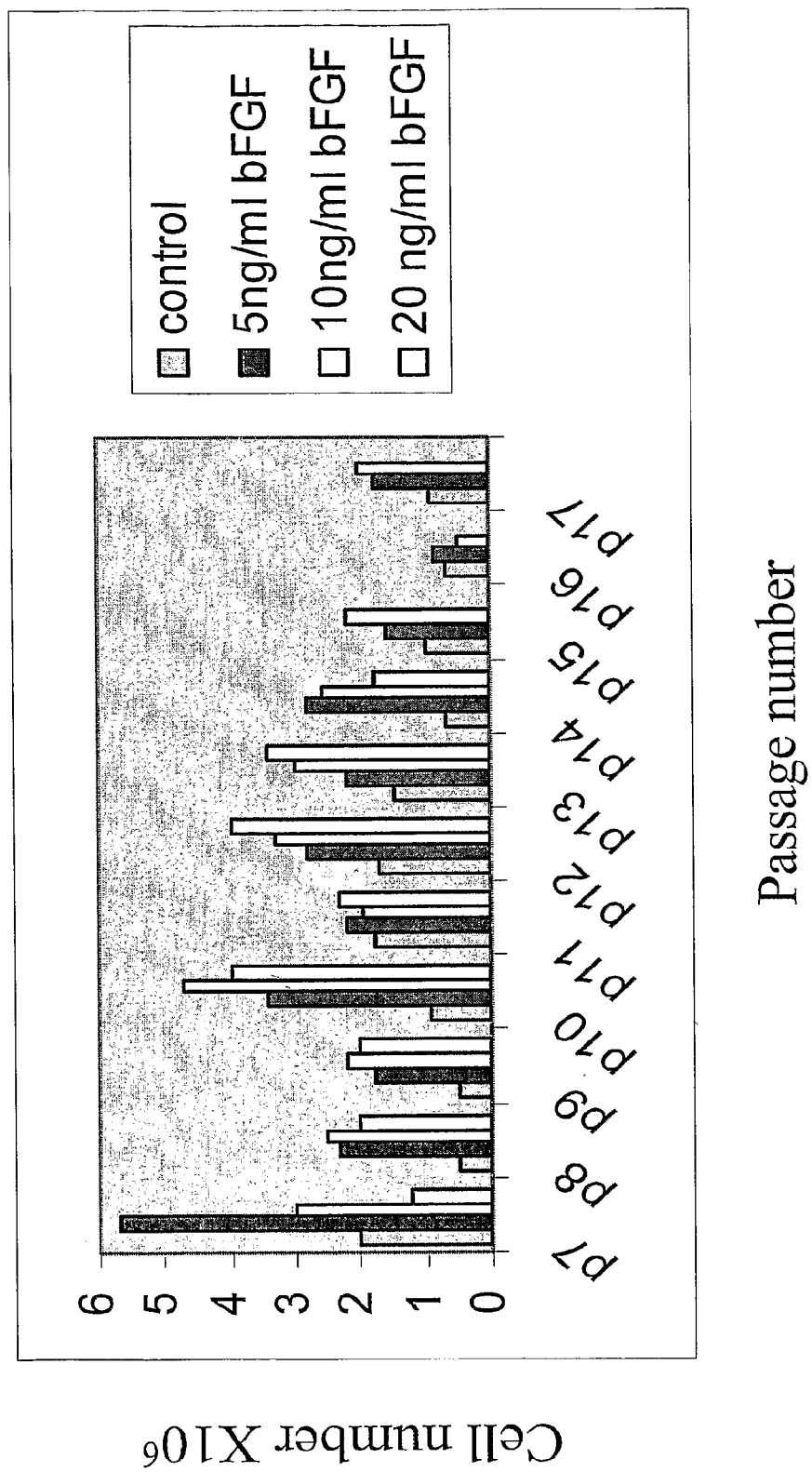
FIG. 16—is a bar graph showing the effect of bFGF at the indicated concentration on the number of cells that were harvested per flask at the time of the culture split as shown.
Figures 17A, 17B, 17C:
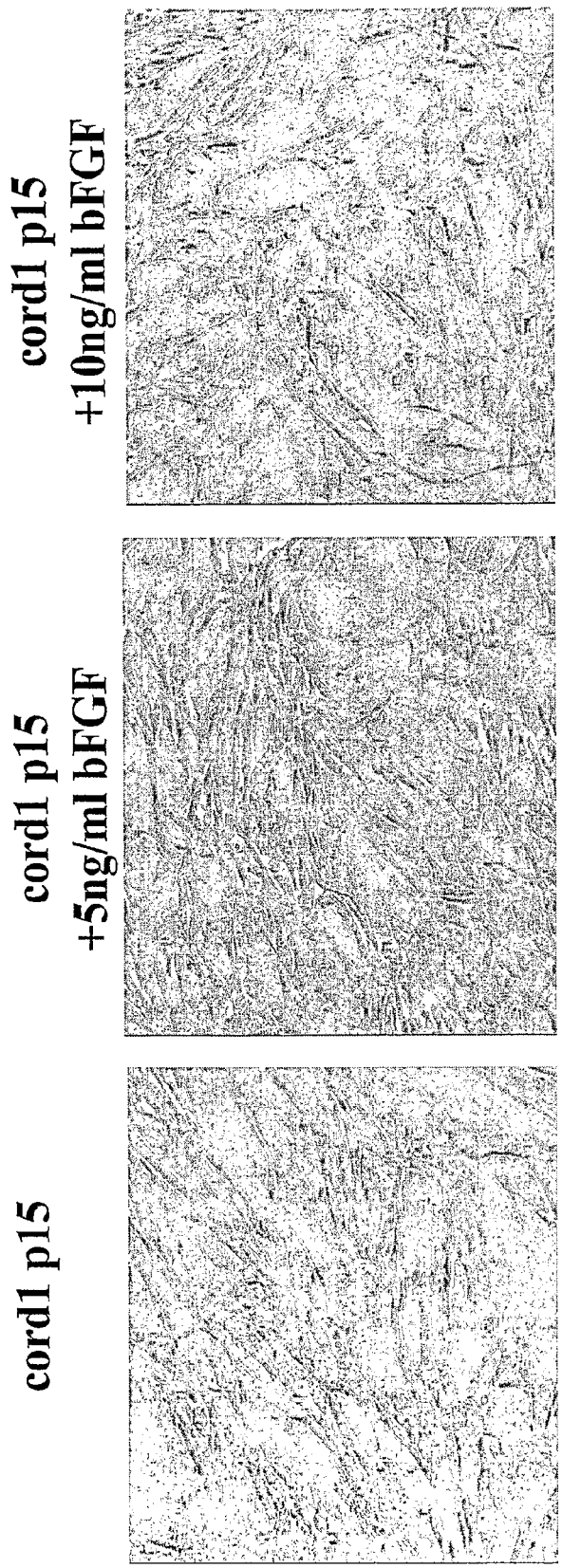
FIG. 17A-17D—are phase contrast images of cord-derived feeders, showing the effect of bFGF on their morphology after prolonged propagation in the presence of serum without bFGF-supplementation (FIG. 17A) or with the two indicated concentrations of bFGF supplementations (FIG. 17B and FIG. 17C), FACS analysis of the percentage of feeders expressing CD44 and that are immunoreactive with anti-fibroblast antibody (Anti-fib ab) is also shown (FIG. 17D). Analysis was performed at passage 10 in the presence of serum, and at passage 17 when the medium was supplemented with 5 ng/ml and 10 ng/ml of bFGF.
Figure 17O:
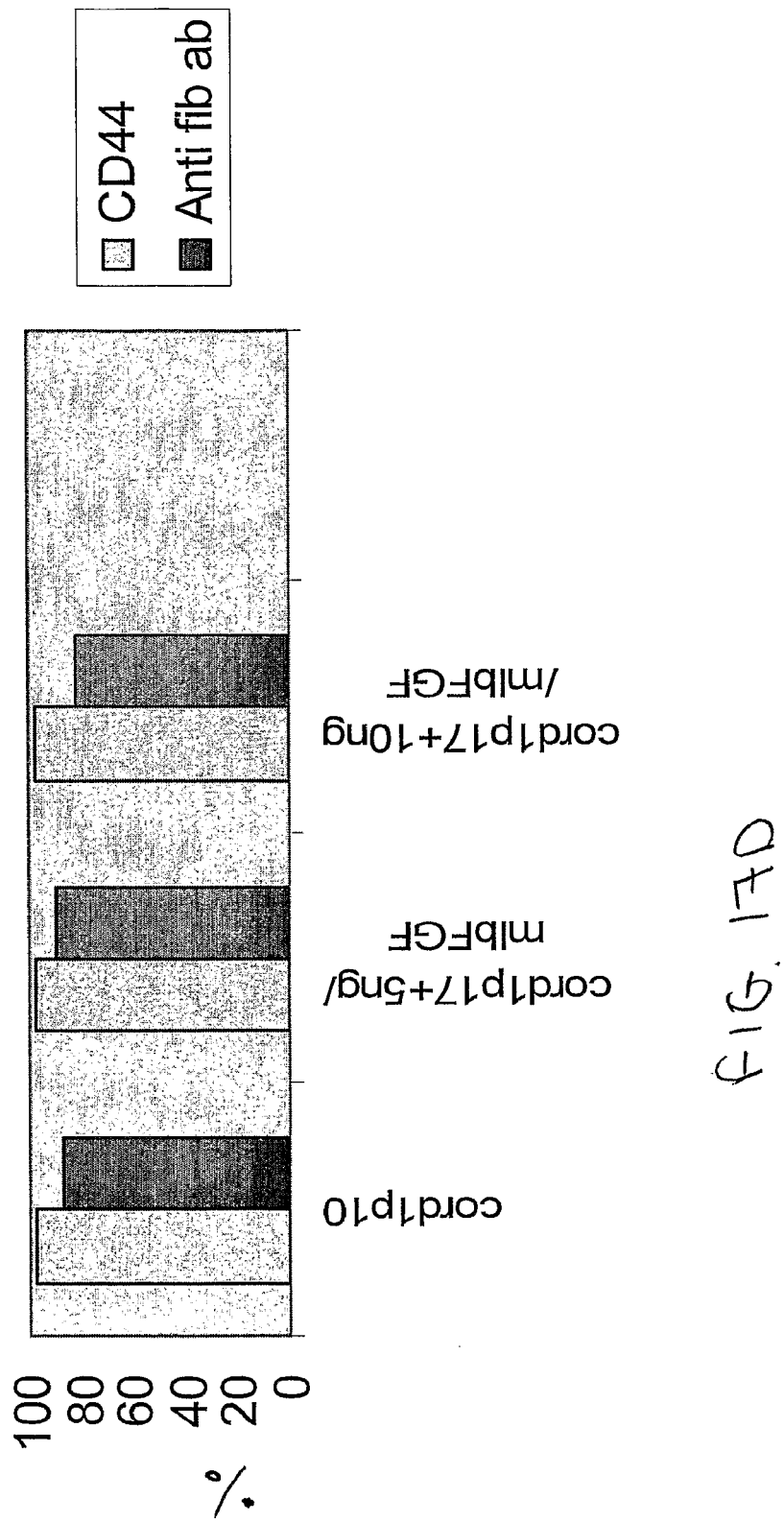
Figure 18C:
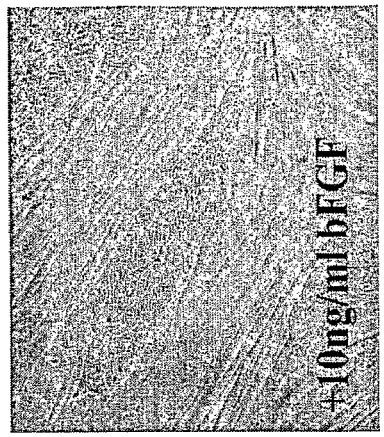
FIG. 18A-18F—are phase contrast images (FIG. 18A-18C) and immunofluorescent images (FIG. 18D-18F) of hESC colonies cultured on cord-derived fibroblasts that were propagated for 17 passages in the presence (FIGS. 18B, 18C, 18E and 18F) or absence (FIGS. 18A and 18D) of bFGF. The cord-derived fibroblasts supported undifferentiated proliferation of the hESCs as determined by the expression of alkaline phosphatase by the hESC (FIG. 18D-18F) and the expression of stem cell markers by a high percentage of the hESCs (FACS analysis, FIG. 18G).
Figure 18F:
Figure 18B:
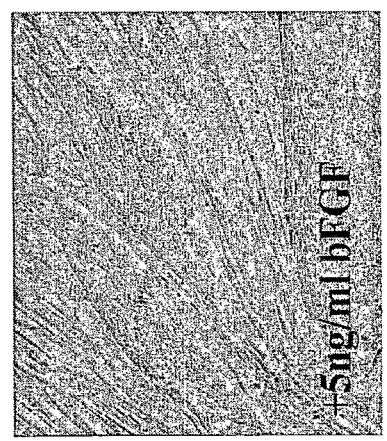
Figure 18E:
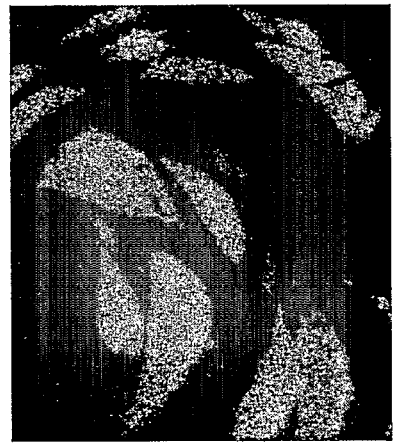
Figure 18A:
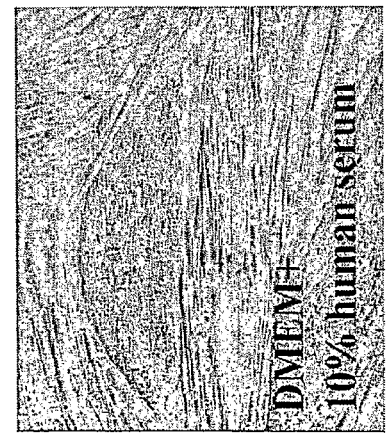
Figure 18D:
Figure 18G:
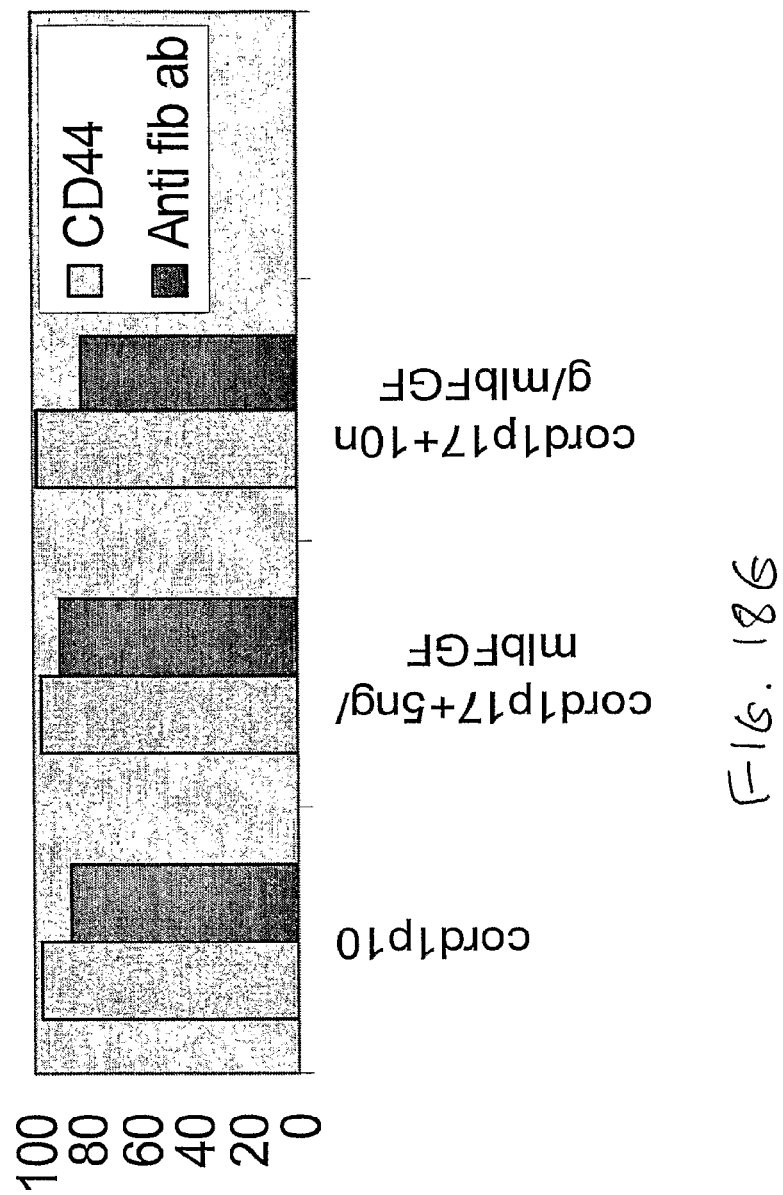

The cord-derived feeders could be maintained for prolonged periods (17 passages). It has also now been found that proliferation of the fibroblasts could be augmented by supplementation of the medium with FGF2 (FIG. 16). The fibroblasts maintained their typical morphology and marker expression following expansion with or without FGF2 supplementation (FIG. 17A-17D). Cord-derived fibroblasts that were propagated in culture for extended periods of time with or without the addition of FGF2 could support undifferented proliferation of hESC (FIG. 18A-18G).

The feeder cells from the three types of primary tissues could be successfully cryopreserved and thawed. Above 55% of the cells survived thawing. The morphology and marker expression and growth rate were not altered by cryopreservation. Cryopreserved feeders from the three sources could support undifferentiated proliferation of pluripotent hESC, as detailed above. When the feeder cells were cryopreserved with our usual cryopreservation solution (knockout (KO) DMEM, 10% DMSO, 10% KO serum replacement (SR)), or in solutions that do not include animal components (90% Human Serum and 10% DMSO), cell viability and growth rate post-thawing were similar with both cryopreservation solutions.

Human Embryonic Stem Cells

Animal-free culture system for hESC employed in the exemplary embodiments presented here, included the following components:

KO DMEM (Gibco, or equivalent), X-Vivo 10 (Biowhittaker, Maryland, or equivalent) or Cellgro Stem Cell Growth Medium (CellGenix, Freiburg, Germany, or equivalent) used as the basic media.

Humanized serum substitutes TCH (Protide Pharmaceuticals, St. Paul, Minn., or equivalent) or Nutridoma-CS (Roche, Germany, or equivalent) used as serum replacement substitute.

Human fibronectin (BD Biosciences, Badford, Mass., or equivalent) or recombinant gelatin (FibroGen, SF, or equivalent), used for tissue culture dish coating.

PBS without calcium and magnesium, supplemented with 0.05% EDTA used for splitting.

Cryosure-DMSO (Wak-Chemie, Germany, or equivalent) used for cryopreservation.

KO DMEM, X-Vivo 10, or Cellgro Stem Cell Growth Medium were used as the basic media for the propagation of undifferentiated hESC colonies on Human Embryonic Fibroblast (HEF) or foreskin feeders. These basic media were supplemented with TCH, which is an animal-free, defined serum replacement (SR) substitute. TCH replaced KO SR, which contains animal products and which is most commonly used as a supplement to KO medium.

Figure 19:
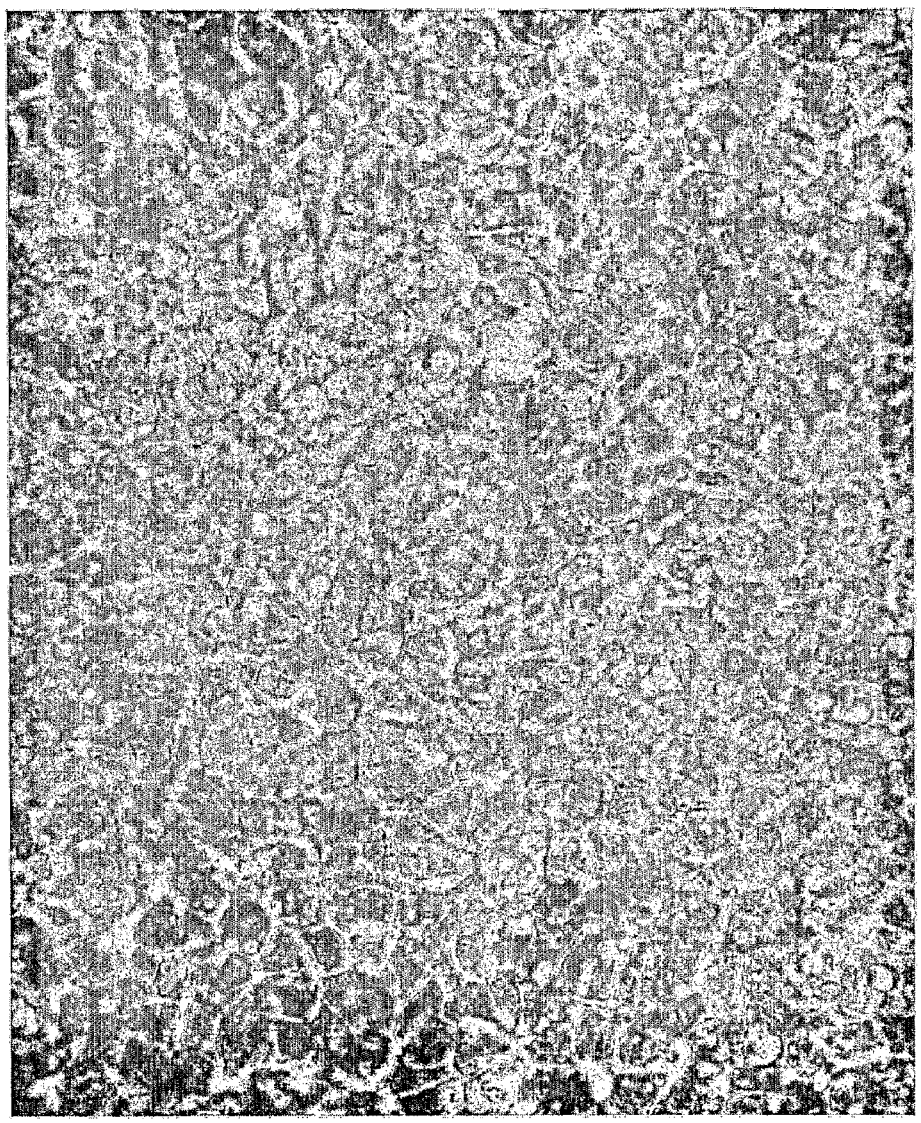
FIG. 19—is a phase contrast micrograph of hESC cultured on HEF feeder layer in Cellgro medium supplemented with 1% TCH showing that hESC retain the morphology of undifferentiated pluripotent stem cells when TCH is used as the serum replacement supplement.

Undifferentiated proliferation of hESC was obtained with TCH supplementing all three basic media. With 2% TCH in KO DMEM, 88% of the hESC that were cultured on foreskin feeders expressed SSEA-4. With 1% TCH supplementing Cellgro medium, 98% of the cells were SSEA-4+, and with 2% TCH in X-Vivo 10 medium, 99%, respectively. High percentages (86%) of the hESC also expressed the marker TRA-1-60, when propagated on HEF in Cellgro with the addition of 1% TCH. The hESC retained the morphology of undifferentiated pluripotent stem cells, when cultured in media supplemented with TCH (FIG. 19).

Figure 20:
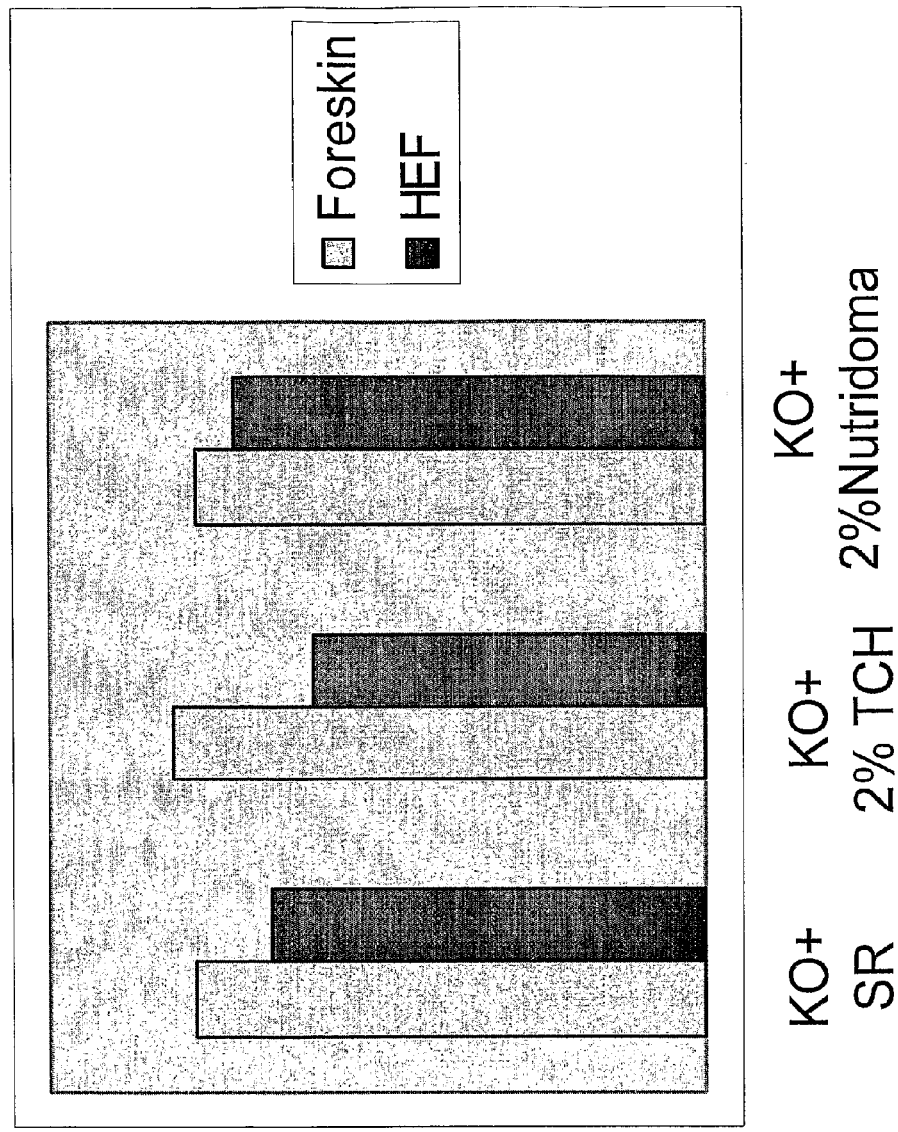
FIG. 20—is a bar graph showing the percentage of SSEA-4 expressing on hESC, when cultured on a foreskin or HEF feeder layers, being similar when the KO DMEM was supplemented with KO SR, 2% TCH, or 2% Nutridoma and showing that Nutridoma-CS is as effective as TCH in supporting undifferentiated propagation of hESC.

In addition to TCH, it has now been found that Nutridoma-CS, which is animal free, can also serve as a SR substitute for the support of undifferentiated propagation of hESC. Both TCH and Nutridoma-CS were found to be as effective as KO SR in supporting undifferentiated propagation of hESC. When hESC were cultured on human feeders (embryonic fibroblasts or foreskin) in KO DMEM supplemented with KO SR, 2% TCH, or 2% Nutridoma-CS, the percentage of cells expressing SSEA-4 was comparable in the three systems. The percentages were 93% and 79% with KO+ SR on Foreskin and HEF, respectively; 97% and 72% with KO+ TCH, and 93% and 86% with KO+ Nutridoma-CS (FIG. 20).

In the herein disclosed animal-free system, human fibronectin or recombinant gelatin replaced the animal gelatin that is most commonly used as a matrix to pre-coat the tissue culture dishes. With regard to recombinant gelatin, when hESC were cultured on a foreskin feeder layer in KO DMEM+KO SR on culture plates precoated with gelatin or recombinant gelatin, the percentage of SSEA-4+ hESC was comparable (91% and 94%, respectively). With regard to human recombinant fibronectin, when hESC were cultured in Cellgro medium supplemented with 2% TCH on a matrix of gelatin or human fibronectin, the percentage of SSEA-4+ cells was 97% and 96%, respectively, and the percentage of Tra-1-60+ cells was 92% on both matrices.

In herein disclosed humanized system, Penicillin/Streptomycin and β-Mercaptoethanol were omitted from the hESC culture media without affecting the growth rate or the level of background differentiation.

For cryopreservation of hESC, Cryosure-DMSO from Wak-Chemie, Germany, a GMP-compliant company, was successfully used. When hESC were cryopreserved in Cellgro medium supplemented with 2% TCH, and 10% Cryosure-DMSO, 2 weeks after thawing and culturing on foreskin fibroblast feeders, the percentage of hESC expressing SSEA-4 and TRA-1-60 was 98% and 95%, respectively. These results were comparable to those obtained with our usual freezing solution comprised of 90% FCS and 10% DMSO(SSEA-4 98% and TRA-1-60 96%).

In an alternative system, Neurobasal™ (NB) medium, which was initially developed for the maintenance of neural cells in ambient atmosphere, and is animal-reagent free, is used as the basic medium of the culture system. When supplemented with N2 supplement (which includes insulin, transferrin, progesterone, putrascine, selenite, NBN2) it allows undifferentiated proliferation and propagation of hESC as flat colonies on the feeders. The hESC are weekly sub-cultured following mechanical or enzymatic (dispase, type IV collagenase, or trypsin) disaggregation or treatment with Ca/Mg$^{++}$-free PBS supplemented with EDTA, or the combination of the above. The hESC retained the morphology of undifferentiated cells (FIG. 21), and expression of alkaline phosphatase (AP). The medium may be supplemented with FGF2.

Suspension Culture System for the Propagation of hESC in Bulk

To exploit the potential of hESC for high throughput screening, drug discovery, basic research, regenerative medicine, and other potential applications, large numbers of cells are required. The number of hESC that may be obtained with monolayer cultures is limited. Culture of hESC in suspension rather than in a monolayer is required to develop bulk cultures of hESC. Suspension cultures of hESC may allow extensive expansion of the cells with a bioreactor system. It may allow initiation of differentiation processes in suspension of a large number of cells, and the development of novel methodologies to direct differentiation of hESC within suspension cultures.

Propagation of hESC in suspension is achievable using Neurobasal™ medium as the basic medium of the culture system. The Neurobasal™ medium may be supplemented with N2 (NBN2). It may be further supplemented with soluble factors including but not limited to FGFs, TGFβ superfamily factors, BMPs antagonists as well extracellular matrix (ECM) components including but not limited to fibronectin, laminin, gelatin to promote proliferation and survival of the cells and to prevent their differentiation.

To develop suspension cultures, hESC colonies that are cultivated on human feeders in the KO culture system are dissociated with the aid of type IV collagenase or Ca/Mg$^{++}$-free PBS supplemented with 0.05% EDTA. The cells/cell clusters that are obtained are re-suspended within fresh NBN2 medium, supplemented with FGFs (bFGF 20 ng/ml).

Further supplementation of the medium with the following components increases the survival/proliferation and prevent differentiation of the cells:

TGFβ superfamily factors (activin 25-50 ng/ml)
BMPs antagonists (noggin 250 ng/ml)
ECM components (laminin 5 ng/ml, fibronectin 5 ng/ml, gelatin 0.001%)

Figure 22B:
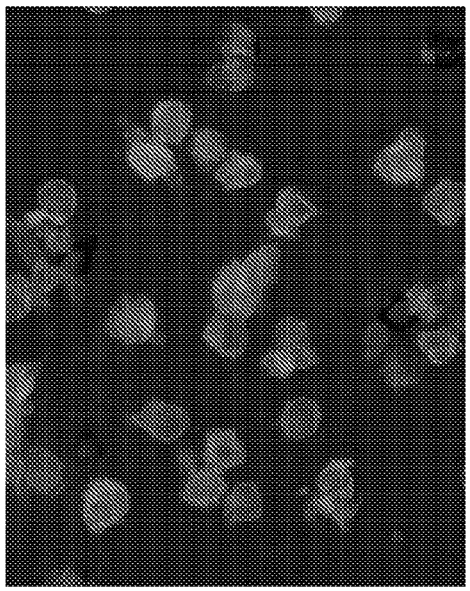
FIG. 22A-22D—are dark field micrographs of small transparent clusters of cells that develop 7 days after transfer of undifferentiated hESCs into suspension culture within NBN2 medium (FIG. 22A) and after 3 weeks in suspension culture within NBN2, indirect immunofluorescent analysis showed that the majority of hESCs express SSEA4 (FIG. 22B) and Oct4 (FIG. 22D). Nuclei of cells in D are counterstained with DAPI in (FIG. 22C).
Figure 22D:
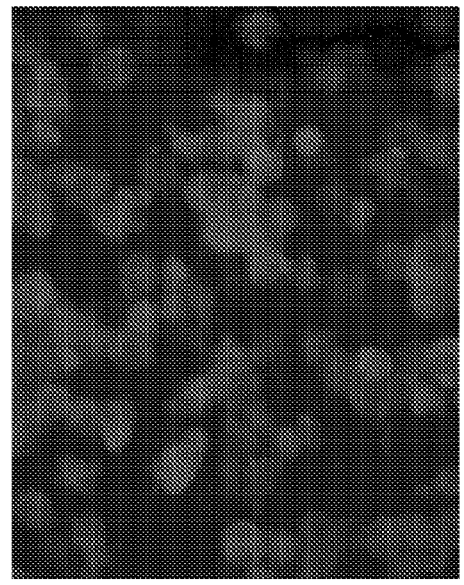
Figure 22A:
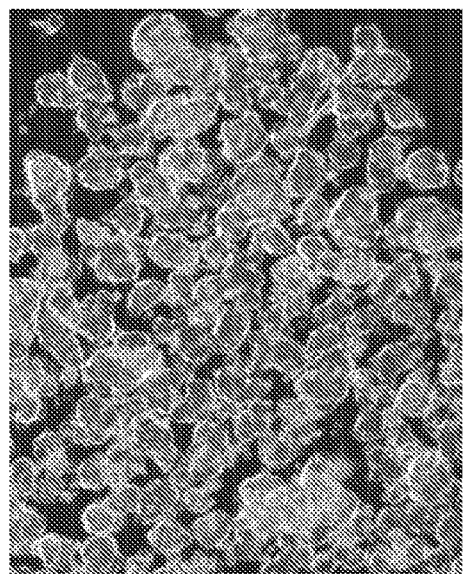
Figure 22C:
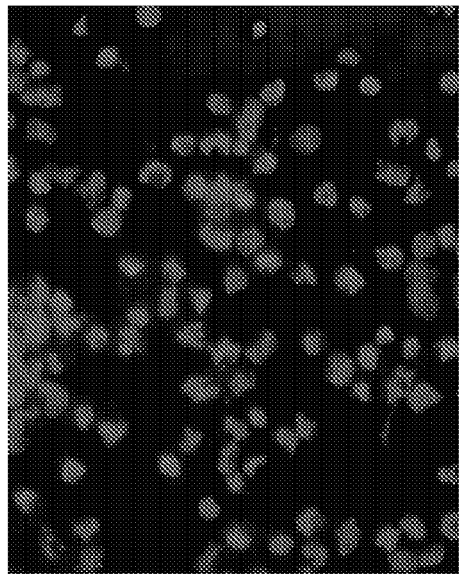

The cells are transferred to suspension at a density of ~0.7-1.2×10$^6$ cells/ml. Dead/fragmented cells are gradually removed during medium refreshment. After 3-5 days of suspension culture, small transparent cell-aggregates develop. These transparent cells proliferate as free-floating tiny clusters of 20-50 cells without any morphological signs of differentiation (FIG. 22A). Aggregation and overgrowth of the transparent clusters may be prevented by daily trituration through a 1000 μl pipette tip or by the use of bioreactor. The cells express SSEA4 and OCT4, (FIGS. 22B and 22D respectively). When re-plated on human feeders, after 6 weeks of suspension culture, they give rise to colonies with the morphology of undifferentiated hESCs.

It was further found and disclosed herein that when the hESCs are cultivated 3 weeks in suspension under these culture conditions in medium supplemented with all the above mentioned components, ≥85% of the cells express SSEA4. Thus, these culture conditions can support undifferentiated cultivation of hESC in suspension.

Analysis of the effect of each of the components, in the presence of FGF2, showed that ECM components promoted survival/proliferation of hESCs (FIG. 23B Lam=laminin, Fn=fibronectin, Gel=gelatin), activin A prevented differentiation (FIG. 23A), and noggin could promote survival/proliferation (FIG. 23B).

Nicotinamide may be added to the medium to prevent the differentiation of the cells towards extraembryonic lineages, to promote their survival and to maintain them undifferentiated.

Nicotinamide (NA) for the Maintenance of Undifferentiated hES Cells, Prevention of Extraembryonic Differentiation, and for the Induction of Somatic Differentiation.

Figure 24B:
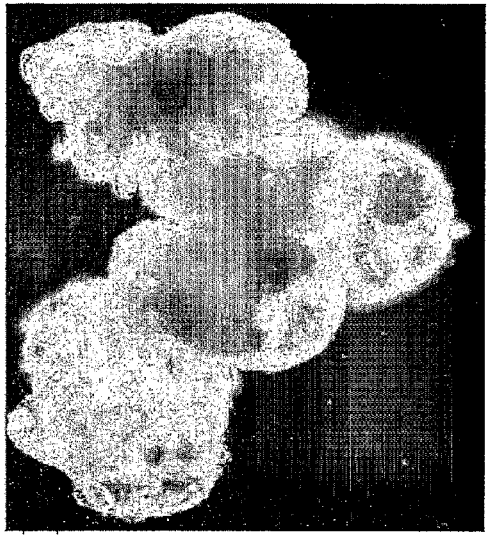
FIG. 24A-24D—are dark field micrographs of EBs that were cultured for 4 weeks in the presence and absence of NA (the culture medium included 10% FCS). EBs with typical cystic structures (cystic EBs) developed in the absence of NA (FIGS. 24A and 24B), while in the presence of NA, cystic formation was not observed and the EBs were comprised of tightly packed cells (FIGS. 24C and 24D).
Figure 24A:
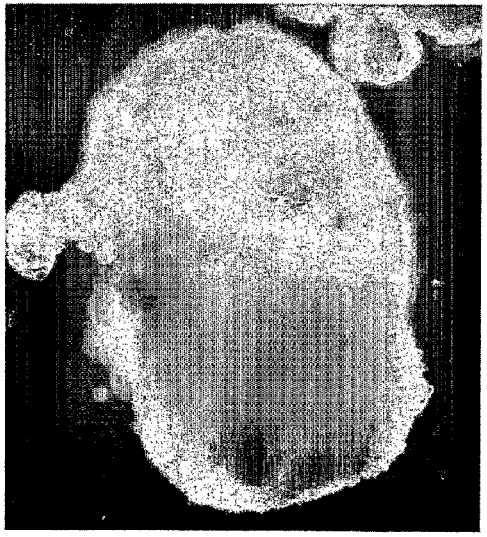
Figure 24D:
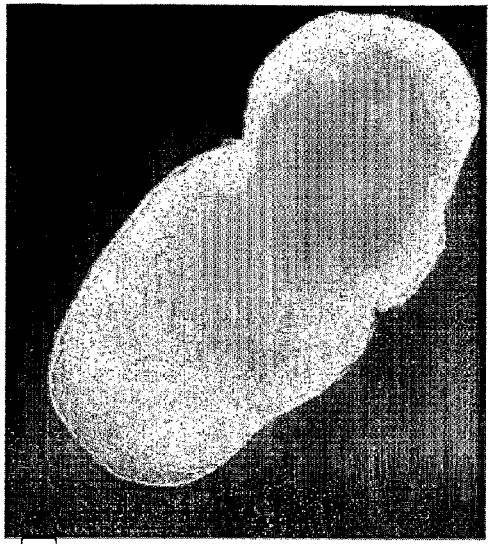
Figure 24C:
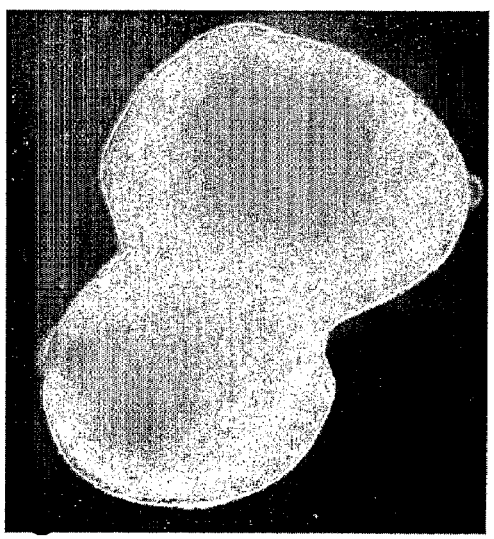

The novel effect of NA on hESCs' differentiation was most profoundly demonstrated during spontaneous differentiation of hESCs within embryoid bodies (EBs). When hESCs differentiate within free-floating clusters, in serum-supplemented medium, with time they develop into cystic EBs which include cystic structures and areas of more densely packed cells (FIGS. 24A-24B). These cystic structures are attributed in mouse EBs to extraembryonic endodermal differentiation [Coucouvanis, E. & Martin, G. R. Signals for death and survival: a two-step mechanism for cavitation in the vertebrate embryo. *Cell* 83, 279-287 (1995); Doetschman, T. C., et al. The in vitro development of blastocyst-derived embryonic stem cell lines: formation of visceral yolk sac, blood islands and myocardium. *J Embryol Exp Morphol* 87, 27-45 (1985)]. However, in the presence of NA, preferably at a concentration of 10 mM, cystic structures were not formed during differentiation within EBs (FIGS. 24C-24D). Moreover, the differentiated cells acquired the morphology of neural precursor cells.

The effect of NA on differentiation within EBs was not dependent on the presence of serum and was observed also when EBs differentiated in a chemically-defined medium (NBN2; FIGS. 25A-25H, i.e. upper two panels).

In addition to its effect on differentiation, NA also had an effect on the size of the EBs. In serum-free medium supplemented with NA, the size of the Ebs after two weeks of differentiation was significantly higher (1.7 times; maximal diameter of EBs) in comparison to the size of EBs that were cultured under the same conditions in the absence of NA (FIGS. 25E-25F, i.e. left pictures of upper two panels). The increased size of the EBs in the presence of NA reflected an increase in the number of cells within the EBs. When EBs were generated from a comparable number of undifferentiated cells, after 2 and 4 weeks, there were 5.4 and 33 times more cells respectively, in cultures that were treated with NA as compared to controls. Thus NA can be used to increase the number of differentiated cells that are obtained from hESC.

Furthermore NA treatment allowed the prolonged culture of EBs for 12 weeks (FIG. 28). Prolonged culture of EBs is important for the completion of complex differentiation processes that require long time periods, and may promote the maturation of differentiated cells.

Retinoic acid is known to induce extraembryonic differentiation of human pluripotent stem cells (Roach, S., Schmid, W., Pera, M F. Hepatocytic transcription factor expression in human embryonal carcinoma and yolk sac carcinoma cell lines: expression of HNF-3 alpha in models of early endodermal cell differentiation. *Eep Cell Res* 215, 189-98 (1994). When hESC-derived EBs were cultured in the presence of RA there was extensive cystic formation. NA could block the effect of RA and when EBs were cultured in the presence of RA and NA the development of cystic structures was infrequent (FIGS. 25I-25P, i.e. lower two panels).

In addition, the number of differentiated cells that were obtained in the presence of RA was low. This effect of RA was also blocked when the medium was supplemented with NA (FIGS. 25I-25P, lower two panels).

Figure 26:
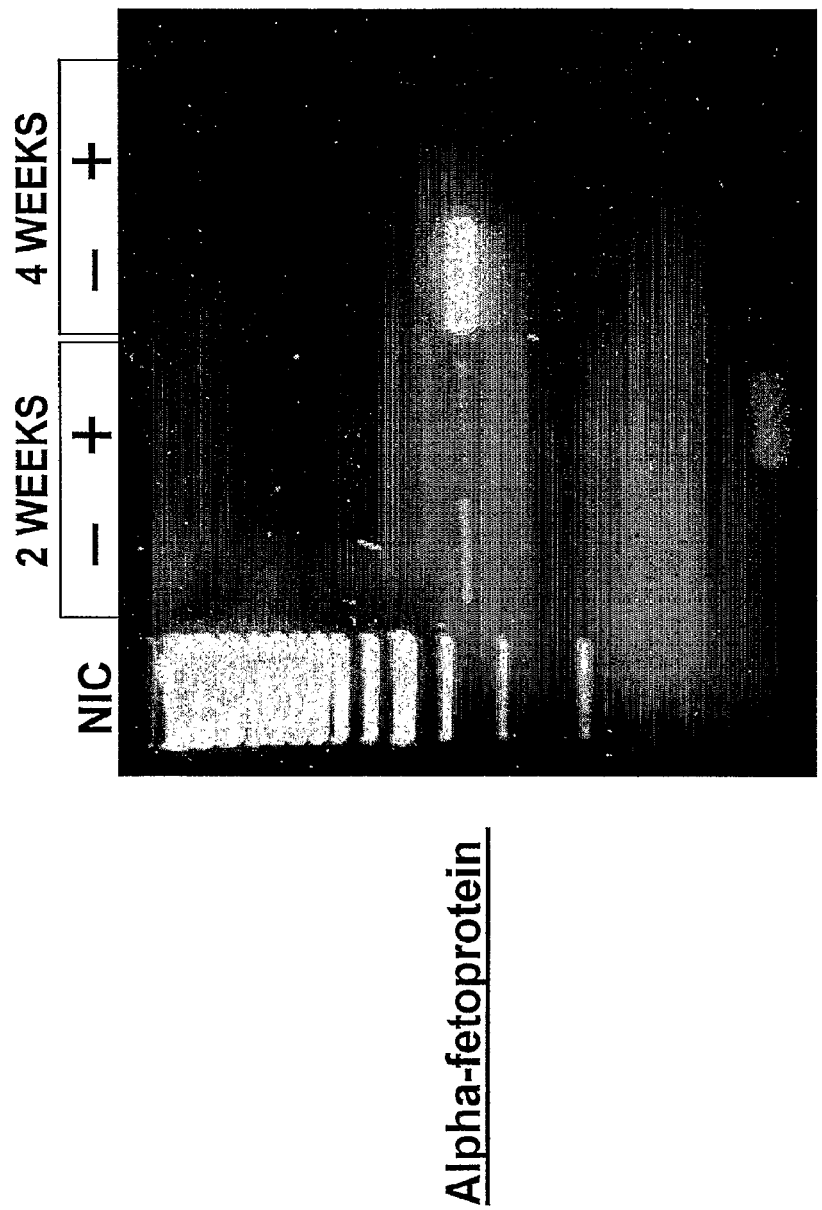
FIG. 26—is a RT-PCR analysis demonstrating that the expression of the endodermal marker α-fetoprotein is suppressed within EBs that differentiated in the presence of NA in comparison to control EBs that were cultured in the absence of NA. After 4 weeks of differentiation, the effect of NA was more prominent in comparison to the effect after 2 weeks.
Figure 27A:
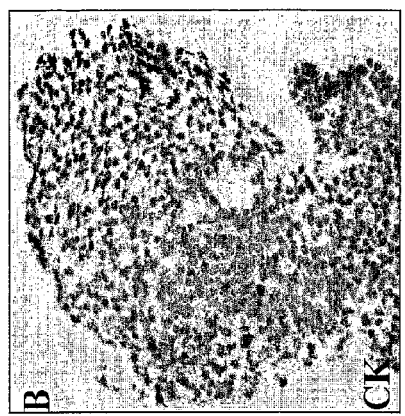
FIGS. 27A-27D—are immunocytochemical studies demonstrating suppressed expression of α-fetoprotein (AFP) and cytokeratin-8 (CK) in EBs that differentiated in the presence of NA. Following 4 weeks of differentiation in the presence of NA, only a few cells in sections of EBs were immunoreactive with anti-α-fetoprotein (FIG. 27A) and cytokeratin-8 (FIG. 27B). Cells that expressed α-fetoprotein (FIG. 27C) and cytokeratin-8 (FIG. 27D) were abundant within sections of control EBs that differentiated in the absence of NA.
Figure 27B:
Figure 27C:
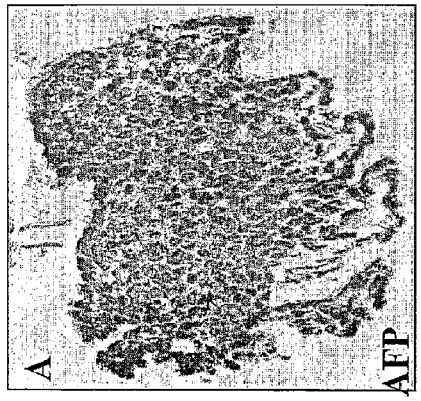
Figure 27D:
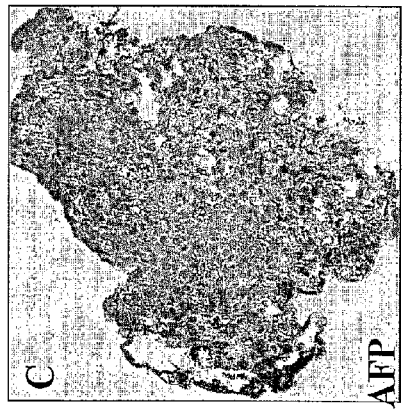

Immunocytochemical and RT-PCR studies showed that the expression of the endodermal (extraembryonic and definitive) marker α-fetoprotein, which is expressed by cells within EBs that are cultured in the presence of serum, was not detected within the EBs following differentiation in the presence of NA (FIGS. 26 and 27A, 27C). Similarly, Cytokeratin-8, which is a nonspecific marker of a wide range of epithelial tissues, including extraembryonic tissues [Pera, M. F. et al. Regulation of human embryonic stem cell differentiation by BMP-2 and its antagonist noggin. *J Cell Sci* 117, 1269-1280 (2004); Kemler, R., et al. Reactivity of monoclonal antibodies against intermediate filament proteins during embryonic development. *J Embryol Exp Morphol* 64, 45-60 (1981)], and which is widely expressed within EBs, was not demonstrated within EBs that were developed in the presence of NA (FIGS. 27B and 27D).

A high percentage of the cells within EBs that differentiated in the presence of NA (for 6 weeks) expressed neural precursor markers in comparison to control EBs that were developed in the absence of NA (PSA-NCAM 85.5% vs. 19.9% respectively, FACS analysis). In addition, indirect immunofluorescence studies showed that in the presence of NA, 58.3% of the cells expressed nestin, and 67.8% expressed β-tubulin III.

Within the neural lineage, NA treatment was found to promote differentiation towards RPE cells. RPE cells, which lie immediately underneath the photoreceptors and form part of the retina-blood barrier towards the choroid, play a crucial role in supporting and maintaining the photoreceptors. Their tasks include active transport of nutrients from the choroidal vessels to the photoreceptors, processing of vitamin A, and uptake and recycling of outer segments which are continuously shed by the photoreceptors. While primary degeneration of the photoreceptors is the cause of progressive visual loss in some types of Retinitis Pigmentosa, in others the initial injury is in RPE cells, and as a consequence, the photoreceptors are damaged as well and retinal degeneration ensues. Even more importantly, in Age-Related Macular Degeneration (AMD), which is the most common cause of blindness among the elderly aging population, failure of the RPE is the main cause of disease [Smith W, Assink J, Klein R et al. Risk factors for age-related macular degeneration: Pooled findings from three continents. *Ophthalmology* 2001; 108:697-704.

Thus, derivation of this cell type from hESC may be of great benefit. They may be used as an in vitro model for the development of new drugs to promote their survival and function. hESC-derived RPE cells may serve for high throughput screening for compounds that are toxic to RPE cells. They may be used to uncover mechanisms, new genes, soluble or membrane-bound factors that are important for the development, differentiation, maintenance, survival and function of photoreceptor cells. These cells may serve as an unlimited source of RPE cells for transplantation and replenishment of malfunctioning or degenerated RPE cells in retinal degenerations. Genetically modified RPE cells may serve as a vector to carry and express genes in the retina after transplantation.

Figure 29:
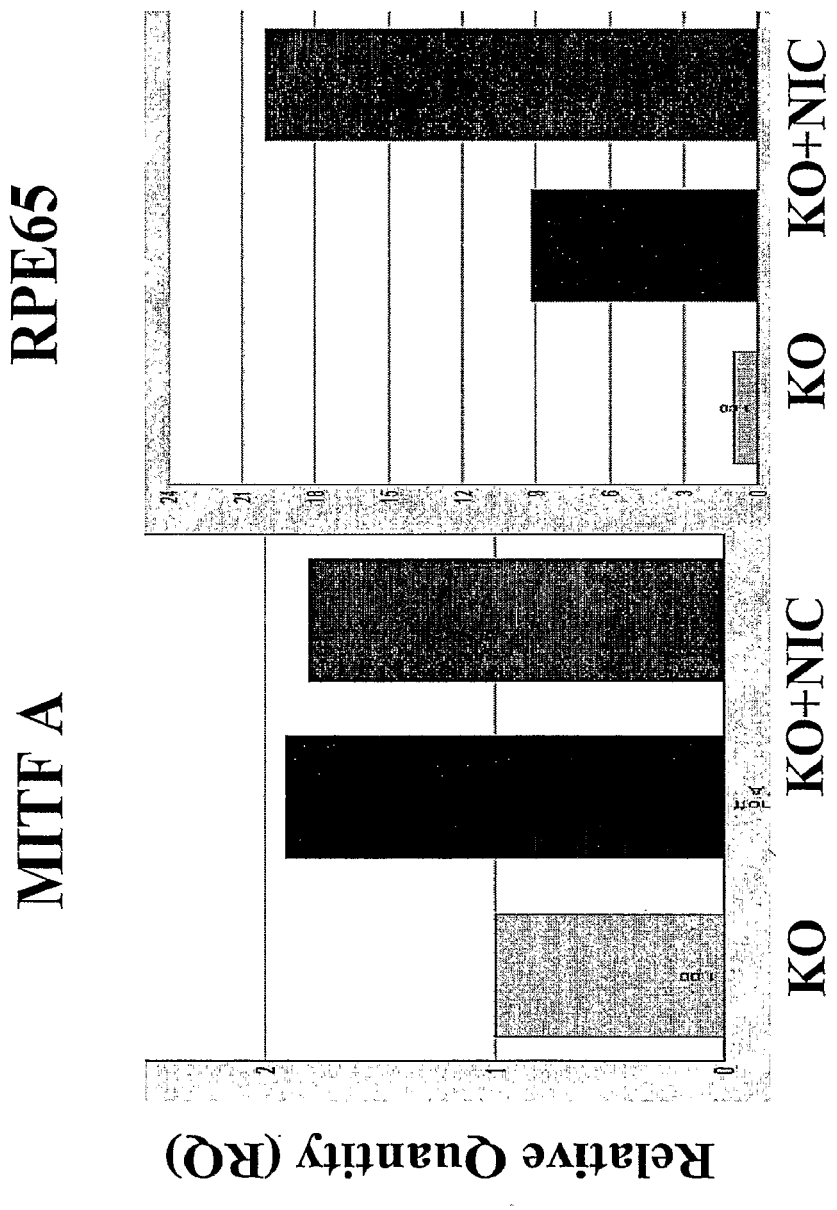
FIG. 29—is a real time PCR analysis of EBs differentiated for 6 weeks in the presence or absence of NA, demonstrating the induction of expression of RPE markers by NA.
Figure 30:
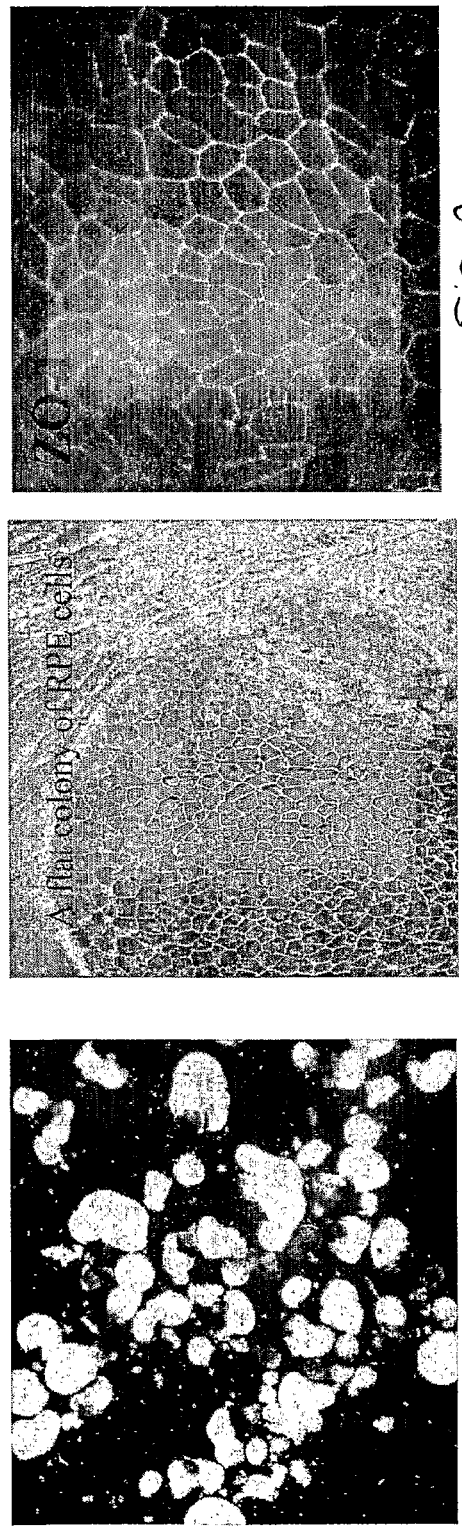
FIGS. 30A-30H—are images showing that melanin-expressing cells that were generated in the presence of NA had morphological characteristics that are typical of RPE cells. Specifically shown are dark field micrograph (FIG. 30A), phase contrast image (FIG. 30B) and indirect immunofluorescent stainings of RPE cells markers including ZO-1 (FIG. 30C), Pax6 (FIG. 30D), MITF (FIG. 30E), CRALBP (FIG. 30F), Bestrophin (FIG. 30G) and RPE65 (FIG. 30H).
Figure 30E:
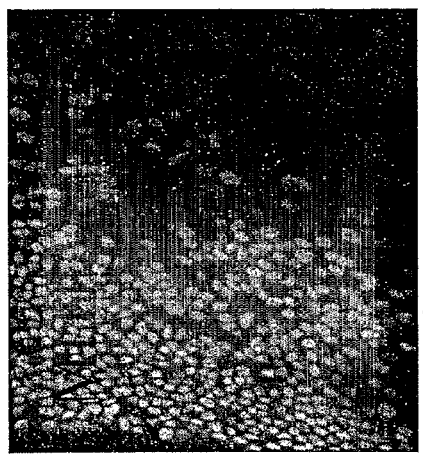
Figure 30D:
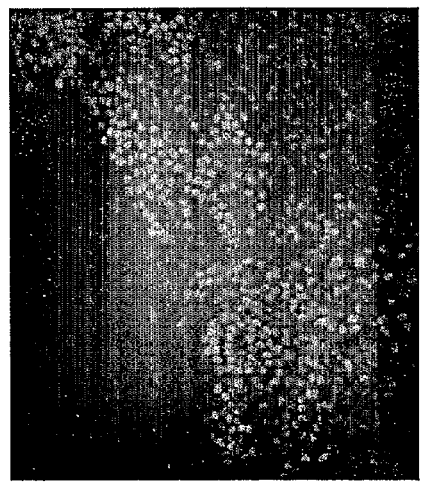
Figure 30H:
Figure 30G:
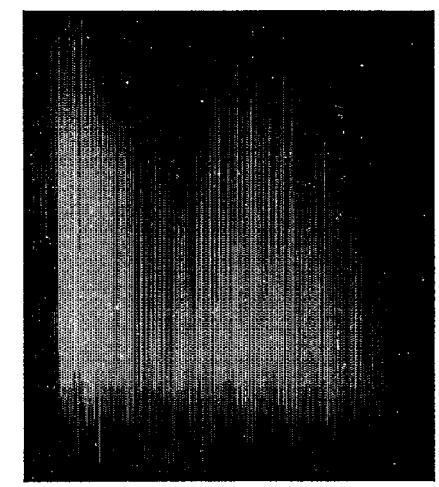
Figure 30F:
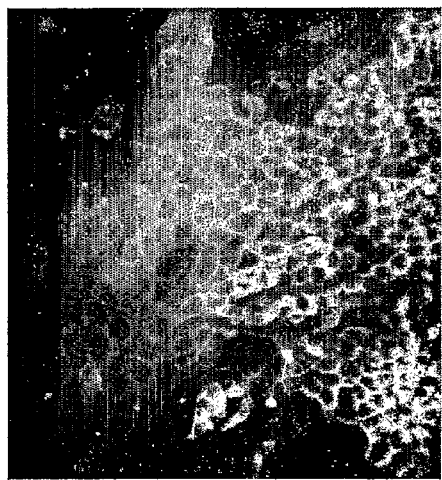

While pigmented cells were rarely observed within hESC-derived EBs that were differentiating in KO medium, clusters of pigmented cells were abundant within EBs differentiating in the presence of NA. The percentage of EBs that included clusters of pigmented cells gradually increased along differentiation in the presence of NA (34%, 59% and 70% at 5, 6 and 12 weeks of differentiation respectively; FIGS. 28A-28D. After 6 weeks of differentiation, 9% of the cells within the EBs were pigmented. The potential of NA to induce differentiation towards RPE cells was also demonstrated at the RNA level by Real Time PCR. The expression of the RPE markers RPE65 and MITF A was significantly increased in EBs that differentiated in the presence of NA compared to control EBs (FIG. 29).

When the EBs were partially dissociated and plated, colonies that were comprised of a monolayer of the pigmented cells were formed between other types of differentiated cells (FIGS. 30A-30H). Indirect immunofluorescent staining showed that the pigmented cells expressed multiple markers of RPE cells including PAX6, MITF, ZO-1, CRALBP, Bestrophin and RPE65 thus confirming the retinal identity of the pigmented cells.

It was possible to enrich the cultures for the RPE cells by isolating the pigmented cells from other cells within the EBs by mechanical dissection. Other methods such as genetic selection, immunopanning, FACS and others may be used to purify the cultures for RPE cells.

Figure 32B:
FIG. 32A-C—are H&E and fluorescent images demonstrating the survival of transplanted hESC-derived RPE cells and their integration within the host RPE layer of cells. An H&E image showing the survival of an intra-vitreal graft, 4 weeks after transplantation into the eye of a mature RCS rat (FIG. 32A). The graft includes melanin expressing cells (dark pigmented cells). Indirect immunofluorescent staining demonstrates that the cells within the graft express GFP (white spots), confirming their human identity (FIG. 32B). Integration of transplanted hESC-derived RPE cells (pigmented cells marked with arrows) in the albino rat RPE layer is also demonstrated (FIG. 32C). Pigmented cells were not observed in the RPE layer of control non transplanted eyes.
Figure 32C:
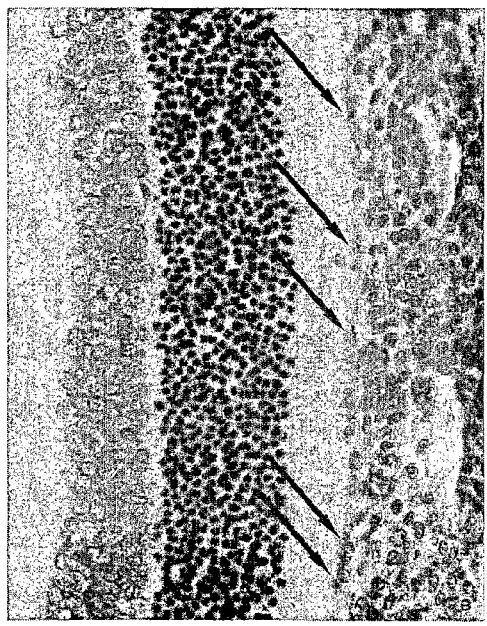
Figure 32A:

Enriched populations of hESC-derived RPE cells were transplanted into the vitreous and into the subretinal space of RCS and albino rats respectively. Immuno-histological analysis of the eyes, at 4 weeks after transplantation, demonstrated surviving hESC-derived RPE cells (FIG. 32A-32B). Transplanted RPE cells migrated from subretinal grafts and integrated within the RPE layer of host albino rats (FIG. 32C).

A differential comparison of the gene expression profile of EBs after 4 weeks of suspension culture in the presence and absence of NA was performed by using affymetrix gene arrays. The expression level of 1072 genes was up- or down-regulated by at least two-fold; 442 genes were up-regulated, and 630 genes were down-regulated. The analysis confirmed that NA suppressed the expression of α-fetoprotein and cytokeratin-8. In addition, the expression of other cytokeratins was also suppressed, including cytokeratins 7, 18, 19, 23.

Figure 31:
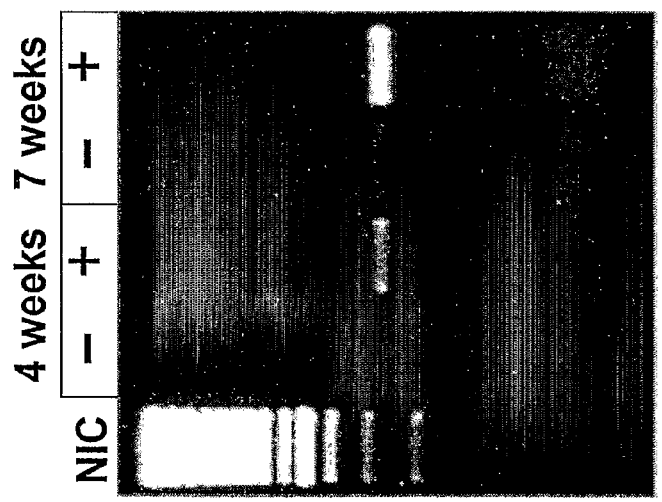
FIG. 31—is RT-PCR analysis showing the expression of chordin-like 1 by cells within EBs that were developed in the presence of NA.

Interestingly, the expression of chordin-like-1 gene was up-regulated. This finding was further confirmed by RT PCR (FIG. 31). Chordin-like is composed of three cysteine-rich (CRs) domains. Chordin-like binds BMP-4, BMP-5, BMP-6 and TGF-β1&2 [Nakayama, N. et al. A novel chordin-like protein inhibitor for bone morphogenetic proteins expressed preferentially in mesenchymal cell lineages. *Dev Biol* 232, 372-387 (2001)]. In the early mouse embryo, chordin expression is restricted to the node and the notochord at a time in which chordin-like is expressed in the neural plate [Garcia Abreu, J., et al. Chordin-like CR domains and the regulation of evolutionarily conserved extracellular signaling systems. *Gene* 287, 39-47 (2002)]. NA treatment induced the expression of genes that are involved in active Wnt signaling pathway including Wnt4, Wnt 2B, Frizzled (FZD) 1, FZD2, FZD3, FZD10.

In line with the morphological and immunostaining findings that showed the potential of NA to promote neural differentiation, the expression of ZIC1, a zic family member 1, that is expressed during neural differentiation, was remarkably up-regulated in the presence of NA. The expression of left-right-determination factor (LEFT) A & B as well as PITX1 was down regulated.

The invention claimed is:

1. A method for maintaining human pluripotent stem cells in an undifferentiated state, comprising:
   providing human umbilical cord fibroblast feeder cells isolated and expanded from human umbilical cord;
   incubating the human pluripotent stem cells in a culture system comprising the human umbilical fibroblast feeder cells, the feeder cells consisting essentially of human umbilical cord fibroblast feeder cells, the culture system being free from antibacterial agents and mercaptoethanol; and
   maintaining the human pluripotent stem cells in an undifferentiated state for at least 10 weeks.

2. The method of claim 1, wherein the human pluripotent stem cells are embryonic stem cells.

3. The method of claim 1, for propagating the human pluripotent stem cells in an undifferentiated state.

4. The method of claim 1, wherein the human umbilical cord feeder cells consist of 100% human umbilical cord fibroblast feeder cells.

5. The method of claim 1, wherein the culture system further comprises nicotinamide.

6. A method for maintaining human pluripotent stem cells in an undifferentiated state, comprising:
   providing human umbilical cord fibroblast feeder cells comprising
      expanding human umbilical cord cells to obtain human umbilical cord feeder cells, and
      isolating human umbilical cord fibroblast feeder cells from the human umbilical cord feeder cells, to obtain human umbilical cord fibroblast feeder cells; and
   incubating the human pluripotent stem cells in a culture system comprising the human umbilical cord fibroblast feeder cells, and the culture system is free from antibacterial agents and mercaptoethanol.

7. The method of claim 6, wherein the human umbilical cord feeder cells consists essentially of the human umbilical cord fibroblast feeder cells.

8. The method of claim 7, wherein the human umbilical cord feeder cells consist of the human umbilical cord fibroblast feeder cells.

9. The method of claim 6, wherein the culture system further comprises nicotinamide.

* * * * *